US009963674B2

(12) United States Patent
Studer et al.

(10) Patent No.: US 9,963,674 B2
(45) Date of Patent: May 8, 2018

(54) AGE-MODIFIED CELLS AND METHODS FOR MAKING AGE-MODIFIED CELLS

(71) Applicant: Memorial Sloan-Kettering Cancer Center, New York, NY (US)

(72) Inventors: Lorenz Studer, New York, NY (US); Justine D. Miller, Albany, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days. days.

(21) Appl. No.: 14/884,503

(22) Filed: Oct. 15, 2015

(65) Prior Publication Data

US 2016/0115444 A1 Apr. 28, 2016

Related U.S. Application Data

(63) Continuation of application No. PCT/US2014/034435, filed on Apr. 16, 2014.

(60) Provisional application No. 61/812,464, filed on Apr. 16, 2013, provisional application No. 61/907,262, filed on Nov. 21, 2013.

(51) Int. Cl.

| | |
|---|---|
| ***G01N 33/50*** | (2006.01) |
| ***C12N 5/079*** | (2010.01) |
| ***C12N 5/074*** | (2010.01) |

(52) U.S. Cl.

CPC ......... *C12N 5/0618* (2013.01); *C12N 5/0696* (2013.01); *G01N 33/502* (2013.01); *G01N 33/5023* (2013.01); *G01N 33/5058* (2013.01); *G01N 33/5073* (2013.01); *C12N 2501/40* (2013.01); *C12N 2501/998* (2013.01); *C12N 2503/02* (2013.01); *C12N 2506/1307* (2013.01)

(58) Field of Classification Search

None

See application file for complete search history.

(56) References Cited

U.S. PATENT DOCUMENTS

2012/0329066 A1 12/2012 Gordon et al.
2014/0336236 A1* 11/2014 Cronin ............... C07K 14/4738 514/44 A

FOREIGN PATENT DOCUMENTS

KR 1020120106286 A 9/2012

OTHER PUBLICATIONS

Grskovic et al in "Induced pluripotent stem cells—opportunities for disease modelling and drug discovery" (Nature Reviews vol. 10, Dec. 2011, pp. 915-929).*

Freije et al., "Reprogramming aging and progeria," Current Opinion in Cell Biology 24(6):757-764 (2012).

Goldman et al., "Accumulation of mutant lamin A causes progressive changes in nuclear architecture in Hutchinson-Gilford progeria syndrome," PNAS 101(24):8963-8968 (2004).

Liu et al., "iPSC technology to study human aging and aging-related disorders," Current Opinion in Cell Biology 24(6):765-774 (2012).

Liu et al., "Recapitulation of premature ageing with iPSCs from Hutchinson-Gilford progeria syndrome," Nature 472(7342):221-225 (2011).

Manju et al., "Expression of disease-causing lamin A mutants impairs the formation of DNA repair foci," Journal of Cell Science 119(13):2704-2714 (2006).

Mounkes et al., "Aging and nuclear organization: lamins and progeria," Current Opinion in Cell Biology 16(3):322-327 (2004).

Scaffidi et al., "Lamin A-dependent misregulation of adult stem cells associated with accelerated ageing," Nature Cell Biology 10(4):452-459 (2008).

Shumaker et al., "Mutant nuclear lamin A leads to progressive alterations of epigenetic control in premature aging," PNAS 103(23):8703-8708 (2006).

Supplementary European Search Report dated Sep. 28, 2016 in Application No. EP 14784841.

Vlcek et al., "Lamins and lamin-associated proteins in aging and disease," Current Opinion in Cell Biology, Current Science 19(3):298-304 (2007).

Xiong et al., "An inhibitory role of progerin in the gene induction network of adipocyte differentiation from iPS cells," Aging-US 5(4):288-303 (2013).

Cao et al., "Progerin and telomere dysfunction collaborate to trigger cellular senescence in normal human fibroblasts" *The Journal of Clinical Investigation*, 2011, vol. 121, No. 7, pp. 2833-2844.

Capell et al., "Inhibiting farnesylation of progerin prevents the characteristic nuclear blebbing of hutchinson-gilgord progeria syndrome" *PNAS*, 2005, vol. 102, No. 36, pp. 12879-12884.

Cornacchia et al., "Back and forth in time: Directing age in iPSC-derived lineages" *Brain Research* (Nov. 17, 2015), http://dx.doi.org/10.1016/j.brainres.2015.11.013.

International Search Report dated Sep. 24, 2014 in International Application No. PCT/US2014/034435.

Miller et al., "Human iPSC-based modeling of late-onset disease via progerin-induced aging" *Cell Stem Cell*, Dec. 5, 2013, vol. 13, No. 6, pp. 691-705.

Moulson et al., "Increased progerin expression associated with unusual LMNA mutations causes severe progeroid syndromes" *Human Mutation*, 2007, vol. 28, No. 9, pp. 882-889.

(Continued)

*Primary Examiner* — Catherine S Hibbert
(74) *Attorney, Agent, or Firm* — Baker Botts L.L.P.

(57) ABSTRACT

Provided are age-modified cells and method for making age modified cells using progerin or a progerin-like protein. The aging and/or maturation process can be accelerated and controlled for young and/or immature cells, such as a somatic cell, a stem cell, a stem cell-derived somatic cell, including an induced pluripotent stem cell-derived cell, by contacting with progerin or a progerin-like protein. Methods described by the present disclosure can produce age-appropriate cells from a somatic cell or a stem cell, such as an old cell and/or a mature cell. Such age-modified cells constitute model systems for the study of late-onset diseases and/or disorders.

14 Claims, 20 Drawing Sheets

(56) References Cited

OTHER PUBLICATIONS

Vera et al., "When rejuvenation is a problem: challenges of modeling late-onset neurodegenerative disease" *Development* Sep. 15, 2015;142(18):3085-9.

* cited by examiner

FIG. 7A
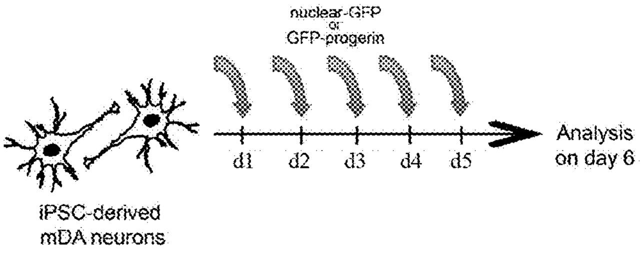
FIG. 7B
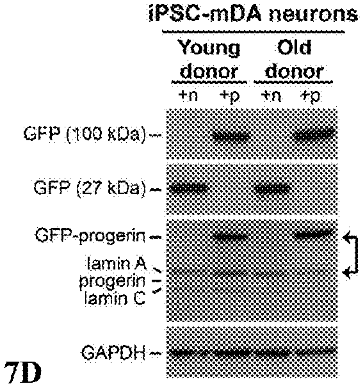
FIG. 7C
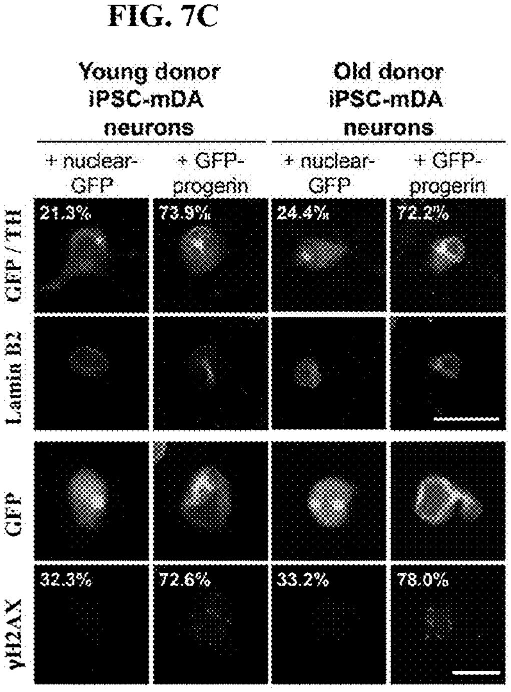
FIG. 7D
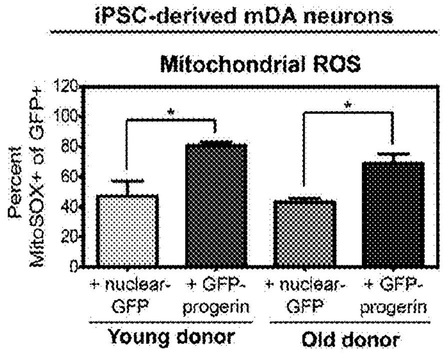
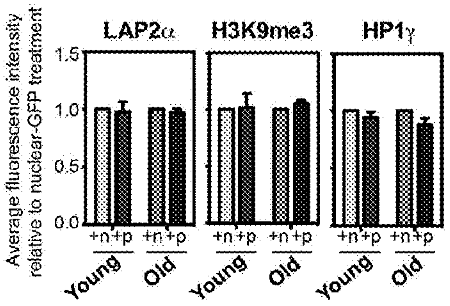
FIG. 7E Day 70 iPSC-derived mDA neurons FIG. 9A
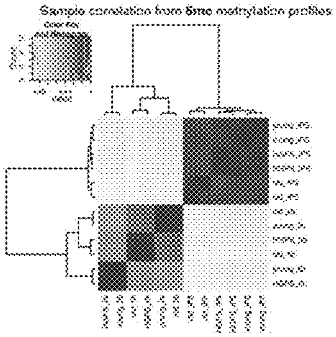
FIG. 9B
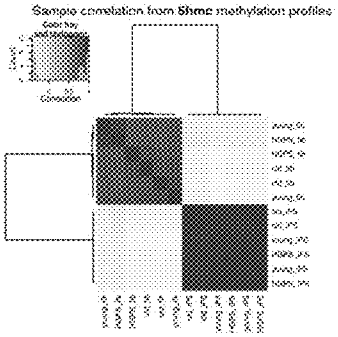
FIG. 9C
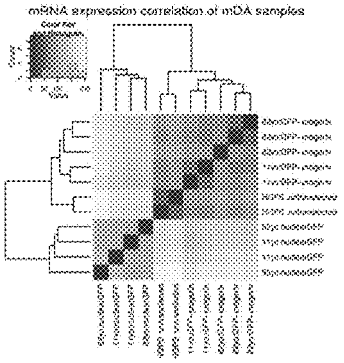
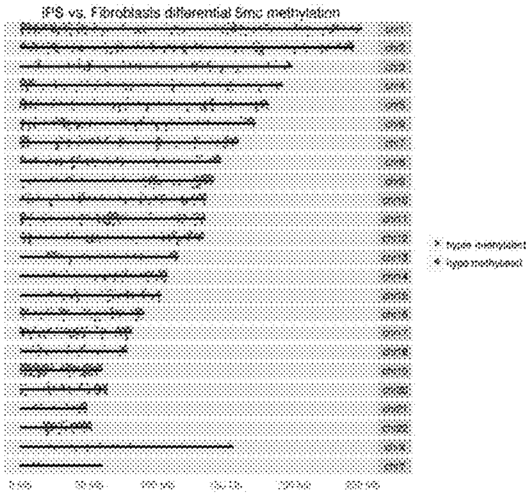
FIG. 9D
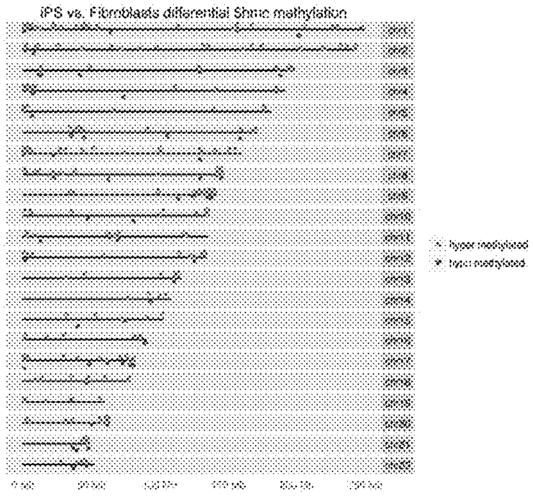
FIG. 9E

A

FIG. 12A
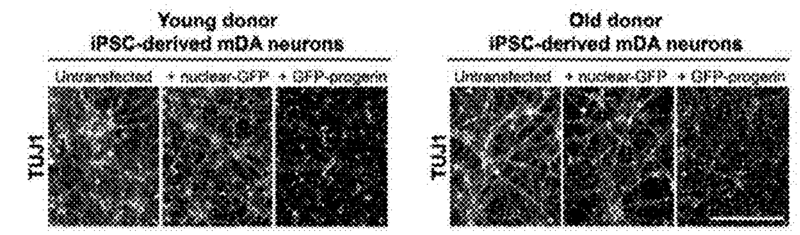
FIG. 12B
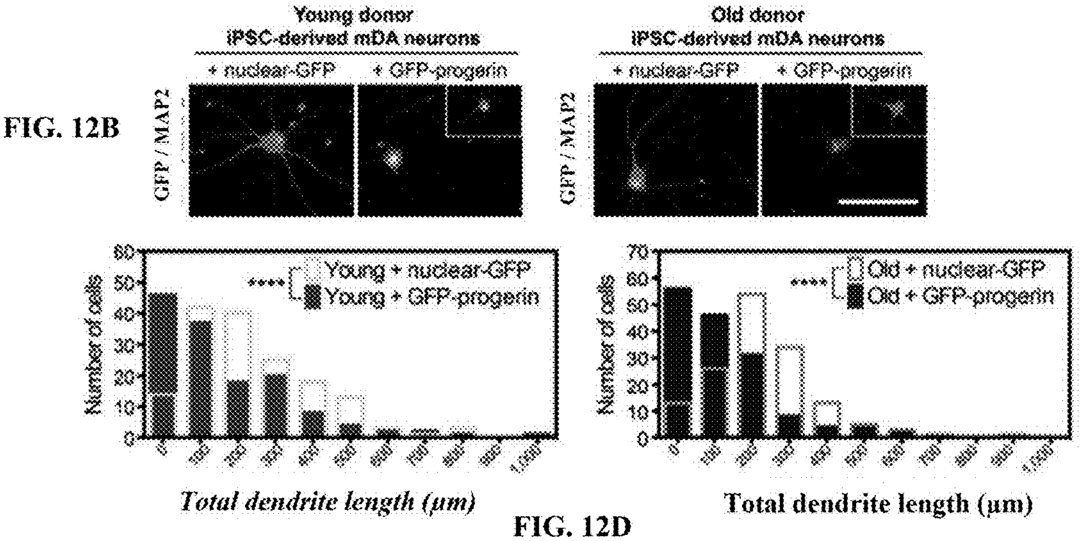
FIG. 12D
FIG. 12C
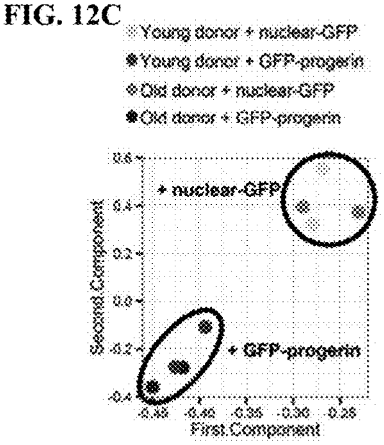
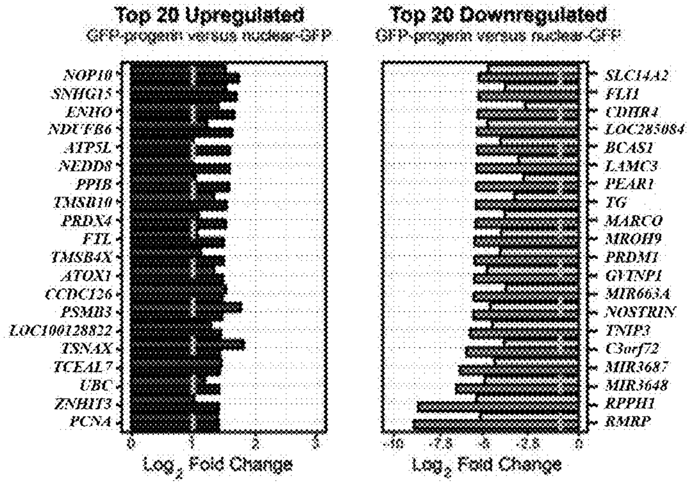
FIG. 12E
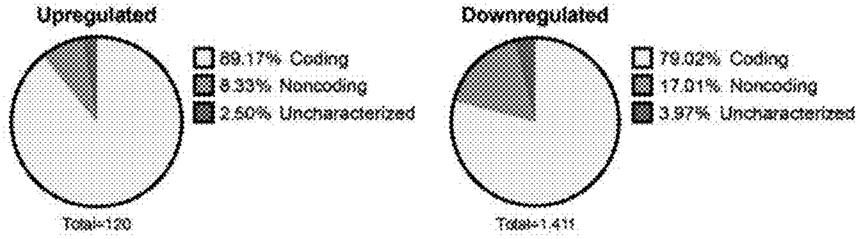

FIG. 13A
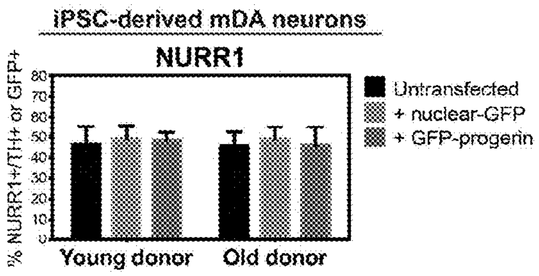
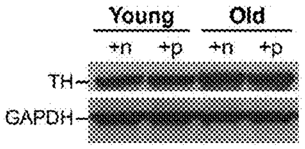
FIG. 13B
FIG. 13C
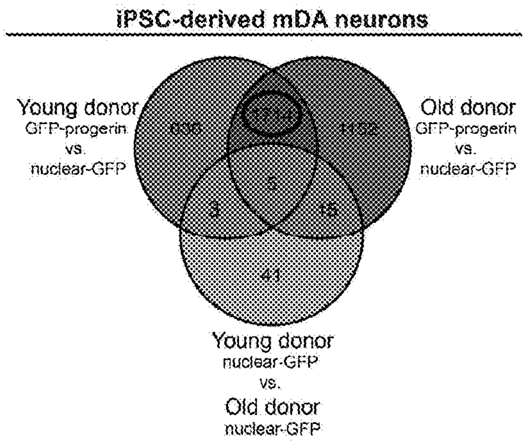

AGE-MODIFIED CELLS AND METHODS FOR MAKING AGE-MODIFIED CELLS

CROSS-REFERENCE TO RELATED APPLICATIONS

This application is a continuation of International Patent Application No. PCT/US2014/034435, filed Apr. 16, 2014, and claims priority to U.S. Provisional Application No. 61/812,464, filed on Apr. 16, 2013, and U.S. Provisional Application No. 61/907,262, filed on Nov. 21, 2013, to each of which priority is claimed and the contents of each which are incorporated herein in their entireties.

GRANT INFORMATION

The work described in this disclosure was funded in part by an NSF fellowship, DGE-1144470. The U.S. government may have certain rights in this disclosure.

SEQUENCE LISTING

The instant application contains a Sequence Listing which has been submitted electronically in ASCII format and is hereby incorporated by reference in its entirety. Said ASCII copy, created on Dec. 22, 2015, is named 072734.0330_SL.txt and is 11,456 bytes in size.

TECHNICAL FIELD

The present disclosure relates, generally, to the treatment and study of disorders and/or diseases, including late-onset disorders and/or diseases. More specifically, the present disclosure concerns the application of methods for accelerating the maturation of cells, which can be used both clinically as well as in basic research. Provided are cells exhibiting one or more chronological markers and methods for inducing such markers in a cell, such as a somatic cell, a stem cell, and/or a stem cell derived somatic cell, including an induced pluripotent stem cell (iPSC)-derived somatic cell. Treatment of such cells, including cells that are reversed in cellular age, with progerin or a progerin-like protein can induce one or more chronological markers, which chronological markers constitute, collectively, one or more marker signatures. Thus, provided herein are age appropriate cells that can be used therapeutically for the treatment of disorders and diseases and as model systems for studying late-onset disorders and/or diseases. Additionally, the present disclosure also relates to a cell with modified age by contacting with progerin or another progerin-like protein.

BACKGROUND OF THE DISCLOSURE

Late-onset disorders and/or diseases can occur in a variety of physiological systems. For example, neurodegenerative disorders such as Parkinson's disease (PD) or Alzheimer's disease (AD) are becoming a growing burden to society. Higher life expectancies have led to an explosion of the number of individuals diagnosed with those currently incurable and in many cases untreatable disorders. This trend is expected to escalate, as it is estimated that the afflicted population, individuals over 60 years of age, will represent 21.8% of the total world population reaching 2 billion people by 2050. Lutz et al., *Nature* 451:716-719 (2008).

Age per se is believed by many to be a significant risk factor for neurodegenerative diseases, and it is estimated that, for example, the cases of AD in the U.S. will more than triple from 4 million in 2010 to nearly 14 million by 2050. Hebert et al., *Neurology* 80(19):1778-83 (2013). Similar increases in incidence are expected for PD over the next 30 years. Dorsey et al., *Neurology* 68:384-386 (2007). In parallel, therapies for age related disorders such as AD and PD are being developed at an excruciatingly slow rate. Only symptomatic relief is available, limited in terms of both the symptoms treated and the duration of its effectiveness, highlighting the need for novel preventive and therapeutic approaches.

Late-onset neurodegenerative disorders such as Parkinson's disease (PD) are becoming a growing burden to society due to the gradual increase in life expectancy. The incidence of PD will likely continue to rise, as it is estimated that by 2050 21.8% of the projected world population (approximately 2 billion people) will be over 60 years of age (Lutz et al., *Nature* 451:716-719 (2008).

The use of induced pluripotent stem cell (iPSC) technology where patient-derived skin cells can be reprogrammed back to a pluripotent state and then further differentiated into disease-relevant cell types presents new opportunities for modeling and potentially treating currently intractable human disorders (Bellin et al., *Nat Rev Mol Cell Biol* 13, 713-726 (2012). However, there is a concern as to how well iPSC-derived cells can model late-onset diseases where patients do not develop symptoms until later in life, implicating age as a necessary component to disease progression.

Several iPSC studies have demonstrated a loss of particular age-associated features during iPSC induction (reviewed in Freije and López-Otin, *Curr Opin Cell Biol* 24, 757-764 (2012); Mahmoudi and Brunet, *Curr Opin Cell Biol* 24, 744-756 (2012)). For instance, there is evidence for changes in age-associated features such as an increase in telomere length (Agarwal et al., *Nature* 464:292-296 (2010); Marion et al., *Cell Stem Cell* 141-154 (2009)), mitochondrial fitness (Prigione et al., *Stem Cells* 721-733 (2010); Suhr et al., *PloS One* e14095 (2010)) and loss of senescence markers (Lapasset et al., *Genes Dev* 25: 2248-2253, 2011) in iPSCs derived from old donors, suggesting that rejuvenation takes place during old donor cell reprogramming. In addition to the apparent loss of age-associated features in iPSCs, as compared to their primary somatic cell source, another advantage of using iPS cells in progerin aging of iPS derived cells of the present disclosures is the resulting mature phenotype. In contrast, directed differentiation of human pluripotent stem cells (hPSCs) is known to yield immature, embryonic-like cell types, which lack maturation markers and the ability to display late-onset disease phenotypes. In fact, without progerin-induced aging, these immature iPSC-derived cells often require months of in vitro or in vivo maturation to establish robust functional properties of their particular cell type (Liu et al., *Curr Opin Cell Biol* 24:765-774 (2012); Saha & Jaenisch, *Cell Stem Cell* 5:584-595 (2009).

Protracted differentiation is thought to reflect the slow timing of human development. For example, human midbrain dopamine (mDA) neurons, the cell type predominantly affected in PD, require months of culture to develop mature physiological behaviors in vitro and months of in vivo maturation to rescue dopamine deficits in animal models of PD (Isacson et al., *Trends Neurosci* 20:477-482 (1997); Kriks et al., *Nature* 480:547-551 (2011)). Furthermore, based on the BRAIN-span atlas of the developing human brain (brainspan.org), gene expression data from hPSC-derived neural cells match the transcriptome of first trimester embryos, a stage believed to be too early to model late-onset disorders. These in vitro differentiation data indicated a species-specific intrinsic "clock-like" maturation process that prevented the rapid generation of mature or aged cells posing a major challenge for human iPSC-based modeling of late-onset neurodegenerative disorders such as PD.

A problem in addressing the global aspects of aging and rejuvenation during cell reprogramming and differentiation is the identification of markers that reliably predict the chronological age of the somatic cell donor and the corresponding cellular age of iPSC derivatives.

Induced pluripotent stem cells (iPSCs) have been proposed to be useful for modeling human disease. For example, iPSC technology has been used to study early-onset disorders such as familial dysautonomia or Herpes Simplex encephalitis. Lee et al., *Nat Biotechnol* 30:1244-1248 (2012); Lee et al., *Nature* 461:402-406 (2009); and Lafaille et al., *Nature* 491:769-773 (2012). Discovery of the disease mechanisms for both disorders and high throughput drug screening enabled a human iPSC-based disease model on which screened drug candidates could be further tested.

Despite early progress in modeling early-onset genetic disorders, fundamental questions remain as to how well iPSC-based approaches can model late-onset disorders such as Parkinson's disease (PD) given the embryonic nature of iPSC-derived midbrain dopamine (mDA) neurons. Lee & Studer, *Nat Methods* 7:25-27 (2010); Saha & Jaenisch, *Cell Stem Cell* 5:584-595 (2009); and Liu et al., *Curr Opin Cell Biol* 24:765-774 (2012). Late-onset disorders such as PD take decades to develop without any signs of the disease at early stages of life. Indeed current studies modeling genetic or sporadic forms of PD using iPSC technology show no observed phenotype or display relatively subtle biochemical or morphological changes without recreating the severe degenerative pathology characteristic of the disease. Soldner et al., *Cell* 146:318-331 (2011); Soldner et al., *Cell* 136: 964-977 (2009); Nguyen et al., *Cell Stem Cell* 8:267-280 (2011); Seibler et al., *J Neurosci* 31:5970-5976 (2011); and Cooper et al., *Sci Transl Med* 4:141ra190 (2012).

The ability to measure and manipulate age in cells differentiated from iPSCs represents a fundamental challenge in pluripotent stem cell research that remains unresolved to date. There has been considerable progress in directing cell fate into the various derivatives of all three germ layers; however, there has been no technology to switch the age of a given cell type on demand from embryonic to neonatal, adult or aged status. This remains a major impediment in the field as illustrated by the persistent failure to generate hiPSC-derived adult-like hematopoietic stem cells, fully functional cardiomyocytes, or mature pancreatic islets and the general inability to derive aged cell types that are age-appropriate and/or stage-appropriate for modeling late-onset diseases.

iPSC models of late-onset disorders such as PD do not adequately reflect the severe degenerative pathology of the disease. Thus, new methods to model late-onset neurodegenerative disorders are needed. Specifically, new methods to generate aged cells that more closely resemble the age of the patient using iPSC technology would be very useful in the quest for effective treatments for late-onset diseases, particularly degenerative ones and more specifically neurodegenerative ones.

Additionally, an ability to accelerate maturation of cells would be useful in providing supplies of age-appropriate cells at a rapid pace, whether for research or therapy.

SUMMARY OF THE DISCLOSURE

Disclosed are methods for producing a cell exhibiting at least one chronological marker, said method comprising:

contacting a cell that is deficient in said one or more chronological markers with a progerin-like protein in an amount and for a period of time sufficient to induce the production of said at least one chronological marker. In some embodiments, the cell can be a stem cell or a somatic cell. In a more particular embodiment, the cell can be an iPSC-derived cell. In a still more particular embodiment the iPSC-derived cell is a neuron.

In some embodiments, the at least one chronological marker is selected from the group consisting of an age-associated marker, a maturation-associated marker, and a disease-associated marker.

Disclosed is also a cell exhibiting at least one chronological marker induced by contacting the cell with an exogenous progerin-like protein in an amount and for a period of time sufficient to induce said at least one chronological marker.

In some embodiments the amount of exogenous progerin-like protein is within the range from about 10 times to about 5000 times of the level of expression of endogenous progerin or from about 40 times to about 500 times of the level of expression of endogenous progerin.

In some embodiments, the cell is a somatic cell selected from the group consisting of a fibroblast cell, a liver cell, a heart cell, a CNS cell, a PNS cell, a kidney cell, a lung cell, a hematopoietic cell, a pancreatic beta cell, a bone marrow cell, an osteoblast cell, an osteoclast cell, an endothelial cell. In some embodiments, the cell is selected from the group consisting of a neural progenitor, a neuron and a glial cell.

1. The cell according to claim 22 wherein said CNS cell is a midbrain dopamine (mDA) neuron cell.

2. The cell according to claim 14 wherein said at least one chronological marker is selected from the group consisting of an age-associated marker, a maturation-associated marker, and a disease-associated marker.

3. The cell according to claim 14 wherein said at least one chronological marker is an age-associated marker selected from Table 2 or Table 3.

Disclosed is also a cell having an LMNA RNA splicing pattern that has been modified to express an amount of an endogenous progerin-like protein for a period of time sufficient to induce at least one chronological marker in said cells.

In some embodiments, the splicing pattern is modified by transfecting the cell with a vector. Such as an antisense oligonucleotide, a small interfering RNA, a short hairpin RNA, a microRNA, an adeno-associated virus, a lentivirus, a Sendai virus, a retrovirus, and a DNA plasmid.

Disclosed are also methods for drug screening, comprising contacting an age-modified cell with a candidate drug and detecting an alteration in at least one of the survival, biological activity, morphology or structure of the cell, wherein said age-modified cell exhibits at least one chronological marker induced by contacting the cell with an exogenous progerin-like protein in an amount and for a period of time sufficient to induce said at least one chronological marker in said cell. In some embodiments, the screening method comprises contacting an age-modified cell with a candidate drug and detecting an alteration in at least one of the survival, biological activity, structure or morphology of the cell, wherein said age-modified cell has an LMNA RNA splicing pattern that has been modified to express an amount of an endogenous progerin-like protein for a period of time sufficient to induce at least one chronological marker in said cell.

In some embodiments, contacting the cell with a progerin-like protein accelerates the aging and/or maturation of the cell. By controlling this process, the age of a cell can be selected to model late-onset diseases, especially those diseases that otherwise cannot be studied adequately.

The thus produced cells can be used in variety of applications, including, but not limited, disease modeling, drug screening, and therapeutics.

In other embodiments, the present disclosure provides methods for producing an age-appropriate somatic cell comprising contacting a cell culture with a progerin-like protein, wherein said cell culture has at least one first chronological marker signature (e.g., one found in a young or immature cell), and thereby inducing an age-appropriate somatic cell that exhibits at least one second chronological marker signature (e.g., one found in an old or mature cell). In further embodiments, methods of the present disclosure can be applied to produce an age-appropriate somatic cell comprising contacting a primary somatic cell with progerin or a progerin-like protein, wherein the primary somatic cell culture has at least one first disease marker signature, wherein the age-appropriate somatic cell culture that is produced exhibits at least one second disease marker signature. The chronological marker signature can comprise one or more chronological markers.

In one embodiment, the neuronal cell is a midbrain dopamine cell. In one embodiment, the neuronal cell culture is a PARKIN neuronal cell culture. In one embodiment, the neuronal cell culture is a LRRK2 neuronal cell.

BRIEF DESCRIPTION OF THE DRAWINGS

FIG. 5G discloses SEQ ID NOS 23 (top two sequences) and 24 (bottom two sequences).

FIG. 7A-7E presents exemplary data showing that progerin overexpression induces a subset of the fibroblast age-associated signature in iPSC-mDA neurons derived from both young and old donors. (A) Modified-RNA was transfected into iPSC-derived mDA neurons on five consecutive days prior to analysis on day 6. (B) Western blot analysis of transgene expression. A GFP band at 100 kDA denotes the GFP progerin fusion protein while a GFP band at 27 kDA represents the nuclear-GFP transgene. All lamin A isoforms including the transgene were recognized by a single antibody. Note that progerin overexpression levels exceed endogenous lamin A levels (arrows). iPSC-derived mDA neurons do not appear to express detectable levels of progerin protein endogenously. n, nuclear-GFP; p, GFP-progerin. (C) Progerin overexpression enhances nuclear folding and blebbing (as seen by lamin B2, pink) and increases DNA damage accumulation (γH2AX) in both young and old donor-derived iPSC-mDA neurons. Percentages indicate the proportion of cells with enhanced nuclear folding and/or blebbing or the proportion of cells with >3 enlarged γH2AX foci. (D) Flow cytometry analysis of mitochondrial superoxide levels (MitoSOX) demonstrates increased mitochondrial dysfunction with progerin overexpression. n=3 independent RNA transfections of iPSC-derived mDA neurons derived from independent iPSC clones. (E) Quantification of immunocytochemistry for LAP2α, H3K9me3 and HP1γ shows no difference between iPSC-mDA neurons transfected with GFP-progerin or nuclear-GFP, unlike the phenotype observed in iPSC-derived fibroblasts (see FIG. 3). Fluorescence intensities were normalized to the intensities observed in nuclear-GFP-treated cells. $*p<0.05$ according to Student's t tests (D). Bar graphs represent mean±SEM. Scale bars: 10 μm (C, bottom), 25 μm (C, top).

FIG. 9A-9E presents exemplary data of global "age" marker profiles (5-mC, 5-hmC and RNA-Seq analyses) following progerin overexpression. Hierarchical clustering of 5-mC (A) and 5-hmC (B) methylation signatures from aged-matched fibroblasts and iPSC show clear separation between fibroblasts and iPSC with sub-classification by age.

Panel C shows hierarchical clustering of iPSC-mDA expressing progerin and matched GFP controls indicate a distinct age-associated transcriptome profile. Panels D and E show genome wide view of the 5-mC and 5-hmC differential methylation in iPSC vs. primary fibroblasts indicating increased methylation in iPSC.

Figure 10:
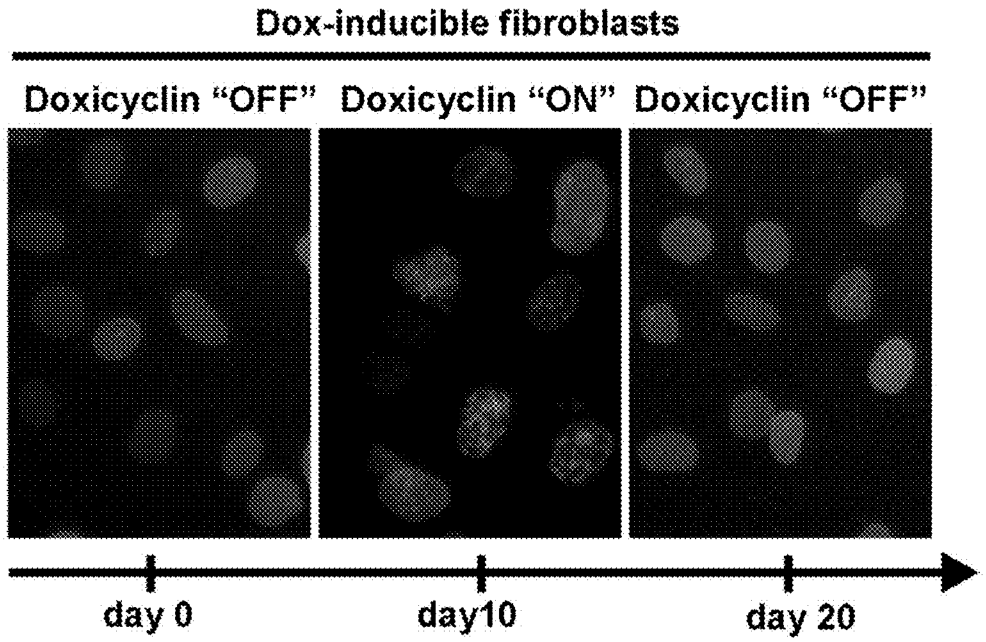

FIG. 10 presents exemplary data showing the reversibility of progerin-induced nuclear changes. The panels show that progerin-induced changes in nuclear morphology are reversed within 10 days following re-addition of doxycycline in a doxycycline (dox)-inducible fibroblast line (Scaffidi et al, *Nat Cell Biol* 10, 452-459 (2008)).

Figure 11A:
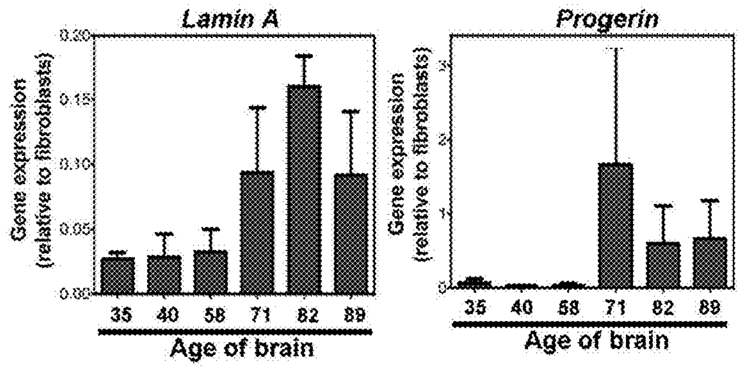
Figure 11B:
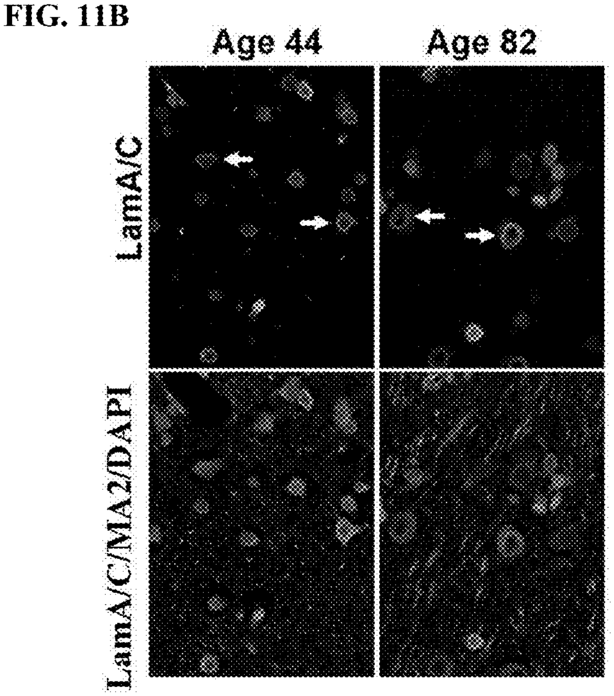
Figure 11C:
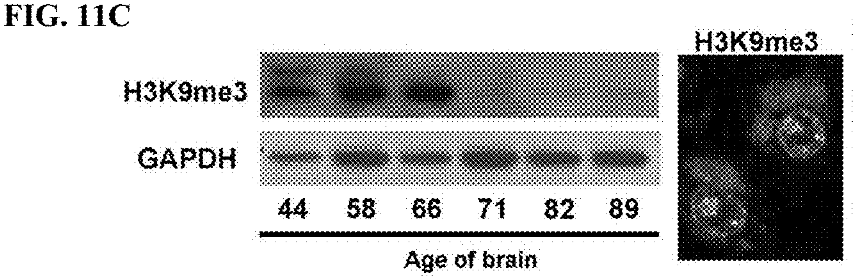

FIG. 11A-11C presents exemplary data showing the expression of lamin A and progerin in aged human brain tissue. Panel A demonstrates that both lamin A and progerin show increased mRNA expression levels in cortex tissue obtained from aged individuals. Panel B depicts the visualization of the nuclear envelope and identification of neurons in paraffin-embedded human cortex tissue by immunofluorescence for Lamin A/C and MAP2 obtained from two donors aged 44 and 82, respectively. Arrows indicate examples of MAP2-positive neurons. Panel C shows western blot analysis (left panel) of soluble tri-methylated H3K9 which indicates a dramatic change in heterochromatin organization with similar timing to lamin A and progerin upregulation. These changes may reflect a reorganization of heterochromatin into insoluble heterochromatic foci with age, as demonstrated by the right panel.

FIG. 12A-12E presents exemplary data showing that progerin overexpression elicits features consistent with neuronal aging in iPSC-derived mDA neurons. (A) Immunocytochemistry for the pan-neuronal marker TUJ1 shows a loss of the established neuronal network in day 70 iPSC-derived mDA neurons overexpressing progerin but not iPSC derived neurons overexpressing nuclear-GFP. (B) MAP2 immunocytochemistry reveals reduced intact dendrite lengths following overexpression of progerin in most but not all (inset) iPSC-mDA neurons derived from both young and old donors. Frequency distributions display total dendrite length measurements from 3 independent RNA transfections (50 cells each, non-apoptotic nuclei only). (C) Principal component analysis of RNA-seq gene expression data further corroborates the reprogramming-induced reset of age that results in the high similarity of iPSC-derived mDA neurons from both young and old donors. Progerin overexpression induces similar changes in mDA neurons independent of donor age. (D) The top 20 upregulated (left) and downregulated (right) genes in progerin-treated compared to control nuclear-GFP-treated young donor (green) and old donor (blue) iPSC-mDA neurons. Genes are ranked according to iPSC-mDA neurons derived from the old donor. Red denotes uncharacterized genes and orange denotes non-coding RNAs. Dotted line indicates the threshold for significance. (E) Pie charts representing the proportion of the significantly differentially expressed transcripts that are coding, non-coding, or uncharacterized. ****$p<0.0001$ according to Kolmogorov-Smirnov tests. Scale bars: 200 μm (A), 50 μm (B).

FIG. 13A-13D presents exemplary data showing that progerin overexpression induces a neurodegeneration-like phenotype. Characterization of mDA neuron markers following progerin overexpression is presented, arguing that progerin does not induce acute toxicity. The Venn diagram depicts the overlapping differentially expressed genes that were defined as the progerin-induced aging signature and significant gene ontology terms are listed. (A and B) The percentage of NURR1+ iPSC-derived mDA neurons (A) and the protein expression levels of TH (B) remained unchanged with transfection, indicating that progerin overexpression does not downregulate key mDA neuron proteins (a typical sign of acute toxicity). (C) Venn diagram where each colored circle indicates the number of differentially expressed genes (Fold change +/−2, $p<0.05$) between two groups. The black circle indicates the overlapping "aging signature" that was further analyzed. (D) The significant gene ontology terms that are enriched in nuclear-GFP-treated or GFP progerin-treated iPSC-derived mDA neurons (left to right). Bar graph represents mean±SEM.

FIG. 14A-14G presents exemplary data showing that progerin overexpression reveals disease-specific phenotypes in vitro in iPSC-based models of genetic PD. (A and B) Quantification of NURR1+ cells (A) and western blot analysis of TH protein levels (B) do not reveal significant differences with transfection of GFP-progerin modified-RNA. n, nuclear-GFP; p, GFP-progerin. Numbers below the western blot indicate the ratio of GFP progerin: nuclear-GFP expression of TH normalized to GAPDH. (C) Analysis of GFP+ cells undergoing cell death following RNA transfection as identified by their condensed nuclear morphologies. Images display a representative example of cleaved caspase-3 immunocytochemistry in cells treated with progerin. (D) Immunocytochemistry for the dendrite marker MAP2. (E) Quantification of total dendrite lengths per GFP+ neuron shows accelerated dendrite shortening in PD mutant iPSC-derived mDA neurons compared to apparently healthy controls (C1-4) in response to progerin overexpression. (F and G) Western blot analysis of AKT pathway signaling (F) demonstrates genotype-specific responses to progerin overexpression. Quantification of phospho-specific bands (G) was normalized to total protein before taking the ratio of the levels expressed with progerin treatment to nuclear-GFP treatment. Dotted line indicates an equal amount of phospho protein in both treatment conditions. Quantification represents 3 independent cell isolates for each genotype. *$p<0.05$,  $p<0.01$, * $p<0.001$ according to one-way ANOVA with Dunnett's tests (n=3 independent differentiations and modified-RNA transfections in all cases). Bar graphs represent mean±SEM. n, nuclear-GFP; p, GFP-progerin; C1-4, lines derived from apparently healthy donors; (R), iPSC derived using retroviral factors; (S), iPSC derived using Sendai viral factors. Scale bars: 25 μm.

FIG. 15A-15E presents exemplary data showing the differentiation of PD mutant iPSCs into mDA neurons and characterization of additional PD patients. Mutation analysis of PINK1 and Parkin mutations as well as immunocytochemical analysis of iPSC-derived mDA neurons is presented, demonstrating that PD iPSCs differentiate with the same capacity as healthy donor iPSCs. (A) Sequencing for the homozygous PINK1 c.1366C>T and PARK2 c.1072delT mutations found in the PD mutant iPSCs but not in apparently healthy control iPSCs. (B) Immunocytochemistry at day 13 of differentiation demonstrated no differences between healthy donors and PD patients in the conversion of OCT4+ iPSCs to FOXA2+/LMX1A+ mDA floorplate precursors. (C) Further differentiation of precursors to post-mitotic mDA neurons was unaffected in PD mutant cells. n=at least 3 independent differentiations. (D) Western blot analysis of AKT pathway signaling in an additional PD patient with a heterozygous mutation in Parkin (p.R275W). Numbers below the blots indicate the ratio of p-AKT (GFP-progerin) to p-AKT (nuclear-GFP). n, nuclear-GFP; p, GFP-progerin. n.s. not significant, *$p<0.05$ according to Student's t tests. Bar graph represents mean±SEM. Scale bars: 50 μm.

FIG. 16A-16G presents exemplary data showing that long-term progerin overexpression in vivo reveals a severe degenerative phenotype in PD mutant cells. (A) Schematic illustration of the transplantation studies into 6-OHDA lesioned Parkinsonian mice. B) Rotational behavior analysis of lesioned mice transplanted with control or PD mutant iPSC-derived mDA neurons expressing hSyn::nuclear-GFP or hSyn::GFP-progerin. Mice were lesioned and tested for amphetamine-induced rotation behavior twice prior to grafting. Dotted line indicates threshold for successful lesioning. Pink symbols identify successfully lesioned animals that did not show recovery. n=3-5 animals per treatment group. (C) Assessment at 3 months post-transplant revealed a dramatic loss of TH+mDA neurons in PD mutants overexpressing progerin that was observed to a much lesser degree with the control transfection or in apparently healthy cells. (D) Quantification of the percentage of GFP+ cells that are TH+. Data are presented as mean±SEM. n=3 mice per condition. (E-G) Ultrastructural analysis 6 months after transplantation revealed an accumulation of neuromelanin with lipofuscin deposits (E, yellow arrowheads) in grafts with progerin overexpression. Strikingly, the PINK1 mutant graft with progerin displayed enlarged mitochondria (F, compare representative mitochondria indicated by orange arrows in +nuclear GFP and +GFP-progerin groups) while the Parkin mutant graft with progerin had large multilamellar bodies (G, pink arrows). These phenotypes were not observed in any other treatment groups. Asterisks in (E) and (G) indicate a fibrillar bodies. *$p<0.05$, ** $p<0.01$ according to Student's t-tests. Bar graph represents mean±SEM. Scale bars: 200 μm (C), 500 nm (E-G).

FIG. 17A-17F presents exemplary data showing the characterization of xenografts and transplanted iPSC-derived mDA neurons. (A) Immunocytochemistry for NURR1 and TH in iPSC-mDA neurons replated in vitro and fixed 1-day after transplant. At least 50% of cells already expressed the synapsin-driven transgene at this time point. (B) Immunohistochemistry for TH and GFP at 6 months post transplant demonstrates a dramatic loss of TH+PD iPSC-derived mDA neurons when progerin is overexpressed. This pattern of TH loss in controls and PD mutants is similar to what was observed at 3 months post transplant. Dotted line defines the graft. Asterisks denote the corpus callosum. Insets show a representative GFP+ nucleus. (C and D) Ultrastructural analysis by transmission electron microscopy (EM). Representative (C) TH+ dendrites and (D) GFP+ nuclei are outlined and each labeled with a D or N, respectively. Number at bottom left represents the average number of TH-immunogold particles per μm2. Asterisk identifies a fibrillar body. (E) Quantification of neuromelanin deposits from EM analysis. Ten 50 μm2 regions were analyzed per animal. (F) Quantification of the area of 25 mitochondria in PINK1-Q456X animals from EM analysis. *$p<0.001$ **$p<0.0001$ according to Student's t tests. Bar graphs represent mean±SEM. Scale bars: 50 μm (A), 400 μm (B), 500 nm (C), 2 μm (D).

Figure 18:
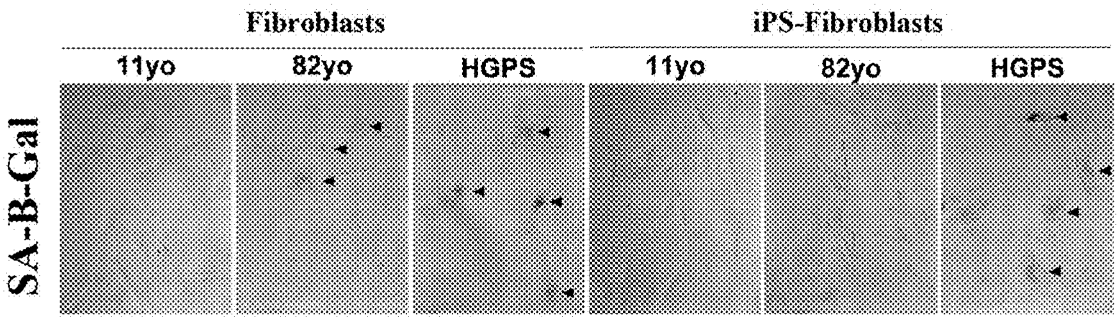

FIG. 18 presents exemplary data of senescence marker SA-βGal in primary fibroblasts and iPSC-derived fibroblasts from an 11 year old donor individual, an 82 year old donor individual, and a patient with HGPS.

Figure 19:
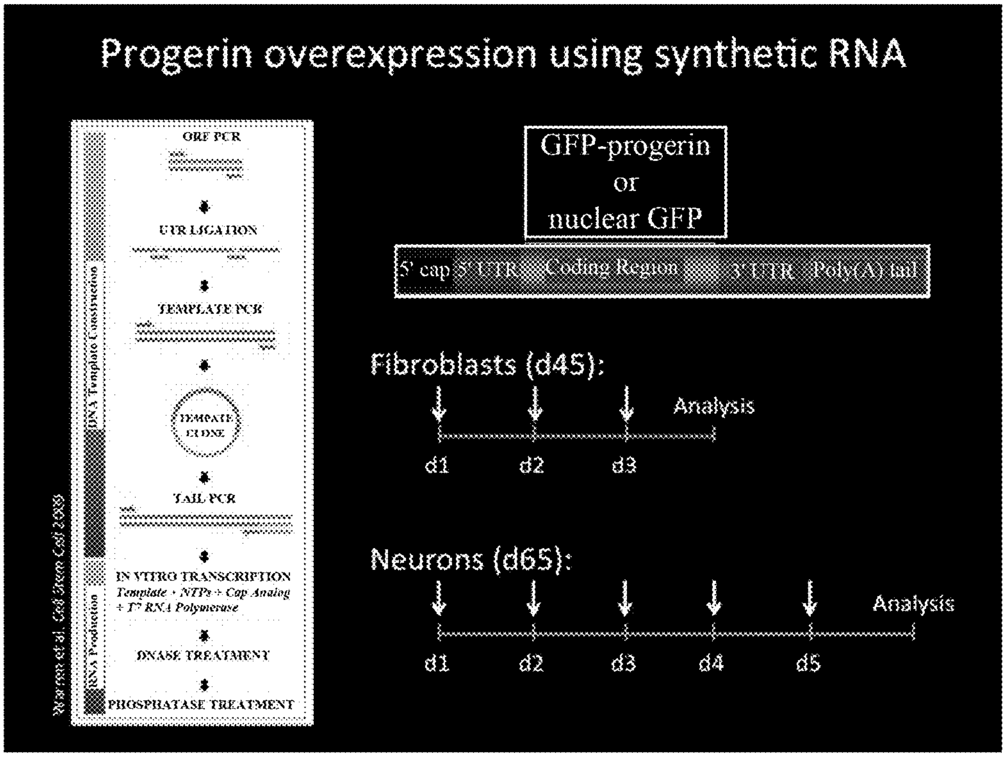

FIG. 19 presents schematic diagrams describing the expression of progerin using synthetic mRNA technology. The schematic on the left is from Mandal & Rossi, *Nat Protoc* 8:568-582 (2013). The schematic on the right shows the experiment protocol used in the present application, which describes that iPSC-derived fibroblasts were treated for 3 days while iPSC-derived mDA neurons were treated for 5 days with modified-RNA expressing either nuclear-GFP or GFP-progerin.

DETAILED DESCRIPTION

The present disclosure relates, generally, to cell therapy for the treatment of disease and to cell-based systems for modeling of disorders and/or diseases, in particular late-onset disorders and/or diseases. More specifically, provided herein are somatic cells, and methods for producing such cells, which may be primary cells (as defined below) or may be derived from undifferentiated (stem) cells, such as induced pluripotent stem cells (iPSCs), embryonic stem cells or stem cells collected from human or animal subjects. The somatic cells exhibit one or more markers that are characteristic of cellular age, maturation, and/or disease as can be confirmed by detecting one or more intracellular or morphologic markers and/or be detecting the absence of one or more intracellular markers including one or more markers that constitute an intracellular chronological marker signature.

The cells and methods for producing those cells, which are disclosed herein, are based upon the discovery that induced pluripotent stem cells (iPSCs) that result from the reprogramming or de-differentiation of a primary somatic cell have been observed to lose one or more markers that are characteristic of cellular age, maturation, and/or disease (Freije, J. M., and Lopez-Otin, C. (2012). Current Opinion in Cell Biology 24, 757-764) and that such iPSCs can be made to express one or more markers that are characteristic of cellular age, maturation, and/or disease by contacting the iPSCs, before or after differentiation to a desired cell type, with a progerin-like protein. Cells that are produced by the differentiation of iPSC, before or after contacting with a progerin-like protein, and, thereby, are made to exhibit one or more chronological marker signatures. Such "age-appropriate" cells can be used in methods for the treatment of a disorder and/or disease and can be used as in vitro model systems for the study of a disorder and/or disease, including a late-onset disorder and/or disease.

Conventional reprogramming of somatic cells to induced pluripotent stem cells (iPSCs) resets their phenotype back to an embryonic age, and thus presents a significant hurdle for modeling late-onset disorders. In addition, stem cells collected from human subjects and somatic cells derived from such stem cells are also generally devoid of age and often also of disease markers in the case of late-onset diseases. As described herein, methods are disclosed for inducing appropriate chronological marker signatures in stem cell-derived somatic cells including without limitation human iPSC-derived lineages and thus generating age-appropriate cell cultures suitable as disease models. Where possible to grow somatic cells in culture, such disease models can be developed by inducing aging chronologic marker signatures in somatic cells (not necessarily derived by induced differentiation of stem cells) that express a "young" marker signature. This strategy can be applied to cell cultures derived from a patient with a late-onset disease and/or disorder including, but not limited to a neurodegenerative disease, such as Alzheimer's disease (AD) or Parkinson's disease (PD), a cardiomyocyte-related disease, a pancreatic disease, and/or a hematopoietic disease, to derive age-appropriate cell cultures that more accurately represent patient age and thus the disease state. Methods of the present disclosure can also be applied to cells utilized for drug screening or any other experiment relevant to late-onset disease using these aged iPSC derived cells. For example, drug screening using iPSC derived cells not involving age modification has been used to screen drugs for ALS (Yang Y. M. et al., 2013 Cell Stem Cell 12, 713-726). iPSC-derived cells for the diseases mentioned above that have undergone progerin-induced aging can also be used for drug screening.

The disclosed methods involve the exposure of somatic cells such as cells of iPSC lineage to progerin, or other progerin-like protein, and its capacity to induce accelerated aging of cells in culture. The disclosed methods also relate to the exposure of somatic cells to a progerin-like protein to accelerate the maturation of these cells in culture. The data presented herein demonstrate that contacting with a progerin-like protein to iPSC-derived cell cultures (e.g., iPS cell-derived fibroblasts and iPS cell-derived neurons) induces one or more chronological markers that constitute one or more chronological marker signatures and other characteristics of an age-appropriate cell, such as a mature cell and/or an old cell.

In some embodiments, the present disclosure relates to cells with a long lifespan in vivo which are typically not quickly replenished, if at all, once damaged or diseased, such as neurons and cardiomyocytes, and to methods to obtain such cells at an aged state. These cells, when cultured in vitro, usually need long culture times to exhibit aging and/or maturation markers that represent their counterparts in vivo. Such procedures, when available, are protracted and have high cost. In some embodiments, the present disclosure relates to methods of contacting such cells with a progerin-like protein in vitro to accelerate their maturation or aging, or both, and thereby to provide an age-appropriate cell. In some embodiments, these cells can be used to model late-onset diseases, such as neurodegenerative diseases, atherosclerosis and other chronic metabolic diseases.

In some embodiments, the present disclosure relates to controlled maturation and/or aging of mammalian cells in a cell culture by contacting such cells to a progerin-like protein. Used alone, or in combination with other reagents (such as cell differentiation protocols for iPSC cells), methods by the present disclosure grant the ability to accelerate cell maturation and/or aging at a controlled speed which can be manipulated by adjusting the dose of the progerin-like protein that the cells are contacted with. For example, the maturation and/or aging of cells by methods of the present disclosure can be slowed by reducing the dose of the progerin-like protein, reducing the time of exposure or reducing the potency of the protein. Alternatively, progerin-like protein exposure can be halted by removing the progerin-like protein or by introducing an inhibitory factor of the protein (e.g., RNA silencing, mAb, etc.). The matured cells can be subjected to additional procedures or be used in experiments where use of mature cells is important or in cell therapy.

These and other aspects of the present disclosure can be better understood by reference to the following non-limiting definitions.

DEFINITIONS

The terms defined below shall have the meanings ascribed to them unless the context clearly indicates otherwise. The defined terms shall include cognates thereof.

As used herein, the term "patient" refers to any animal (e.g., a mammal), including, but not limited to, humans, non-human primates, rodents, and the like. As used herein, the terms "subject" and "patient" are interchangeable.

As used herein, the term "young" in reference to an individual refers to an early chronological age, which for humans refers to age in years. The term "young" in reference to a cell refers to a cell state such as an immature cell, such as a young iPSC-derived somatic cell, i.e., a cell displaying a marker signature of cells isolated from young donors regardless of the age of the donor of the original primary cell that gave rise to the iPSC. This is to be contrasted with "old" iPSC-derived or indeed any somatic cell which displays a marker signature of cells isolated from old donors. An example of an old iPSC derived somatic cell is that produced when iPSC-derived somatic cell is contacted by progerin (again, regardless of the age of the donor of the primary cell that gave rise to the iPSC) following reprogramming. A young cell may also refer to a population of "young cells" such as young primary cells derived from a donor of young chronological age as in "young primary fibroblasts."

As used herein, the term "old" in reference to an individual refers to chronological age, which for humans refers to age in years. The term "old" in reference to a cell refers to a cell state wherein the cell expresses one or more chronological markers associated with aged cells, or primary somatic cells from old donors. An old cell may also refer to a population of "old cells" such as old primary cells derived from a donor of old chronological age as in "old primary fibroblasts."

As used herein, the term "donor individual" or "donor" refers to any organism, human or non-human, from which cells were obtained to provide a primary cell culture. The donor individual may be of any age, and may be non-diseased or diseased. The donor may provide cells for use in the present methods, by providing biological samples, including a biopsy, a skin biopsy, blood cells, and the like.

The term "disease," as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent or acquired defects of the organism (as genetic or epigenetic anomalies); and/or iv) combinations of these factors.

As used herein, the term "late-onset disease" refers to a disease or medical condition of a patient manifesting as a clinical condition in middle age and old age patients. Such that a late-onset disease may include but not limited to degenerative, such as neurodegenerative diseases, such as Parkinson's disease (PD), amyotrophic lateral sclerosis, Alzheimer's, Huntington's disease, and diseases of other lineages including cardiac hypertrophy, cardiac fibrosis, Type II diabetes, age-related macular degeneration, cancers, including for example breast cancers, colon cancers, and ovarian cancers, familial adenomatous polyposis (FAP), heart disease, and the like. See, Wright et al., *Trends Genet* 19:97-106 (2003), incorporated by reference.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

The term "deficient" as used herein refers to a cell which either does not express the mRNA of a gene, a protein product of a gene, or both (i.e., devoid of such expressions), or express them at a reduced level.

As used herein, the term "neuronal maturation medium" or "BAGCT medium" refers to a culture medium comprising N2 medium, further comprising brain-derived neurotrophic factor (BDNF), ascorbic acid (AA), glial cell line-derived neurotrophic factor, dibutyryl cAMP and transforming growth factor type 133 for differentiating midbrain fate FOXA2/LMX1A+ dopamine (DA) neurons.

As used herein, the terms "purified," "to purify," "purification," "isolated," "to isolate," "isolation," and grammatical equivalents thereof as used herein, refer to the reduction in the amount of at least one contaminant from a sample. For example, a cell type is purified by at least 10%, preferably by at least 30%, more preferably by at least 50%, yet more preferably by at least 75%, and most preferably by at least 90%, reduction in the amount of undesirable cell types. Thus purification of a cell type results in"enrichment," i.e., an increase in the amount, of the cell type in the cell culture.

As used herein, the term "progerin" refers to a truncated or otherwise modified version of lamin A protein involved in Hutchinson-Gilford progeria syndrome (HGPS). Numerous mutations of the lamin A gene (LMNA) can lead to high expression levels of progerin which cause HGPS, including, but not limited to, C1824T, G433A, G1968A, and G1821A. Progerin can also be transcribed in healthy individuals via activation of a cryptic splice site in the lamin A gene such that only a truncated molecule is expressed.

As used herein, the term "progerin-like protein" encompasses progerin as defined above as well as another polypeptide that is a truncated or otherwise modified (mutated) version of lamin A protein. For example, the truncation can comprise a deletion of the C-terminal cleavage site. Such a defective lamin A protein is not properly processed and therefore does not properly integrate into the nuclear lamina; it causes morphological, structural, molecular or cellular abnormalities to a cell that are functionally similar to the effects of progerin. These abnormalities include, but are not limited to, nuclear accumulation of farnesylated protein trapped at the nuclear envelope, disfigurement of the nucleus, and disruption of the nucleoplasmic and/or cytoplasmic scaffold structure. With respect to stem-cell derived somatic cells, the effects of a progerin-like protein include without limitation (depending on the type of cells) induction of age-related phenotypes affecting nuclear morphology and expression of nuclear organization proteins as well as markers of heterochromatin, DNA damage and reactive oxygen species, dendrite degeneration, the formation of age-associated neuromelanin, AKT deregulation, selective reduction in the number of TH-positive neurons, and ultrastructural evidence of mitochondrial swelling and inclusion bodies. In short, progerin-like protein is a variant of lamin A that has one or more of the effects of progerin as illustrated in this paragraph.

As used herein, the term "differentiation agent" or "differentiation inducing compound" refers to a substance, which can be a biological molecule or a small molecule or a mixture of substances which has the property of causing a stem cell to commit to a cellular pathway leading to a somatic cell. For example, such inducing compounds may include, but are not limited to, Wnt activators or SMAD inhibitors.

As used herein, the term "sonic hedgehog protein or SHH" refers to one of three proteins in the mammalian signaling pathway family called hedgehog. SHH is believed to play a role in regulating vertebrate organogenesis, such as the growth of digits on limbs and organization of the brain. Sonic hedgehog protein is thus a morphogen that diffuses to form a concentration gradient and has different effects on the cells of the developing embryo depending on its concentration. SHH may also control cell division of adult stem cells and has been implicated in development of some cancers.

As used herein, the tem). "Small Mothers against Decapentaplegic" or "SMAD" are intracellular proteins that transduce extracellular signals from transforming growth factor beta ligands to the nucleus where they activate downstream gene transcription and are members of a class of signaling molecules capable of modulating directed differentiation of stem cells.

As used herein, the term "contacting" refers to exposing the cell to a compound or substance in a manner and/or location that will allow the compound or substance to exert its activity on the cell. Contacting may be accomplished using any suitable method and may be extracellular or intracellular. For example, in one embodiment, contacting is by introducing the compound/substance intracellularly either as such or by genetically modifying the cell, such that it expresses the compound or substance. Contacting can be achieved by a variety of methods, including exposing cells to a molecule or to a vehicle containing a molecule, delivering a polynucleotide encoding for a polypeptide to the cells through transfection. Contacting may also be accomplished by adding the compound or substance to a culture of the cells so that the contacting occurs on the outer cell membrane. Contacting may also be accomplished within a given cell by the production of a recombinant protein (for example, by overexpression of an mRNA encoding progerin or a progerin-like protein) within a cell.

As used herein, the terms "reprogramming," "reprogrammed" refer to the conversion of "primary cells" or "primary differentiated cells" or "primary somatic cells" into undifferentiated cells, such as induced pluripotent stem (iPS) cells. For example, a somatic cell culture of primary cells, (e.g., for example, primary fibroblasts isolated from donors of certain ages or primary fibroblasts isolated from patients having a disease, such as Hutchinson-Gilford Progeria Syndrome (HGPS), e.g., HGPS fibroblasts, etc.), including cell lines, may be reprogrammed into induced pluripotent stem cells. Further, an age-related marker signature appearing in the primary somatic cell culture is then altered in the reprogrammed, undifferentiated cells. In some instances, disease marker signatures appearing in the differentiated somatic cell cultures (i.e., for example, HGPS marker signatures) may be absent in the converted undifferentiated cells, however the exact signature may differ between iPS cells produced from different primary somatic cell donors. Primary cells may be obtained from any source, such as from donors, i.e. a biopsy, a skin biopsy, a blood draw, and the like, cell lines, and the like.

As used herein, the term "differentiated" in reference to a somatic cell refers to a cell having a more committed cell type characteristic, such as a marker signature characteristic of its type. "Differentiated" in reference to an iPS cell-derived somatic cell refers to a cell that has at least one marker signature not present in the iPSC, for example, a marker signature of a specialized cell. As used herein, the term "inducing differentiation" refers to a process initiated by compounds that act as differentiation agents, including, but not limited to, Wnt inhibitors, sonic hedgehog proteins and/or activators, and/or SMAD inhibitor molecules. Such agents trigger or promote the largely genetically controlled differentiation process which converts an undifferentiated cell (such as an embryonic stem cell, an induced pluripotent stem cell, a primary stem cell etc.), to a committed somatic phenotype, that of a specialized cell having a more distinct form and function, which may or may not admit further differentiation. For example, induced pluripotent stem cells may be converted into iPSC-derived fibroblasts or iPSC-derived neurons, including without limitation neuron with a specific type of junction, specific range of electrical transmission rate, specific types of neurochemical production and/or secretion, etc. As used herein, the term "aging," in reference to a cell or cell population, refers to any stage during the progression from expression of a young marker signature towards an old marker signature. One example of aging is the natural aging process in a cell characterized by molecular and morphological markers associated with an aged cell, such as genomic instability, telomere shortening, loss of proteostasis, loss of heterochromatin and altered gene transcription, mitochondrial dysfunction, cellular senescence, and stem cell exhaustion. An example of induced aging is shown herein after treatment of a culture of young cells with a progerin-like protein. Aging can also encompass maturation, whereby additional molecular, physical and functional properties of an adult cell (including a chronological marker signature) are expressed. This may be induced for example with lower doses of progerin and/or lower progerin contact time periods than those required to age a cell. In fact, in one embodiment, progerin treatment of iPSC-derived neurons induced age-related markers associated with degeneration and also maturation markers such as neuromelanin accumulation, dendrite shortening, telomere shortening and other results of DNA damage, heterochromatin loss and mitochondrial stress.

As used herein, the term "accelerated cellular aging" refers to the establishment of an age-related marker signature in an iPSC-derived somatic cell characterizing a different age relative to what is created by differentiation alone, such that an "aged" iPSC-derived somatic cell is created. For example, this process can be mediated by introduction of an mRNA encoding progerin or a progerin-like protein into the iPSC-derived somatic cell and subsequent translation into a functional progerin polypeptide. Additional methods for progerin overexpression (which could be inducible) include, but are not limited to transfection with various vectors, such as adeno-associated virus, lentivirus, Sendai virus, retrovirus, DNA plasmids such that progerin expression is affected at the DNA, RNA, and/or protein level in either a transient or long-term manner. As described herein, this process induces a reprogrammed/differentiated iPSC-derived somatic cell into an aged iPSC-derived somatic cell.

As used herein, the term "chronological marker signature" refers to any intracellular structure that is characteristic of the specific age of the donor individual or of a cell such that it is sufficient to determine that state. A single marker signature may be sufficient to characterize the age of primary cells from a donor or the age phenotype of a cell (notably a cell differentiated from a stem cell that has no age characteristics of the donor individual or that has lost them such as during reprogramming and subsequent differentiation) wherein the age-related phenotype has been induced, or a profile of a plurality of different marker signatures may be evaluated to characterize the age of a donor or indeed any other cell.

As used herein, the term "marker" refers to a molecular or morphologic trait characteristic of a state of a cell and therefore useful, alone or in combination with other markers, in indicating that state A "marker" can be a "chronological marker," which includes "age-related markers" and "maturation-related markers." "Markers" can also be "disease related markers," which include "late-onset disease markers." If a single marker (or combination of markers) is sufficient in indicating the state of a cell, it constitutes a marker signature, as further explained below.

As used herein, the term "age-related marker signature" refers to any chronological marker signature (comprising one or more markers) that is characteristic of the natural aging process. A single age-related marker signature may be sufficient to characterize the age of primary cells from a donor or the phenotypic stage of cells wherein an age phenotype has been induced, or a profile of a plurality of different marker signatures may be evaluated to characterize the age of primary cells from a donor or the phenotypic stage of cells wherein an age phenotype has been induced or the phenotypic age of a cell.

As used herein, the term "maturation-related marker signature" refers to any chronological marker signature that is characteristic of the natural maturation process. A single maturation-related marker signature may be sufficient to characterize the maturation stage of primary cells or the phenotypic stage of cells wherein an age phenotype has been induced, or a profile of a plurality of different marker signature maybe evaluated to characterize the maturation stage of primary cells or the phenotypic stage of cells wherein an age phenotype has been induced.

As used herein, the term "disease-related marker signature" refers to any cellular structure (molecular or morphologic) that is characteristic of a specific disease. A single marker signature may be sufficient to characterize a disease, or a profile of a plurality of different marker signatures may need to be evaluated to characterize a disease state.

As used herein, the term "cell" refers to a single cell as well as to a population of (i.e., more than one) cells. The population may be a homogeneous population comprising one cell type, such as a population of neurons or a population of undifferentiated embryonic stem cells. Alternatively, the population may comprise more than one cell type, for example a mixed neural cell population comprising neurons and glial cells. It is not meant to limit the number of cells in a population, for example, a mixed population of cells may comprise at least one differentiated cell. In one embodiment, a mixed population may comprise at least one differentiated cell and at least one stem cell. In the present disclosure, there is no limit on the number of cell types that a cell population may comprise.

As used herein, the terms "primary cell" or "primary somatic cell" refers to a cell that is cultured directly from a subject, which can be reprogrammed for generating an undifferentiated iPSC in accordance with the methods disclosed herein and/or under the appropriate conditions, i.e. when contacted with a proper growth factor, compound, extracellular signal, intracellular signal, transfected with reprogramming genes (factors), etc. For example, a primary cell (culture) comprises a fibroblast cell, differentiated primary somatic cell, stem cell lines, and the like. In some embodiments, primary cells are isolated from patients. In some embodiments, primary cells are cell lines. In some embodiments, primary cells are stem cell lines. In some embodiments, primary cells are embryonic stem cells. In some embodiments, primary cells are isolated from sources such as from healthy volunteers, from patients, from patients having a particular disease or medical condition, regardless of clinical manifestation, i.e. patients having a certain genotype or phenotype. In some embodiments, primary cells are isolated from mammals. In some embodiments, primary cells are isolated from animals.

As used herein, the term "permissive state" in reference to a somatic cell (iPSC-derived or not) refers to a cell contacted with a progerin-like protein and consequently capable of expressing mature or old "age" markers if the cell is capable of aging and/or to reveal a disease phenotype if present. For example, a progerin-like protein induces iPSC-derived somatic cells to reach a permissive state, enabling modeling of late-onset diseases.

As used herein, the term "somatic cell" refers to any cell of an organism, which is a constituent unit of a tissue, skin, bone, blood, or organ, other than a gamete, germ cell, gametocyte, or undifferentiated stem cell. Somatic cells include progenitor cells and terminally differentiated cells. Such somatic cells include, but are not limited to, neurons, fibroblast cells, cardiomyocyte cells, epithelial cells, neuroendocrine cells, pancreatic cells, astrocytes, hematopoietic cells, midbrain dopamine neurons, motoneurons, and/or cortical neurons. As used herein, the term "neural cell culture" refers to a cell culture of neurons and/or glia wherein the cells display characteristics of cells of the central and/or peripheral nervous systems.

As used herein, the term "stem cell" refers to a cell that is totipotent or pluripotent or multipotent and is capable of differentiating into one or more different cell types, such as embryonic stem cells or stem cells isolated from organs, for example, mesenchymal or skin stem cells or induced pluripotent stem cells. As used herein, the term "embryonic stem cell" refers to a cell isolated from an embryo or placenta or umbilical cord. As used herein, the term "induced pluripotent stem cell" or "iPSC" refers to a type of pluripotent stem cell that is similar to an embryonic stem cell but is created when somatic (e.g., adult) cells are reprogrammed to enter an embryonic stem cell-like state by being forced to express factors important for maintaining the "stemness" of embryonic stem cells (ESCs), i.e., their ability to be led to commit to different differentiation pathways. As used herein, the term "progenitor" in reference to a cell refers to an intermediate cell stage wherein said cell is no longer a pluripotent stem cell and is also not yet a fully committed cell. Progenitor cells in this disclosure are included within somatic cells.

Stem cells according to the present disclosure can be "totipotent" stem cells, "pluripotent" stem cells, and/or "multipotent" stem cells. As used herein, the term "totipotent" refers to an ability of a cell to differentiate into any type of cell in a differentiated organism, as well as into a cell of extra embryonic materials such as placenta. As used herein, the term "pluripotent" refers to a cell or cell line that is capable of differentiating into any differentiated cell type. As used herein, the term "multipotent" refers to a cell or cell line that is capable of differentiating into at least two differentiated cell types.

Mouse iPSCs were reported in 2006 (Takahashi and Yamanaka, *Cell* 126:663-676 (2006)), and human iPSCs were reported in late 2007 (Takahashi et al. Cell. 2007 Nov. 30; 131(5):861-72). Mouse iPSCs demonstrate important characteristics of pluripotent stem cells, including the expression of stem cell markers. Human and animal iPSCs also express stem cell markers and are capable of generating cells characteristic of all three germ layers. Unlike an embryonic stem cell, an iPSC is formed artificially by the introduction of certain embryonic genes into a somatic cell (such as a OCT4, SOX2, and KLF4 transgenes). See, for example, Takahashi and Yamanaka, *Cell* 126:663-676 (2006) and Agarwal et al., *Nature* 292-296 (2010). iPSC can be produced from adult human skin cells, or fibroblast cells, which are transfected with one or more genes such as, for example, one or more of OCT4, SOX2, NANOG, LIN28, and/or KLF4. See, Yu et al., *Science* 324:797-801 (2009). Alternatively, they can be produced from other types of somatic cells, such as blood or keratinocytes.

As used herein, the term "age-appropriate iPSC-derived somatic cell" refers to any cell that was derived from the differentiating of a first stem cell (which in turn may have come from the reprogramming of a primary somatic cell) followed by contact with progerin, a progerin-like protein, or other functionally equivalent mutated lamin A protein. Age-appropriate iPSC-derived somatic cells are not necessarily characterized by a chronological marker signature of the first cell from which they were derived and may display an immature, young, mature or old age-related marker signature. These cells are "age-appropriate" in that they display markers of a cell age that is appropriate for their intended use. For example, a mature but not old cell is appropriate for establishing models of cells of adult but not old individuals.

As used herein the term, "in vitro" refers to an artificial environment and to processes or reactions that occur within an artificial environment. In vitro environments include, but are not limited to, test tubes and cell cultures.

As used herein the term, "in vivo" refers to the natural environment (e.g., in an animal) and to processes or reactions that occur within a natural environment, such as embryonic development, cell differentiation, neural tube formation, etc.

As used herein, the term "cultured cells" generally refer to cells that are maintained in vitro. Cultured cells include "cell lines" and "primary cultured cells." The term "cell culture" refers to any in vitro culture of cells. Included within this term are continuous cell lines (e.g., with an immortal phenotype), primary cell cultures, finite cell lines (e.g., non-transformed cells), and any other cell population (notably neurons) maintained in vitro, including embryos, pluripotent stem cells.

As used herein, the terms "culture media," and "cell culture media," refer to media that are suitable to support the growth of cells in vitro (i.e., cell cultures, cell lines, etc.). It is not intended that the term be limited to any particular culture medium. For example, it is intended that the definition encompass outgrowth as well as maintenance media. Indeed, it is intended that the term encompass any culture medium suitable for the growth or maintenance of the cell cultures and cells of interest.

The term "small molecule" as used herein, refers to any organic molecule of a size comparable to those organic molecules generally used in pharmaceuticals. The term excludes biological macromolecules (e.g., peptides, proteins, nucleic acids, etc.). Preferred small molecules range in size from approximately 10 Da up to about 5000 Da, more preferably up to 2000 Da, and most preferably up to about 1000 Da.

Methods for Inducing Aging in an iPSC-Derived Cell

Within certain embodiments, the present disclosure provides methods for inducing accelerated aging in an iPSC-derived cell, such as an iPSC-derived somatic cell, which methods include contacting an iPSC-derived cell with a progerin-like protein, thereby inducing in the cell one or more chronological marker signatures and/or other age-related characteristics. Within some aspects of these embodiments, a marker signature and/or characteristic is associated with aging and/or one or more disease phenotype.

For example, cell type-specific chronological marker signatures can include, but are not limited to, a combination of one or more of the chronological markers presented in Tables 1 and 2 and/or the absence of one or more of the chronological markers presented in Tables 1 and 2. Cell type-specific characteristics can include, but are not limited to, one or more phenotypes such, for example, neuromelanin accumulation in aged iPSC-derived dopamine neurons. Disease phenotypes (related to Parkinson's disease) in neurons include, but are not limited to, pronounced dendrite degeneration, progressive loss of tyrosine-hydroxylase (TH) expression, and/or enlarged mitochondria or Lewy body-precursor inclusions. Progerin-induced aging of Parkinson's disease (PD)-iPSC-derived dopamine neurons revealed disease phenotypes that may be based upon genetic susceptibility.

It will thus be understood that disease phenotypes may, in some instances, be based upon aging and/or genetic susceptibility. Accordingly, the present disclosure provides methods for inducing aging to examine late-onset disease and/or disorders in age-appropriate hiPSC-based cell culture models, which are characterized by the induction and display of one or more chronological marker signatures, and optionally one or more disease signatures (including for example genetic pre-disposition).

The methods of present invention can be applied to production of aged cells or mature cells from somatic cells (whether iPSC-derived or primary cells) or from stem cells or from fully differentiated or partially differentiated cells.

The present disclosure also provides: (1) methods for inducing maturation or aging in a cell, including a somatic, a stem cell, and/or a stem cell-induced somatic cell displaying a marker signature of a "young" or of an "immature" cell; (2) methods for using induced aging in cell cultures (whether somatic or stem cell cultures, iPSC-derived or primary, or cells in the course of differentiation) to study chronological effects in late-onset diseases and/or disorders, such as Parkinson's disease (PD), in cultures of age-appropriate cells; and (3) iPSC-derived cells, including age-appropriate iPSC-derived cells, which produce one or more chronological markers or do not produce one or more chronological markers, the presence or absence of which chronological markers is characteristic of a chronological marker signature and/or a particular cellular phenotype (see, Table 1).

TABLE 1

Summary of Chronological Marker Signature Phenotypes

| Phenotypes | "Young" Fibroblast | "Old" Fibroblast | "Young" mDA neuron | "Old" mDA neuron | "Old" PD mDA neuron |
|---|---|---|---|---|---|
| Nuclear shape | Uniform | Folding/ blebbing/ expansion | Folding | More folding/ sporadic blebbing | Same |
| LAP2α | Up | Down | Up | V: Mostly unchanged EA: Down | Same |
| H3K9me3 | Up | Down | Up | V: Mostly unchanged EA: Down | Same |
| HP1γ | Up | Down | Up | V: Mostly unchanged EA: Down | Same |
| γH2AX foci | Rare | Frequent | Moderate | Frequent, larger | Frequent (already larger) |

TABLE 1-continued

Summary of Chronological Marker Signature Phenotypes

| Phenotypes | "Young" Fibroblast | "Old" Fibroblast | "Young" mDA neuron | "Old" mDA neuron | "Old" PD mDA neuron |
|---|---|---|---|---|---|
| mtROS | Low | High | Moderate | High | ? |
| Senescence | Rare | Frequent | NA | NA | NA |
| Apoptosis | NA | NA | Moderate | High | Higher (?) |
| Neurites | NA | NA | Long | Short | Shorter |
| P-Akt | Moderate | Increased | Moderate | Increased | Decreased |

Some embodiments of the present disclosure provide methods for the use of a set of cellular markers that closely correlate with the chronological age of a donor cell, such as a donor fibroblast, which cellular markers include, but are not limited to, markers of nuclear organization, heterochromatin, DNA damage, and mitochondrial stress. Without being bound by theory, it is believed that one or more age-associated markers, associated with the age of the cell of the original donor, are lost upon reprogramming. Moreover, certain features of aging are not reacquired by iPSC-derived lineages upon differentiation. Thus, apparently healthy, non-HGPS cells, which are exposed to a progerin-like protein, induces one or more age-associated markers that define the age of the donor cell prior to iPSC induction.

Thus, the present disclosure provides methods for inducing aging in a cell, which aging mimics several aspects of normal aging in iPSC-derived lineages but is accelerated. The iPSC-derived cells include but are not limited to fibroblasts. Additionally, the present disclosure demonstrates one utility of the disclosed methods and cells: for modeling late-onset disorders such as Parkinson's disease and teaches the establishment of similar models for other diseases. The cell exposed to a progerin-like protein can be, or can be derived from, an iPSC or can be or can be derived from another type of stem cell, such as embryonic stem cells, skin stem cells from adult individuals, mesenchymal stem cells, hematopoietic stem cells and the like. Indeed, a progerin-like protein can be used to induce aging in any type of somatic cell regardless of provenance, even a cell in which progerin is not expressed even in HGPS patients, such as a neuron. However, it is difficult to obtain neurons from healthy donors, so a combination of stem cell differentiation and progerin-like protein exposure is a preferred method to obtain neurons expressing an "old" chronological marker signature.

Table 2 presents a set of age-associated markers that are found in primary fibroblasts derived from aging donors, which markers are lost during the reprogramming of a fibroblast to an iPSC and that are not produced upon differentiation of such an iPSC to a differentiated cell, such as a fibroblast-like cell or an mDA neuron. That is, reprogramming/differentiation generates cells having "young" phenotype (which would be age-inappropriate for studying late-onset diseases) regardless of the age of the somatic cell donor. Age-associated markers can, however, be reestablished upon contacting with and/or overexpression of a progerin-like protein, thereby giving rise to an "old" or mature iPSC-derived cell that would be age-appropriate for studying mature cells or late-onset disease or, in the case of mature cells, for use in therapy.

For example, iPSCs derived from a Parkinson's disease (PD) patient and an apparently healthy donor appear to be phenotypically identical despite their genotypic differences. Upon differentiation into mDA neurons only minor differences were observed between a PD cell versus a control cell (no/mild disease signature). Progerin triggers an mDA aging-like signature in an iPSC-derived mDA neuronal cell and also reveals multiple disease-associated (PD-associated) phenotypes that have interactions between genotype and phenotype in PD iPSC-derived mDA neurons (i.e., enhanced disease signature).

TABLE 2

Representative Phenotypes and Associated Markers

| Phenotypes | Method of detection | Method/length of progerin exposure |
|---|---|---|
| Fibroblast aging signature | | |
| Nuclear folding and blebbing | Lamin A/C | Modified-RNA, 3 days |
| Loss of nuclear organization proteins | LAP2α | Modified-RNA, 3 days |
| Loss of heterochromatin | H3K9me3, HP1γ | Modified-RNA, 3 days |
| Accumulation of DNA damage | γH2AX | Modified-RNA, 3 days |
| Increased mitochondrial ROS generation | MitoSOX | Modified-RNA, 3 days |
| Telomere shortening | Telomeric repeats Q-FISH probe | Modified-RNA, 3 days |
| Upregulation of senescence markers | SA-β-Gal | Modified-RNA, 3 days |
| mDA neuron aging signature | | |
| Enhanced nuclear folding and blebbing | Lamin A/C | Modified-RNA, 5 days; Lentivirus, 2 days-6 months |
| Accumulation of DNA damage | γH2AX | Modified-RNA, 5 days |
| Increased mitochondrial ROS generation | MitoSOX | Modified-RNA, 5 days |
| Dendrite shortening | MAP2ab | Modified-RNA, 5 days |
| Neurodegeneration gene expression signature | RNA-seq | Modified-RNA, 5 days |
| Hyperactivation of p-AKT | p-AKT, p-4EBP1, p-ULK1 | Modified-RNA, 5 days |
| Mild decrease of TH+ neurons | TH in vivo | Lentivirus, 3-6 months |
| Accumulation of neuromelanin | Electron microscopy in vivo | Lentivirus, 6 months |
| PD disease signature | | |
| Enhanced susceptibility to cell death activation | Cleaved caspase-3 | Modified-RNA, 5 days |
| Accelerated dendrite shortening | MAP2ab | Modified-RNA, 5 days |
| Loss of p-AKT | p-AKT, p-4EBP1, p-ULK1 | Modified-RNA, 5 days |
| Pronounced/progressive loss of TH+ neurons | TH in vivo | Lentivirus, 3-6 months |
| Enlarged mitochondria | Electron microscopy in vivo-PINK1 only | Lentivirus, 6 months |
| Multilamellar inclusions | Electron microscopy in vivo-Parkin only | Lentivirus, 6 months |

Markers that predict a somatic cell donor's age, which can be used to monitor cellular age during reprogramming, differentiation, and induced aging, include telomere length, which is shortened as the cell ages and which is restored by reprogramming and the resulting production of functional telomerase. Agarwal et al., *Nature* 464:292-296 (2010) and Marion et al., *Cell Stem Cell* 141-154 (2009)). Similarly, iPSC induction rejuvenates the mitochondria of aged cells. Prigione et al., *Stem Cells* 721-733 (2010) and Suhr et al., *PloS One* 5:e14095 (2010). Those studies were limited, however, to a comparison of individual phenotypes between cell types that are highly distinct (fibroblasts versus iPSCs). In contrast, the present disclosure provides a range of age-related markers, which markers correlate with cellular age and corresponding cell fates (donor fibroblast versus iPSC-derived fibroblast).

Additional suitable markers include, but are not limited to, methylation levels at particular CpG sites, which are predictive of donor age across multiple tissues (Hannum et al., *Mol. Cell.* 49:359-367 (2013) and Koch and Wagner, *Aging* 3:1018-1027 (2011)) and methylation patterns that reflect epigenetic memory in iPSCs of donor cell fate (Kim et al., *Nature* 467:285-290 (2010) and Polo et al., *Nat Biotechnol* 28:848-855 (2010)).

As part of the present disclosure, it was observed that progerin levels may affect the timing upon which age-related phenotypes appear. For example, modified-RNAs can be employed to rapidly induce very high levels of expression and trigger age-related marker expression within days in fibroblasts (3 days) and in neurons (5 days). In contrast, lentiviral expression under the control of a neuron-specific promoter led to much lower levels of expression and did not trigger an obvious phenotype at 1 month after transplantation while robust and progressive phenotypes were observed at 3 and 6 months post grafting. Thus, neurodegenerative phenotypes can be induced both in vitro and in vivo at a rate that is substantially greater than occurs during normal aging. Thus, the induced aging methods that are disclosed herein provide suitable models for assessing and affecting late-onset pathology. They also have implications in inducing cell maturation, especially when the progerin-like protein expression can be induced and then turned off.

Progerin expression using modified-RNAs or expression under a neuron-specific promoter bypasses the differential progerin levels found among various tissues in HGPS patients. Tissue-specific expression of A-type lamins is likely the reason why the disease does not affect organ systems equally. Rober et al., *Development* 105:365-378 (1989). In particular, the CNS is thought to be protected by the expression of miR-9, which targets lamin A and progerin but not lamin C. Nissan et al., *Cell Rep.* 2:1-9 (2012). Therefore, HGPS iPSC-derived neurons are not suitable alternatives to the use of progerin-mediated in vitro neuronal aging.

The present disclosure demonstrates the induction of cell type-specific responses in different cell lineages. (Table 2). Moreover, it is demonstrated herein that progerin exposure can reestablish age in fibroblasts and can phenocopy certain aspects of normal neuron aging, such as the presence of neuromelanin in grafted mDA neurons, global transcriptional changes in mDA neurons after progerin exposure, and the progerin-induced in vitro dendrite degeneration phenotype. It is believed that the progerin-mediated changes as a degenerative response given the breakdown of neurites and the progressive nature of the phenotype, which occur after a very extensive fiber network has been established. Those criteria are distinct from the reduced primary fiber outgrowth that may also reflect a "neurodegeneration" phenotype. Sánchez-Danés et al., *EMBO Molecular Medicine* 4:380-395 (2012).

The present disclosure can also be applied to induce aging of a variety of cell lineages. These cells include major cell types found in a variety tissues and organs, including, but not limited to, brain, heart, liver, kidney, spleen, muscle, skin, lung, blood, artery, eye, bone marrow, and lymphatic system. For example, Table 3 lists additional cell types and their aging markers that can benefit from progerin-induced aging or maturation in vitro (See e.g., A. Sheydina et al., *Clinical Science* (2011) 121, (315-329); U. Gunasekaran and M. Gannon, 2011, *Aging,* 3(6): 565-575). In addition, although iPSC-derived cells have been used to study neurodegenerative diseases as summarized in Table 7, including ALS, Parkinson's disease and Alzheimer's disease, these iPSC-derived neurons are not age-modified and thus may not adequately represent neurons in these late-onset diseases.

TABLE 3

Additional Cell Aging Phenotypes and Associated Markers

| Cell Phenotypes | Markers and method of detection |
|---|---|
| **Cardiomyocytes** | |
| Reduced contractile and luistropic function | MHC, SERCA2, NCX1, mitochondrial proteins and heteroplasmy, and Cx43 |
| Increased cell diameter/hypertrophy | ANP, BNP, ERK1/2, NFAT, calcineurin and S6 kinases |
| Fibrosis and apoptosis | TERT, IGF-1, PI3K, ET-1, SIRT1 SIRT7, caspases, AIF and survivin |
| Reduced proliferation | Cyclin D1, cyclin D2, cyclin D3, pRb, p130 and CDK2 |
| Organization of sarcomeric proteins, calcium handling, and electrophysiology properties, poor graft-host integration and arrhythmias | IHC, EM |
| **Pancreatic β cells** | |
| Decreased insulin secretion | ATP production, glucose oxidation, $K_{ATP}$-channel, Foxm1, Pdx1, |
| Loss of proliferation capacity | MTS assay, D cyclins, p16Ink4a, Cdk4/6 |
| Amylin aggregation | IAPP/amylin |
| Glucose responsiveness | Glucose tolerance and insulin response assays |
| **Kidney cell** | |
| Tubular atrophy, fibrosis, glomerulosclerosis | IHC, Electron microscopy |
| Extracellular matrix and complement activation genes | MMP20, IGF1R, FAM83F, MMP25, ADCY1 |
| **Osteoblasts** | |
| Terminal differentiation | Col1A1, osteocalcin, osteonectin, osteopontin, ALP |
| Mineralization | Calcium deposit, ALP |
| **Osteoclasts** | |
| Terminal differentiation and polarization | Cathepsin K, MMP9, RANKL |
| **Hepatocytes** | |
| Increase in nuclei size and polyploidy, and mitochondrial volume | IHC, Electron microscopy |
| Lipofuscin deposition | Lipofuscin, decline in intracellular proteinolysis. |

TABLE 3-continued

Additional Cell Aging Phenotypes and Associated Markers

| Cell Phenotypes | Markers and method of detection |
|---|---|
| **Dopamine neurons** | |
| Apoptosis | DAT, pacemaker activity, neuromelanin |
| **Hematopoietic stem cells** | |
| Differentiation marker | Notch signaling |

TABLE 7 iPSC-based disease models

| Disease of iPSC-based model | Disease phenotypes not observed that could benefit from progerin overexpression | Reference |
|---|---|---|
| ALS | Cytoplasmic aggregates, decreased cell survival, altered neurite development | Bilican et al., 2012 *Proc Natl Acad Sci USA.* 2012 Apr. 10 ; 109(15): 5803-8; Burkhardt et al., 2013 *Mol Cell Neurosci.* 2013 September; 56: 355-64; Egawa et al., 2012 *Sci Transl Med.* 2012 Aug. 1; 4(145): 145ra104 |
| Alzheimer's disease | Decreased cell survival | Israel et al., 2012 Nature. 2012 Jan. 25; 482(7384): 216-20; Koch et al., 2012 Am J Pathol. 2012 June; 180(6): 2404-16 |
| Parkinson's disease | Loss of TH, decreased cell survival | Cooper et al., 2012 Prog Brain Res. 2012; 200: 265-76; Nguyen et al., 2011 Cell Stem Cell. 2011 Mar. 4; 8(3): 267-80; Seibler et al., 2011 *J Neurosci.* 2011 Apr. 20; 31(16): 5970-6.; Chung et al., 2013 Am J Ophthalmol. 2014 February; 157(2): 464-469 |

As disclosed herein, contact with progerin or other progerin-like protein can mimic normal aging, which is the basis for the present methods for producing cells having an aged-like state, which cells are suitable for modeling late-onset diseases such as PD. For example, a robust degenerative phenotype was observed using the induced aging strategy in at least two genetic PD-iPSC models. Progerin expression mimics at least one aspect of PD by inducing a progressive reduction in TH+ neuron number upon long-term exposure in vivo.

As disclosed herein, the present methods provide introducing exogenous progerin or a progerin-like protein to a cell at a dosage that will be sufficient to induce accelerated aging of the cell. Progerin is expressed in HGPS patient fibroblasts at 40-100× the endogenous level expressed in healthy young and old donor fibroblasts by qPCR (see McClintock D, et al. PLoS ONE. 2007; 2(12):e1269). In the current exposure, progerin was overexpressed in iPSC-derived fibroblasts and iPSC-derived mDA neurons at 1-5× what is found in HGPS iPSC-derived fibroblasts. In some embodiments, the expression of the exogenous progerin or progerin-like protein is about 10 times to about 5000 times higher than the expression of endogenous progerin in said cell. In some preferred embodiments, the expression of the exogenous progerin or progerin-like protein is about 40 times to about 500 times higher than the expression of endogenous progerin in said cell. A narrower range is from about 40 times to about 200 times higher than the expression of endogenous progerin in the cell.

Also disclosed herein, are methods for maturing a differentiated iPS cell, which methods are based upon the observation that the expression of progerin at lower levels can facilitate the maturation of differentiated iPS cells. For example, induced aging methods are provided, which are complementary to iPS cell methodologies known in the art, which methods comprise the programming of both cell fate and cell age.

Progerin-Mediated Age Acceleration of Induced Pluripotent Stem Cell-Derived Somatic Cells Progerin is a mutant form of Lamin A and lacks 50 amino acids near C terminus. This mutation prevents removal of the farnesyl group such that progerin accumulates at the nuclear rim. Progerin is a nuclear lamina protein associated with Hutchinson-Gilford Progeria Syndrome (HGPS). Lamin A is also believed to be involved in normal aging (Scaffidi et al., *Science* 312:1059-1063 (2006)). HGPS is very rare and results from de novo mutations (1 per 8 million births; 140 cases in medical history, 80 known cases alive today). The most common mutation is 1824C>T leading to a silent p.Gly608Gly mutation that activates a cryptic splice site. HGPS is usually fatal with the average age of death at 13 years of age. The clinical symptomology includes, but is not limited to, cardiovascular degeneration, musculoskeletal degeneration, arthrosclerosis or alopecia. However, there are no obvious neurodegeneration symptoms by the time of death. Other diseases, like HGPS, are known for symptoms of premature aging. See, Table 4.

TABLE 4

Genetic Syndromes Considered High Ranking Candidates for Segmental Progeroid Syndromes, Which also Show Significant Differences from Normal Aging

| Syndrome | Inheritance | Mean Life-span (years) | Progeroid features | Causal mutation | Potential mechanistic relevance to normal aging |
|---|---|---|---|---|---|
| Down | De novo trisomy | ~60 | Cataracts, greying of hair, alopecia, diminished subcutaneous fat, thyroid dysfunction, neurodegeneration | Unknown | ? |
| Werner | Autosomal recessive | ~47 | Cataracts, osteoporosis, arteriosclerosis, atherosclerosis, diabetes, malignancies | Loss of function mutations in WRN (RECQL2) | Acceleration of replicative senescence |
| Cockayne | Autosomal recessive | ~20 | Deafness, retinal degeneration, atherosclerosis, demyelination | Loss of function mutations in CS-A (ERCC8) and CS-B (ERCC6) | Decrease genome maintenance? |
| Hutchinson-Gilford | Dominant negative | ~12 | Atherosclerosis, sarcopenia, osteolysis, diminished adipose tissue | Dominant negative form of lamin A (LMNA) | Decrease ability to maintain cells? |
| Ataxia Telangiectasia | Autosomal recessive | ~20 | Dermal sclerosis, immunodeficiency, malignancies, greying of hair, cerebellar ataxia | Loss of function mutation in ATM (phosphatidylinositol 3-kinase) | (i) Decreased genome maintenance (ii) Accelerated neurodegeneration? (iii) Reduced immune diversity? |
| Berardinelli-Seip syndrome (congenital generalized lipodystrophy type 1 and 2) | Autosomal recessive | ~40 | Absence of adipose tissue, severe insulin resistance, diabetes mellitus, cardiomyopathy, hypertension, vascular disease | Loss of function mutations in AGPAT2 (encoding 1-acylglycerol-3-phosphate O-acyltransferase) or BSCL2 (encoding seipin) | Altered insulin signaling? Decreased membrane integrity? Increased glycation damage? |

The data presented herein demonstrate that reprogramming of cellular age may prevent stem cells, such as iPSC cells in culture and stem-cell derived lineages such as iPSC-derived somatic cells, from accurately modeling late-onset disorders, such as Parkinson's disease. A set of candidate age-related cellular markers has been described in fibroblasts derived from Hutchinson-Gilford progeria syndrome (HGPS) patients (Scaffidi et al., *Science* 312:1059-1063 (2006), Scaffidi et al, *In Nat Med* 11(4):440-445 (2005)). HGPS is a rare genetic disorder characterized by premature aging of various tissues resulting in early death with an average life expectancy of 13 years (Hennekam *Am J Med Genet A* 140:2603-2624 (2006).

Mutations in LMNA, the gene coding for the nuclear envelope protein lamin A, result in the activation of a cryptic splice site which produces a shorter transcript known as progerin. Progerin protein aberrantly accumulates in the nuclear membrane and interferes with the normal lamin A function as an important scaffolding protein that regulates several processes in the nucleus including chromatin organization, heterochromatin formation, the DNA damage response, cell cycle and gene transcription and affects other processes implicated in normal aging such as telomere length or function and cellular senescence (reviewed in (Dechat et al., *Genes Deve* 22:832-853 2008)). Interestingly, low levels of progerin are also expressed in healthy individuals, and a similar age-associated profile has been observed in fibroblasts from normally aged donors (Scaffidi et al., *Science* 312:1059-1063 (2006).

In certain embodiments, the present disclosure provides a set of chronological marker signatures that correlate with donor age, for example the age of a fibroblast donor, which marker signatures include, but are not limited to, markers of nuclear morphology and expression of nuclear organization proteins as well as markers of heterochromatin, DNA damage, and reactive oxygen species. These age-associated chronological marker signatures in "old" fibroblasts are lost during reprogramming and are not reacquired during subsequent differentiation, supporting the hypothesis that iPSC-derived cells do not maintain age memory. Tissue-specific age-associated marker signatures can be induced in both iPSC-derived fibroblasts and mDA neurons following short-term progerin exposure. The ability to rapidly induce chronological marker signatures that are associated with cellular age is employed in methods disclosed herein for modeling Parkinson's disease in vitro and following transplantation of iPSC-derived mDA neurons in vivo.

As disclosed herein, several age- and disease-related phenotypes, which are not observed using current iPSC technologies, as provided by cells of the present disclosure, include, but are not limited to, dendrite degeneration, formation of age-associated neuromelanin, AKT deregulation, selective reduction in the number of TH+ neurons, ultrastructural evidence of mitochondrial swelling and inclusion bodies, and the like. Induced aging provides model systems for iPSC studies and that may be adapted to other cell types and disease pathologies to address the contribution of genetic and age-associated susceptibility in late-onset disorders.

Thus, the present disclosure provides chronological marker signatures including, but not limited to, global genetic and epigenetic signatures, as models for primary fibroblasts and/or iPSC-derived fibroblasts and iPSC-derived midbrain dopamine neurons. In certain aspects, the chronological marker signatures reflect cellular behaviors capable of identifying genome-wide genetic and epigenetic profiles as precise signatures of cellular age. Cellular age can, for example, be determined by interactions between age-related markers with genetic and/or via epigenetic profiles.

Figure 1A:
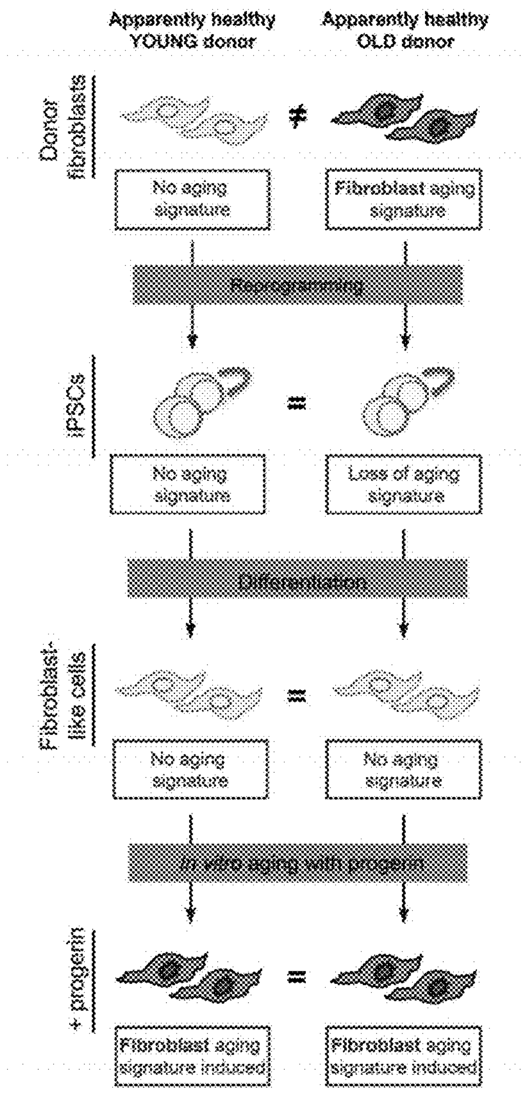
FIG. 1A-1B presents an illustrative summary diagram of some embodiments of the present disclosure. (A) A set of age-associated markers found in primary fibroblasts derived from old donors are lost during reprogramming to iPSCs and are not regained upon differentiation of iPSCs to fibroblast-like cells or mDA neurons. As a result, the reprogramming/differentiation paradigm generates cells with a “young” phenotype regardless of donor age. However, age-associated markers can be reestablished upon overexpression of progerin, giving rise to “old” iPSC-derived cells. (B) iPSCs derived from PD patients and apparently healthy donors appear to be phenotypically identical despite their genotypic differences. Upon differentiation into mDA neurons only minor differences are observed between PD versus control cells (no/mild disease signature). However, progerin overexpression triggers an mDA aging-like signature and reveals multiple disease-associated phenotypes that require the interaction between genotype and phenotype in PD iPSC-derived mDA neurons (enhanced disease signature).
Figure 1B:
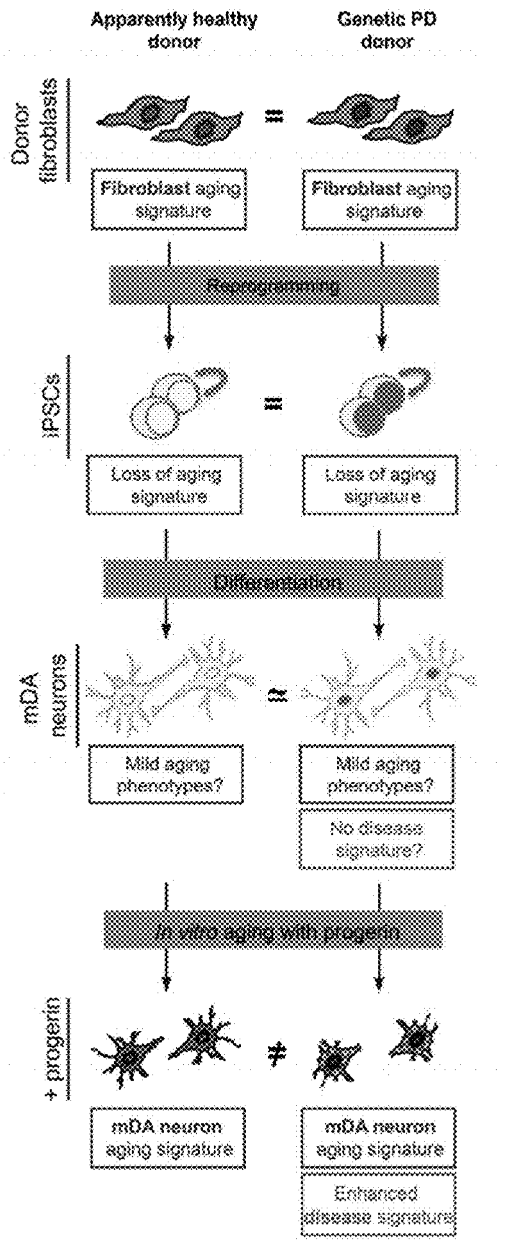

Reprogramming of age-related markers is based upon the present observations that: (1) HGPS fibroblast cells and fibroblasts isolated from an 82 year old donor shared both age-related marker signatures and progeria marker signatures, which signatures are reset to a "young" state upon reprogramming into iPSCs; (2) fibroblasts derived from (i.e., differentiated) HGPS-iPSCs but not from control-iPSCs (e.g., non-diseased iPSCs) re-establish age-related marker signatures and HGPS-related marker signatures upon differentiation; and (3) age-related marker signatures can be generated "on demand" by expressing a synthetic progerin mRNA within the differentiated young/old-iPSC fibroblasts. (FIG. 1).

The data presented herein provide cellular parameters such as passage number, maturation stage, and culture conditions on the appearance/absence of age-related marker signatures in either a reprogrammed or differentiated condition. Further, these data are predictive of additional candidate age-related marker signatures and the evaluation of unbiased profiling studies. For example, these data address whether global gene expression or epigenetic data sets explain the above described pattern of age-related marker signature expression and establish molecular signatures of cellular age. The disclosed data also allow modeling of global interactions between age-associated factors thereby facilitating a determination of causal relationships in the cellular aging response.

Fibroblasts and neurons are known to have specific biomarkers based upon the particular age of the donor individual. The present disclosure demonstrates that age-related markers in primary fibroblasts (young or old) can be "re-set" during iPSC induction to an embryonic-stage marker signature. Subsequently, an embryonic-stage marker signature is largely unchanged upon differentiation. The immature/embryonic/young age-related marker signatures can then be converted to an old age-related marker signature (or to a mature age marker signature) upon contact of the cell with (e.g., expression of) a progerin-like protein. Such age-related markers include, but not limited to, those listed in Table 2 and Table 3.

Using the reprogramming/differentiation paradigm outlined above, a quantitative measurement was made of age-related markers associated with nuclear lamina, morphology, chromatin state, DNA damage response, and mitochondrial function in primary fibroblasts, iPSCs and iPSC-derived fibroblasts (FIGS. 2-6). These data demonstrate that reprogramming cells into stem cells causes loss of age-associated markers whereas progerin expression (whether native in HGPS cells or exogenous, e.g., in genetically modified cells) is sufficient to induce the age-related marker profile observed in old primary fibroblasts from 82 year old donor individuals. Furthermore, the higher levels of progerin expressed in HGPS fibroblasts are sufficient to trigger a rapid manifestation of the aged phenotype without the need for progerin overexpression. These data are in agreement with recent iPSC studies modeling HGPS (Zhang et al., *Cell Stem Cell* 8:31-45 (2011); Liu et al., *Nature* 472:221-225 (2011)). It should be noted that neurons are relatively protected from progerin as they do not express Pamin A. Accordingly, HGPS iPSC-derived neurons cannot substitute for iPSC-derived neurons contacted with exogenous progerin-like protein.

Methods for Inducing Aging in iPSC-Derived Neuronal Cells

Within certain embodiments, the present disclosure provides methods for directing in vitro neuronal aging to establish a disease model of a late-onset neurodegenerative disorder. Without intending to be bound by theory, it is believed that markers associated with a donor's age and/or disease are reset during iPSC-based reprogramming and are not re-established following subsequent differentiation into iPSC-derived lineages. The present disclosure, therefore, provides methods for differentiating iPSC-derived lineages and reestablishing one or more age-associated and/or disease-associated markers, the presence or absence of which markers may comprise one or more age-associated and/or disease-associated marker signatures and/or cell behaviors. In certain aspects of these embodiments, iPS cell differentiation is initiated by one or more compounds including, but not limited to, a Wnt inhibitor and/or a SMAD inhibitor. In other aspects, induced aging is initiated by the expression of endogenous or exogenous progerin.

The advent of iPSC technology has the potential to accelerate the development of therapies for a broad range of genetic disorders and provides a cell culture platform on which routine studies of disease processes may be replicated. The iPSC approach can also yield mechanistic insights into a disease process and therefore identify target sites for future drug development.

Disclosed are methods for introducing an age component into iPSC-based models of late-onset disorders. As described herein, the reprogramming of established somatic cell cultures produces immature induced pluripotent stem cell-derived cell types, which do not exhibit late-onset disorder and/or disease phenotypes as develop in an affected aged individual. Thus in one embodiment, the present disclosure provides methods for introducing "age" and/or "maturation" into iPSC-derived cell types by contacting these cells with a progerin-like protein. Examples of various cell types and the markers for aging include, but not limited to, those listed in Table 2 and Table 3.

In one aspect of these methods, an iPSC-derived somatic cell exhibits one or more markers of a late-onset disease and/or disorder phenotype. In related aspects of these methods, the more permissive state comprises one or more cellular responses that are closely aligned with those observed in the in vivo aged PD brain. As disclosed herein, one or more chronological marker, which comprises one or more chronological marker signature, can be monitored, reprogrammed, and/or induced in iPSC cell cultures. Inducing chronological marker signatures in iPSC-derived cell culture models improves late-onset human disease modeling and therapeutic target discovery and, more generally, addresses fundamental questions related to human disease and age.

The methods disclosed here employ iPSC technology to reset and re-establish age-related markers in neuronal disease cell culture models. Certain epigenetic features, such as residual DNA methylation of the donor cell type, may be retained, at least transiently, following iPSC derivation (Kim et al., *Nat Biotechnol* 29:1117-1119 (2011); Kim et al., *Nature* 467:285-290 (2010); and Polo et al., *Nat Biotechnol* 28:848-855 (2010)). The present disclosure provides data, which demonstrate that the reprogramming of chronological markers in an aged primary cell, such as, for example, a fibroblast, are not reacquired upon conversion to an iPSC and subsequent differentiation of a reprogrammed iPSC to a somatic cell, such as a fibroblast cell and/or a neuronal cell.

Thus, the present disclosure provides methods for comparing chronological marker signatures and/or functional features in different cell types. For example, both proliferating cells (e.g., astrocytes) and post-mitotic cells (e.g., neurons) within the central nervous system may be produced and aged by the methods disclosed herein and used as model systems for studying relationships between cell proliferation and maturation and cell-type specific aging signatures. Examples of various cell types and the markers for aging include, but not limited to, those listed in Table 2 and Table 3.

Progerin or a progerin-like protein can be introduced to a cell using a variety of methods, including viral vectors, nanoparticles, liposomes, electroporation, and gene gun, among others.

A wide variety of viral vectors are well known by and readily available to those of skill in the art, including, for example, herpes simplex viral vectors, lentiviral vectors, Sendai viral vectors, adenoviral vectors, and adeno-associated viral vectors, which viral vectors can be adapted for use in the systems disclosed herein for the delivery of nucleic acids, in particular nucleic acids comprising an expression cassette for the target cell specific expression of a therapeutic protein.

The tropisms of natural or engineered viruses towards specific receptors are the foundations for constructing viral vectors for delivery of nucleic acids. The attachment of these vectors to a target cell is contingent upon the recognition of specific receptors on a cell surface by a ligand on the viral vector. Viruses presenting very specific ligands on their surfaces anchor onto the specific receptors on a cell. Viruses can be engineered to display ligands for receptors presented on the surface of a target cell of interest. The interactions between cell receptors and viral ligands are modulated in vivo by toll like receptors.

The entry of a viral vector into a cell, whether via receptor mediated endocytosis or membrane fusion, requires a specific set of domains that permit the escape of the viral vector from endosomal and/or lysosomal pathways. Other domains facilitate entry into nuclei. Replication, assembly, and latency determine the dynamics of interactions between the vector and the cell and are important considerations in the choice of a viral vector, as well as in engineering therapeutic cargo carrying cells, in designing cancer suicide gene therapies.

Herpes simplex virus (HSV) belongs to a family of herpesviridae, which are enveloped DNA viruses. HSV binds to cell receptors through orthologs of their three main ligand glycoproteins: gB, gH, and gL, and sometimes employ accessory proteins. These ligands play decisive roles in the primary routes of virus entry into oral, ocular, and genital forms of the disease. HSV possesses high tropism towards cell receptors of the nervous system, which can be utilized for engineering recombinant viruses for the delivery of expression cassettes to target cells, including senescent cells, cancer cells, and cells infected with an infectious agent. Therapeutic bystander effects are enhanced by inclusion of connexin coding sequences into the constructs. Herpes Simplex Virus vectors for the delivery of nucleic acids to target cells have been reviewed in Anesti and Coffin, *Expert Opin Biol Ther* 10(1):89-103 (2010); Marconi et al., *Adv Exp Med Biol* 655:118-44 (2009); and Kasai and Saeki, *Curr Gene Ther* 6(3):303-14 (2006).

Lentivirus belongs to a family of retroviridae, which are enveloped, single stranded RNA retroviruses and include the Human immunodeficiency virus (HIV). HIV envelope protein binds CD4, which is present on the cells of the human immune system such as CD4+ T cells, macrophages, and dendritic cells. Upon entry into a cell, the viral RNA genome is reverse transcribed into double-stranded DNA, which is imported into the cell nucleus and integrated into the cellular DNA. HIV vectors have been used to deliver the therapeutic genes to leukemia cells. Recombinant lentiviruses have been described for mucin-mediated delivery of nucleic acids into pancreatic cancer cells, to epithelial ovarian carcinoma cells, and to glioma cells, without substantial non-specific delivery to normal cells. Lentiviral vectors for the delivery of nucleic acids to target cells have been reviewed in Primo et al., *Exp Dermatol* 21(3):162-70 (2012); Staunstrup and Mikkelsen, *Curr Gene Ther* 11(5):350-62 (2011); and Dreyer, *Mol Biotechnol* 47(2):169-87 (2011).

Adenovirus is a non-enveloped virus consisting of a double-stranded, linear DNA genome and a capsid. Naturally, adenovirus resides in adenoids and may be a cause of upper respiratory tract infections. Adenovirus utilizes a cell's coxsackievirus and adenovirus receptor (CAR) for the adenoviral fiber protein for entry into nasal, tracheal, and pulmonary epithelia. CARs are expressed at low levels on senescent and cancer cells. Recombinant adenovirus can be generated that are capable of nucleic acid deliver to target cells. Replication-competent adenovirus-mediated suicide gene therapy (ReCAP) is in the clinical trials for newly-diagnosed prostate cancer. Adenovirus vectors for the delivery of nucleic acids to target cells have been reviewed in Huang and Kamihira, Biotechnol Adv. 31(2):208-23 (2013); Alemany, *Adv Cancer Res* 115:93-114 (2012); Kaufmann and Nettelbeck, *Trends Mol Med* 18(7):365-76 (2012); and Mowa et al., *Expert Opin Drug Deliv* 7(12):1373-85 (2010).

Adeno-associated virus (AAV) is a small virus that infects humans and some other primate species. AAV is not known to cause disease and the virus causes a very mild immune response. Vectors using AAV can infect both dividing and quiescent cells and persist in an extrachromosomal state without integrating into the genome of the host cell. These features make AAV a very attractive candidate for creating viral vectors for use in the systems of the present disclosure. Adeno-associated virus (AAV) vectors for the delivery of nucleic acids to target cells have been reviewed in Li et al., *J. Control Release* 172(2):589-600 (2013); Hajitou, *Adv Genet* 69:65-82 (2010); McCarty, *Mol Ther* 16(10):1648-56 (2008); and Grimm et al., *Methods Enzymol* 392:381-405 (2005).

Global Transcriptome

The present disclosure provides methods for evaluating global transcriptomes by measuring 5-methylcytosine (5-mC) and/or DNA methylation signatures. For example, one component of cell development and reprogramming comprise epigenomic modifications of DNA methylation and histone markers. Both 5-methylcytosine (5-mC) and 5-hydroxymethylcytosine (5-hmC) are drastically modified during neuronal differentiation and under neurodegenerative conditions (Szulwach et al., *Nat Neurosci* 14:1607-1616 (2011) and Irier & Jin, *DNA Cell Biol* 31 (Suppl 1):S42-48 (2012), respectively). The functional role of these epigenetic markers has not, however, been fully explored in the context of differentiated iPSC and in vitro age modeling. Thus, the reprogramming/differentiation/aging paradigm disclosed here for modeling late-onset of neurodegenerative disease provides a platform on which to explore these epigenetic changes and their impact on gene expression.

The data disclosed herein demonstrate genome-wide 5-mC and 5-hmC profiles in age-associated primary fibroblasts and their iPSCs. For example, iPSCs are significantly more methylated in both 5-mC and 5-hmC markers than their primary fibroblasts (FIG. 9) (Wu & Zhang, *Cell Cycle* 10:2428-2436 (2011)). Methylation signatures from both cell types indicate a clear enrichment of increased 5-mC and 5-hmC methylation in telomere regions. In addition to epigenetic characterization, unique transcriptional profiles were identified from iPSC-mDA neurons expressing progerin by RNA-seq. These results show that iPSC-derived mDA neurons expressing progerin are similar in gene expression profile to iPSC-derived mDA neurons originating from an HGPS donor ancestry, suggesting a common signature of aging. Thus, these data show that epigenetic and transcriptional data provide useful insight about progeria-associated and natural aging processes.

The data further demonstrate that use of the presently disclosed reprogramming/differentiation paradigm (FIG. 1) on each of primary, young, old and HGPS fibroblasts have generated a lineage of iPSC, followed by differentiation into iPSC-fibroblasts and iPSC-mDA neuron cell lines. Aging can be induced in the latter iPSC-derived somatic cells. Alternatively, contact with a progerin-like protein can be initiated before or during differentiation of iPSC or any other stem cell to any cell lineage.

In one embodiment, the present disclosure provides methods for integrating DNA methylation data and transcriptomics data with phenotypic age-related marker signature data to provide a more precise cellular description of age. In one embodiment, a more accurate characterization of age (e.g., by measuring expression of several aging markers, e.g., those listed in Table 2 and Table 3) improves modeling of late-onset diseases using somatic cell cultures, such as iPSC-derived cell cultures. In certain aspects of this embodiment, the data integration elucidates progerin-initiated aging characteristics. In other aspects, the method further comprises using forward and/or reverse genetic manipulations.

Data integration can be performed by a number of computational analyses to identify the functional impact of the (epi)genetic changes on aging. For example an integrated analysis of DNA methylation and gene expression may be performed to identify dysregulated pathways and "driving" events that distinguish "old" fibroblasts. These analyses involve identifying the functional relationship between the epigenetic and transcriptional changes present in aged fibroblasts and progerin-induced iPSC-fibroblasts.

One approach is to identify direct regulation of gene expression by methylation status. Differentially methylated regions, from either 5-mC or 5-hmC profiling, may be associated with proximal genes, which are most likely regulated by the DNA methylation. Next, gene expression changes may be identified that are most correlated with these methylation changes.

Another approach is to focus on identifying common pathways that are mutually regulated by both epigenetic and transcriptional changes. Functional enrichment analyses may be performed on genes identified by aberrant methylation status and/or genes that are differentially expressed (Subramanian et al., *Proc Natl Acad Sci USA* 102:15545-15550 (2005)).

Network connectivity of these gene sets can be investigated using tools including, but not limited to, SPIA43, NetBox44, and Enrichment Map, all of which take into consideration the interactions between the genes to identify functional "modules"—a group of interconnected genes that participate in a specific cellular function or pathway and are co-regulated (Merico et al., *PLoS One* 5:e13984 (2010)). Hence, pathways that are represented with high frequency in both methylation and gene expression datasets are likely to be functionally relevant for the aging process.

A correlation of gene expression signatures and perturbed functional pathways with age-related marker signatures can determine genetic processes that drive cellular aging. An example involves modeling quantitative readouts from age-related biomarker signatures (e.g., heterochromatin state, DNA damage and nuclear morphology) as a function of the genetic alteration such as, differential expression and/or differential methylation. Regression models (such as ridge regression, lasso regression, partial least squares (PLS) regression, or support vector regression) can correlate differentially methylated regions with heterochromatin changes measured quantitatively by H3K9me3 marker. Similarly, differentially methylated and expressed genes can be used in supervised classification schemes, using algorithms such as naïve Bayes classifiers, logistic regression and support vector machines, to distinguish DNA damage response from damaged mitochondria function.

These contemplated computational models also may provide a minimal set of genomic features that are most predictive of the aging phenotype. Various feature selection approaches, both in the regression and classification schemes, can be used to identify the genes and epigenetic modifications that are most predictive of the age biomarker assays. For example, qPCR may be used to identify a subset to be used for validation purposes. Alternatively, RNAi experiments can be used to test for functional relationships (Lipchina et al. *Genes Dev* 25:2173-2186 (2011)).

Functional Characteristics of Cellular Aging

In some embodiments, the present disclosure provides methods for testing a relationship between induced aging and chronological aging. In certain aspects of those embodiments, the induced aging process is reversible. In other aspects, the induced and chronological aging models comprise novel marker sets that are relevant to studying age in human brains.

The data presented herein address some embodiments contemplated by the present disclosure, for example: (i) methods for precisely pinpoint an "age-equivalent" for progerin-induced cells (e.g., "induced aging" pushes the cell toward the behavior of an equivalent cell type in a 40 or 80 year old individual) and (ii) methods for reversing progerin-induced changes on a predictable time scale and chronology. In certain aspects, the methods further comprise the step of determining which of the age-associated changes can be found in the aged brain of normal individuals.

Age-Related Marker Sensitivity

Age-related marker sensitivity may be tested in vitro using chronological and progerin-induced cellular aging. The data disclosed herein from primary fibroblasts show a clear difference in the expression of age-related marker signatures when comparing primary fibroblasts derived from 11 year old donor individuals versus primary fibroblasts derived from 82 year old donor individuals. These data did not, however, address the rate of onset of those age-related changes. For example, those changes may occur suddenly once a donor has reached a certain age (e.g., >70 years of age) or there may be a gradual increase in the expression of age associated markers as one gets progressively older. Furthermore, these data did not address whether different sets of age-related marker signatures (e.g., heterochromatin, DNA damage, RNA profile, epigenetic profiles) change in a coordinated manner or whether there is a hierarchy according to which such changes occur.

Primary fibroblasts of three different age groups: (i) 0-15 years, (ii) 30-50 years, (iii) 70-90 years can be obtained from healthy donor individuals. A determination of the established age-related marker signatures (e.g., nuclear lamina structure, heterochromatin, DNA damage and mitochondrial damage) as well as newly discovered age-related marker signatures and/or genetic markers can determine relationships between marker expression and fibroblast donor individual age. For example, age-related marker signature expression can be determined in three independent replicates for each fibroblast line maintained at identical passage numbers and for at least three fibroblast lines for each age group. These time-course data are compared to iPSC derived fibroblast lines from 82 year old donor individuals and iPSC-derived fibroblasts lines from 11 year old donor individuals treated with progerin for either 1, 3, or 5 days.

Analysis of these data may determine the sensitivity of age-related assays and the relationship among various age markers. Those data may yield information about existing hierarchies within and among age-related phenotypes. Second, these data may be used to pinpoint the "age equivalent" for a given phenotype in iPSC-derived fibroblasts treated with a progerin-like protein versus primary fibroblasts of various donor ages and assess whether the temporal changes following progerin-like protein exposure match the chronological changes observed in primary fibroblasts from donor individuals of increasing age. See, FIG. 22.

Age-Related Marker Change Reversibility

The data presented herein demonstrate that age-related marker changes observed during cellular aging were induced following progerin exposure. Moreover, data using a doxycycline (dox)-inducible fibroblast line or transient treatment paradigms with Green Fluorescent Protein (GFP)-progerin mRNA suggest that many progeria-associated phenotypes in fibroblasts and by extension in somatic cells grown in culture are reversible (FIG. 10A) (Scaffidi & Misteli *Nat Cell Biol* 10:452-459 (2008)). It has been reported that age-associated markers can be reversed in normal aged cells by interfering with progerin production (Scaffidi et al., *Science* 312:1059-1063 (2006)). Whether a similar phenotype reversal occurs in non-dividing cells, such as midbrain dopamine (mDA) neurons, or whether age-associated markers are reversed similarly following progerin removal is, however, unclear.

Fibroblast Reversibility

In some embodiments, the present disclosure provides methods for contacting a fibroblast with GFP-progerin or a nuclear GFP control mRNA. In certain aspects, the contacting can be for 3 days. In related aspects, the methods further comprise monitoring the fibroblasts for a sequence in age-related market signature phenotype alterations. In other aspects, the methods further comprise matching the timing of phenotype reversal with a gradual loss of GFP-progerin in the nucleus. Loss of GFP-progerin can, for example, be measured by a loss of GFP expression or by progerin/lamin A levels.

Neuronal Reversibility

In other embodiments, the present disclosure provides methods for contacting a midbrain dopamine neuronal culture with GFP-progerin or a nuclear GFP control mRNA. In certain aspects, the contacting can be for 5 days. In other aspects, the methods further comprise monitoring the neurons for a sequence in age-related marker signature phenotype alterations. In related aspects, the methods further comprise matching the timing of phenotype reversal with a gradual loss of GFP-progerin in the nucleus. The loss of GFP-progerin can be measured by a loss of GFP expression can be measured by progerin and/or lamin A levels.

Age-Related Marker Signature Validation

As disclosed, human tissues were studied for age-related marker signatures that validated the observations in the in vitro testing exemplified herein. In particular, this validation protocol was based upon the observation of specific changes in age-related marker signatures in vitro following reprogramming, differentiation, and progerin induction. These studies addressed the relevance of some of those age-related markers in normal aging of the human brain. For example, the data described herein show a number of changes in samples of brain tissue from aged donors (FIG. 11).

The data presented herein also demonstrate that the expression of lamin A and progerin in the human brains of individuals over 70 years of age despite the reported negative regulation of lamin A by miR-9. (FIGS. 11A and 11B) (Nissan et al., *Cell Rep* 2:1-9 (2012); Jung et al., *Proc Natl Acad Sci USA* 109:E423-431 (2012)). Immunohistochemical methods also detect age-related marker signatures in human paraffin sections (FIG. 11B). A rearrangement of global H3K9me3 organization in brains >70 years of age was also observed (FIG. 11C). Validation of these data may be achieved by screening brain tissue of known ages available at the National Disease Research Interchange (NDRI; ndri.org). Gene expression may be validated by qPCR, 5-mC methylation and 5-hmC determination of candidate sites in accordance with Example 4.

Parkinson's Disease Modeling

Parkinson's disease has a prevalence of approximately $0.5\text{-}1.0\times10^6$ patients affected in the United States. Symptoms include, but are not limited to, rigor, tremor, bradykinesia (slow movement) and/or poor balance/walking. Clinical pathology diagnoses PD primarily due to a loss of midbrain dopamine neurons. The etiology of PD is mostly unknown and sporadic, but multiple genes are involved in familial forms of PD.

In one embodiment, the present disclosure provides methods comprising inducing cellular aging to create late-onset neurodegenerative disease cells, which can, for example, be employed as PD model systems. In certain aspects, the cells are induced pluripotent stem cells.

Induced cellular aging provides a system to model age-related aspects of late-onset neurodegenerative diseases. Such a system can be used to directly test an interaction between genetic susceptibility and age-related vulnerability on disease phenotype.

The present disclosure also provides methods for inducing cellular age in iPSC-derived mDA neurons. In certain aspects, these methods may be employed for modeling of age-dependent effects in Parkinson's disease (PD). The data presented herein address the following issues, for example: (i) using directed differentiation techniques for the generation of authentic mDA neurons; (ii) establishing a broad range of genetic PD-iPSC lines; (iii) validating age-related marker signature phenotypes in iPSC-mDA neurons; (iv) demonstrating an interaction between age phenotypes and disease phenotypes; and (v) establishing gene-edited PD-iPSC lines. These gene-edited lines may contribute to the understanding of genetic susceptibility versus age-induced vulnerability.

The present disclosure also provides cells comprising at least one PD-iPS cell. In one aspect, the PD-iPS cell originates from PD patient skin fibroblasts. In other aspects, the fibroblasts that give rise to PD-iPS cells comprise at least one mutation selected from the group comprising Parkin, PINK1, LRRK2, α-synuclein, and glucocerebrosidase (GBA) (Kitada et al., *Nature* 392:605-608 (1998); Valente et al. *Science* 304:1158-1160 (2004); Zimprich et al., *Neuron* 44, 601-607 (2004); Polymeropoulos et al., *Science* 276: 2045-2047 (1997); Toft et al., *Neurology* 66:415-417 (2006)). They thus express a disease phenotype.

The data presented herein have addressed changes in age-related marker characteristics in the Parkin and PINK1 lines subsequent to recombinant progerin expression. For example, progerin expression induces an accelerated dendrite degenerative and/or shortening phenotype in mDA neurons from iPSC-derived midbrain dopamine cell cultures from either PINK1-mutant or Parkin-mutant Parkinson's individuals (FIG. 15).

Furthermore, Akt signaling provided a very robust phenotype that indicated a clear interaction of genotype with age (FIG. 22). Changes in Akt signaling, in particular decreased p-Akt levels, are associated with early stage PD (Greene et al., *Cell Mol Neurobiol* 31:969-978 (2011)). In contrast, in HGPS, p-Akt is known to be abnormally upregulated (Johnson et al., *Nature* 493:338-345 (2013)). The data disclosed herein demonstrate that, in control-iPSC mDA neurons, there is an increase in p-Akt following progerin exposure, which is consistent with an HPGS phenotype. In contrast, PD-iPSC mDA neurons showed a consistent reduction in p-Akt compatible with inducing a PD-like phenotype.

Reversing Age or Genetic Lesion in Age-Induced Pluripotent Stem Cell Derived Midbrain Dopamine Neurons The present disclosure provides provide a pluripotent stem cell derived midbrain dopamine neuron cell in which aging has been induced. Disease phenotypes in matched iso-genic pairs of mutant and control lines can be employed to evaluate the effect of removing genetic susceptibility from cells.

A reversal of age phenotype can be monitored by: (i) decreased p-AKT activity, (ii) absence or reduction in dendrite degeneration compared to controls, or (iii) reduced rates of apoptosis compared to progerin expressing PD-iPSC derived DA neurons. Gene editing of the mutated gene resets age-related behavior and yield data comparable to those obtained in our control lines Reversibility of PD phenotypes would argue that aging is a necessary, but not sufficient condition, to trigger disease symptoms.

Differentiation of Fibroblast Primary Cells into Midbrain DA Neurons

As disclosed herein, primary fibroblast cells were reprogrammed into induced pluripotent stem cells (see, Example 1), which were switched to a medium promoting neural induction and then further maintained in a medium promoting neuronal maturation (BAGCT, see Example 7). Neurogenic conversion of iPSCs produced iPSC-derived midbrain dopamine cells. In certain aspects, iPSC-derived DA neurons were obtained following small molecule based activation of SHH and canonical WNT signaling during early differentiation stages. This was a highly efficient process with more than half of cells in the culture dish adopting mature midbrain marker profile.

For example, human ESC (H9, H1) and iPSC lines (2C6 and SeV6) can be subjected to a modified Dual SMAD-inhibition (Chambers et al. *Nat. Biotechnol.* 27:275-280 (2009)) based floor plate induction (Fasano et al., *Cell Stem Cell* 6:336-347 (2010)) protocol. Exposure to SHH C25II, Purmorphamine, FGF8 and CHIR99021 can be optimized for midbrain floor plate and yield of novel populations of DA neuron. Following floor plate induction, further maturation (days 11-25 or longer than 25 days in culture up to at least 100 days in culture) can be carried out in differentiation medium based on Neurobasal/B27 in the presence of DA neuron survival and maturation factors (Perrier et al., *Proc Natl Acad Sci USA* 101:12543-8 (2004)) such as AA, BDNF, GDNF, TGFβ3, and dbcAMP. The resulting DA neuron population can be subjected to extensive phenotypic characterization for example using one or more of immunocytochemistry, qRT-PCR, global gene expression profiling, HPLC analysis for the detection of dopamine and in vitro electrophysiological recordings. Yet, other differentiation protocols can be used (Badger J L et al., Neuropharmacology. 2014 January; 76 Pt A:88-9).

Additional Applications/Therapeutic Applications

Cells may be isolated from healthy subjects, at risk subjects, diseased subjects, and subjects of for use in generating undifferentiated iPS cells according to methodology presented herein or as otherwise available in the art. Primary somatic cells used for reprogramming may be isolated from a variety of bodily locations, such as circulating cells and/or cells in tissues of patients/subjects, including but not limited to fibroblasts, skin fibroblasts, white blood cells, circulating white blood cells, mucosal cells, and keratinocytes without regard for the "age" of the cell or the "age" of the donor. In some aspects, primary somatic cells may be young cells expressing a "young" cell marker signature isolated from young donors, which cells may or may not be expressing a disease signature. In other aspects, primary somatic cells may be old cells expressing an "old" marker signature. In further aspects, primary somatic cells may be cells expressing a disease marker signature regardless of the chronological age of the donor. These primary cells can be reprogrammed in culture to give rise to iPSC using any method for generating iPSC from somatic cells. Such methods, other than described or referenced herein, are known in the art.

Generated iPS cells of any origin, including cells generated by methods described herein, may be used in differentiation protocols for producing differentiating and differentiated iPSC-derived cells that may find use in progerin aging compositions and methods of the present disclosures. Differentiating and differentiated iPSC-derived cells include but are not limited to default and nondefault differentiation lineages, including partially differentiated (i.e., differentiating) cells, so long as they are capable of expressing genetic and cell marker signatures of their particular cell types, i.e., permissive cells. Examples of cell types which may find use in aging induction using progerin-like proteins of the present disclosure are iPSC-derived cells including but not limited to neurons (any subtype, such as motoneurons, cortical neurons, peripheral sensory neurons, mid-brain dopamine neurons etc.), cardiomyocytes, hematopoietic stem cells (HSCs), pancreatic beta cells, astrocytes, etc.

Thus, iPS derived cells at certain stages will find use in progerin treatment according to the present disclosure including, but not limited to, iPS derived cells beginning to undergo differentiation, iPS derived cells progressing towards committed cells types, iPS derived cells progressing towards a mature cell type, etc.

In some embodiments, aged iPSC-derived cell types obtained as described herein may find use in disease modeling and for identifying therapeutically relevant cell stages during development, such as identifying progerin-aged cellular stages for use in testing new drug compounds for use as therapeutics and for actual use in treatment of patients. Thus in some embodiments, primary somatic cell donors for iPSC-derived cell types have a disease or a disease phenotype induced in iPSC-derived cell/tissue culture including but are not limited to actual or model neurodegenerative diseases, such as Parkinson's disease (PD), Alzheimer's disease, tauopathies, i.e., a class of neurodegenerative diseases associated with the pathological aggregation of tau protein in the human brain, cardiomyocyte-related diseases (such as cardiac hypertrophy, cardiac fibrosis, channelopathies, for example pathologies of sodium channels, arrhythmias etc.), pancreatic diseases, hematopoietic diseases, metabolic diseases, cancer etc. with progerin or another progerin-like protein.

Nonlimiting examples of specific iPSC-derived cell types and associated disease(s) which can be used in conjunction with progerin-like protein compositions and aging induction methods of the present disclosure include iPSC derived-neurons for neurodegenerative diseases, iPSC-derived cardiomyocytes for degenerative cardiac diseases, iPSC-derived hematopoietic stem cells for leukemia and other white blood cell diseases and disorders and more generally hematopoietic diseases/disorders, iPSC-derived pancreatic beta cells for Type I diabetes, Type II diabetes and certain other types of insulin regulation disorders such as Type II diabetes, iPSC-derived motoneurons for ALS, iPSC-derived cortical neurons for Alzheimer's, iPSC-derived mDA neurons and iPSC-derived cortical neurons for corticobasal degeneration, iPSC-derived astrocytes for neurodegenerative disorders, iPSC derived cardiomyocytes for cardiac hypertrophy and fibrosis, and the like.

In some embodiments, iPSCs differentiated into certain somatic cell types that are immature or take a long time to mature (as assessed for example by protein expression in the cells, gene expression profiles, functional tests, etc.). Such immature cells may be contacted with a progerin-like protein to induce maturation in the cell population so these cells may be used in cell therapy. Examples of such immature iPSCs differentiated cells are iPSC-derived mDA neurons which lack pacemaker activity, expression of the dopamine transporter DAT, and neuromelanin and which require an additional 5 months of maturation in vivo to rescue Parkinsonian mice (Isacson et al., *Trends Neurosci* 20:477-482 (1997; Kriks et al., *Nature* 480:547-551 (2011). Furthermore, based on the BrainSpan: Atlas of the Developing Human Brain (http://www.brainspan.org), gene expression data from pluripotent stem cell-derived neural cells matches the transcriptome of first trimester embryos. Immature neurons can be contacted with a progerin-like protein for the purpose of accelerating their maturation as assessed for the markers listed above as characteristic of the desired mature neuronal subtype contemplated for use in cell therapy and/or drug development. In particular, cells provided by methods of the present disclosure contacted with a progerin-like protein may find use in drug screening, i.e., evaluation of compound candidates for aging control agents, agents for the treatment of specific diseases or disorders, such as those described herein, etc.

Other examples of using iPSC derived cells are HSCs derived from iPSCs which do not express signature markers of adult HSCs and could benefit from treatment with progerin to induce expression of an adult marker signature (including without limitation HoxB4, Tek (a/k/a Tie2) and HoxA9). For examples of other markers see, McKinney-Freeman et al., *Cell Stem Cell* 11:701-714 (2012), showing transcriptomes of developing HSC purified from mice).

As another example, cardiomyocytes derived from iPSCs are immature and will find use in progerin compositions and methods of the present disclosure for identifying induction of maturation markers including but not limited to electrophysiological properties, such as higher sodium currents, reduced sensitivity to lidocaine, beating frequency, sensitivity to tetrodotoxin (TTX), and organizational patterns of sarcomeric proteins, such as actinin, etc., using immunocytochemistry, TEM, electrophysiology and Ca2+ imaging, cells were staining for Troponin T, Troponin I and α-actinin, Ca2+ release into the cytoplasm detected by fluo-4 and fluorescence intensity was traced before and after Tetrodotoxin (TTX) treatment. Sodium channel activity can be measured in a low sodium buffer using perforated patch-clamping.

Ultrastructure of cells can be analyzed with transmission electron microscopy while the presence of t-tubules can be investigated using the fluorescent dye Di-8-ANEPPS. Examples such as in Medine, Heart 99:S2 (2013) and Sheng, *Pfannkuche* (2012).

Beta cells derived from iPSCs will find use in progerin compositions and methods of the present disclosures and contemplated for use in cell therapy and/or drug development. In particular, contacting iPS derived beta cells with a progerin-like protein can be used for inducing expression of a maturation marker Ucn3, along with a capability to induce insulin expression, and release of insulin in response to glucose not found in immature cells. For example, Blum-Melton et al, *Nat Biotechnol* 30:261-264 (2012) show where beta-cell maturation is defined by a decrease in GSIS sensitivity to low glucose levels and by an increase in expression of Ucn3 as shown by intracellular FACS analysis of insulin and Ucn3.

EXAMPLES

Example 1

Sendai Vector System Reprogramming

This example describes an integration-free reprogramming technique via a Sendai vector system. Fusaki et al., *Proc Japan Acad* Ser B:348-362 (2009). This method with such modifications as are described below was used to reprogram somatic cells into iPSC.

It is believed that this method eliminates concerns about insertional mutagenesis induced by integration of the reprogramming vectors contributing to phenotype. For example, this method has generated an integration-free HGPS iPSC cell line (FIG. 18).

Example 2

Progerin Transduction into iPSC-Derived Somatic Cell Culture

This example illustrates methods for the introduction of a progerin gene into iPSC-derived somatic cultures using a synthetic mRNA approach (Warren et al., *Cell Stem Cell* 7:618-630 (2010)) or various vectors. Unlike stable transfection techniques, the addition of mRNAs allows for easy manipulation of the duration of gene expression. This advantage is utilized discontinue progerin expression and to monitor the effects following protein turnover (See, FIG. 19). This protocol can be used to introduce any other progerin-like protein into a cell, whether iPSC, primary stem cell, embryonic stem cell or primary or cultured somatic cell not derived from an iPSC.

The following is a protocol for progerin overexpression using modified-RNA in differentiating or differentiated iPSC-derived cells:

1. Prepare progerin-modified-RNA (methods of synthesis are described in Example 9) and deliver to iPSC-derived somatic cells using Lipofectamine RNAiMAX (Life Technologies) and incubate
    a. For iPSC-derived fibroblasts repeat transfection for 3 consecutive days.
        i. Note: Amount/duration combination optimizes treatment for minimal toxicity and earliest significant effects.
    b. For iPSC-derived dopamine neurons repeat transfection for 5 consecutive days.
        i. Note: Amount/duration combination optimizes treatment for minimal toxicity and earliest significant effects.
    c. For other iPSC-derived somatic cells perform pilot experiments to determine amount and duration of progerin modified-RNA.
    d. Analyze maturation and/or age-associated phenotypes.

Alternatively, expression of progerin can also be achieved through the use of temperature-sensitive Sendai virus expressing progerin. Additionally, expression of progerin can be achieved by using lentivirus.

Example 3

Directed Differentiation of Neuronal Cell Types

This example describes one method of directed differentiation techniques to generate specific neural cell types. Nearly pure populations of CNS lineages, such as midbrain dopamine (mDA) neurons, are used in the methods described herein. The protocol of Kriks et al, *Nature* 2011, infra, can be used (among other methods).

Briefly, a modified version of the dual-SMAD inhibition protocol was used to direct cells towards floor plate-based mDA neurons as described previously (Kriks et al., *Nature* 480:547-551 (2011) and schematized in FIG. 8. iPSC-derived mDA neurons were replated on day 30 of differentiation at 260,000 cells per cm2 on dishes pre-coated with polyornithine (PO; 15 μg/ml)/Laminin (1 μg/ml)/Fibronectin (2 μg/ml) in Neurobasal/B27/L-glutamine-containing medium (NB/B27; Life Technologies) supplemented with 10 μM Y-27632 (until day 32) and with BDNF (brain-derived neurotrophic factor, 20 ng/ml; R&D), ascorbic acid (AA; 0.2 mM, Sigma), GDNF (glial cell line derived neurotrophic factor, 20 ng/ml; R&D), TGFβ3 (transforming growth factor type β3, 1 ng/ml; R&D), dibutyryl cAMP (0.5 mM; Sigma), and DAPT (10 nM; Tocris). One to two days after plating, cells were treated with 1 μg/ml mitomycin C (Tocris) for 1 hour to kill any remaining proliferating contaminants. iPSC-derived mDA neurons were fed every 2 to 3 days and maintained without passaging until the desired timepoint for a given experiment. PO, laminin and fibronectin were added to the medium every 7-10 days to prevent neurons from lifting off.

Example 4

Profiling of mRNA, AMC and DNA Methylation

This example describes one technology to profile mRNA, 5hMC and DNA methylation in the presently described age paradigm. These methods provide data regarding the molecular control of age-related factors.

5-mC Detection

An enhanced reduced-representation bisulfite sequencing (ERRBS) method may be used. In this protocol, genomic DNA is digested by MspI restriction enzyme and fragments are size selected to obtain fragments enriched for CpG sites. These fragments undergo bisulfite conversion, sequenced on Illumina HiSeq200035 and the sequencing data are analyzed by custom software that maps bisulfite-treated sequencing reads and outputs to the methylation status of identified CpG sites.

5-hmC Detection

A Hydroxymethyl Collector™ kit from Active Motif may be used. This protocol is based on the selective addition of a biotin moiety to 5-hmC positions followed by an immunoprecipitation (IP) step. Similar to ChIP-seq experiments, both the total cellular input and IP fragments are sequenced. 5-hmC modifications are identified as regions of high coverage over background levels.

Gene Expression Detection

The RNA-seq protocol may be used. This protocol is well known in the art and is routinely performed at the WCMC epigenomics core. Sequencing experiments will be multiplexed to reduce sequencing cost and to prevent batch effects.

Example 5

Gene Corrected PD-iPSC Lines

This example describes the use of a gene corrected PD-iPSC line (e.g., TALEN-based gene targeting). Although it is not necessary to understand the mechanism of a disclosure, it is believed that these cell lines provide access to iso-genic pairs of PD-iPSC and control iPSC to more precisely distinguish between disease factors related to age and factors related to genetic susceptibility to PD.

Example 6

Lamin A and Progerin Involvement in Normal Aging

This example provides data showing that in normally aged cortex tissue there is: i) Lamin A/progerin upregulation; ii) an altered heterochromatin state; iii) nuclear expansion in neurons. FIG. 11 presents exemplary data showing the expression of lamin A and progerin in aged human brain tissue. Panel A demonstrates that both lamin A and progerin show increased mRNA expression levels in cortex tissue obtained from aged individuals. Panel B depicts the visualization of the nuclear envelope and identification of neurons in paraffin-embedded human cortex tissue by immunofluorescence for Lamin A/C and MAP2 obtained from two donors aged 44 and 82, respectively. Arrows indicate examples of MAP2-positive neurons. Panel C shows western blot analysis (left panel) of soluble tri-methylated H3K9 which indicates a dramatic change in heterochromatin organization with similar timing to lamin A and progerin upregulation. These changes may reflect a reorganization of heterochromatin into insoluble heterochromatic foci with age, as demonstrated by the right panel.

Example 7

Alternative Differentiation of Induced Pluripotent Stem Cells into Midbrain Dopamine Cells Alternatively, neural differentiation of iPSC can be initiated using a modified version of the dual-SMAD inhibition (Chambers et al., *Nat. Biotechnol.* 27:275-280 (2009), herein incorporated by reference). Floor plate induction (Fasano et al., *Cell Stem Cell* 6:336-347 (2010), herein incorporated by reference) protocol can be used based on timed exposure to LDN-193189 (100 nM (ranging in concentration from 0.5-50 μM, Stemgent, Cambridge, Mass.), SB431542 (10 μM (ranging in concentration from 0.5-50 μM, Tocris, Ellisville, Mich.), SHH C25II (100 ng/ml (ranging in concentration from 10-2000 ng/ml, R&D, Minneapolis, Minn.), Purmorphamine (2 μM (ranging in concentration from 10-500 ng/ml, Stemgent), FGF8 (100 ng/ml (ranging in concentration from 10-500 ng/ml, R&D) and CHIR99021 (CHIR; 3 μM (ranging in concentration from 0.1-10 μM, Stemgent). "SHH" treatment refers to exposure, i.e. contact, of cells to a combination of SHH C25II 100 ng/ml+Purmorphamine (2 μM).

Cells can be plated (35-40×$10^3$ cells/$cm^2$) and cultured on matrigel or geltrex (used as purchased) (BD, Franklin Lakes, N.J.) in Knockout serum replacement medium (KSR) containing DMEM, 15% knockout serum replacement, 2 mM L-glutamine and 10-μM (ranging in concentration from 1-25 μM β-mercaptoethanol. KSR medium gradually shifted to N2 medium starting on day 5 of differentiation, by mixing in ratios of 75% (KSR):25% (N2) on day 5-6, 50% (KSR): 50% (N2) day 7-8 and 25% (KSR):75% (N2) on day 9-10, as described previously (Chambers et al., *Nat. Biotechnol.* 27:275-280 (2009), herein incorporated by reference).

On differentiation day 11, media can be changed to Neurobasal medium/B27medium (1:50 dilution)/L-Glut (effective ranges 0.2-2 mM)) containing medium (NB/B27; Invitrogen) supplemented with CHIR (until day 13) and with BDNF (brain-derived neurotrophic factor, 20 ng/ml ranging from 5 to 100; R&D), ascorbic acid (AA; 0.2 mM (ranging in concentration from 0.01-1 mM), Sigma, St Louis, Mo.), GDNF (glial cell line-derived neurotrophic factor, 20 ng/ml (ranging in concentration from 1-200 ng/ml); R&D), TGFβ3 (transforming growth factor type β3, 1 ng/ml (ranging in concentration from 0.1-25 ng/ml); R&D), dibutyryl cAMP (0.5 mM (ranging in concentration from 0.05-2 mM); Sigma), and DAPT (10 nM (ranging in concentration from 0.5-50 nM); Tocris) for 9 days.

On day 20, cells can be dissociated using Accutase® (Innovative Cell Technology, San Diego, Calif.) and replated under high cell density conditions (for example from 300-400 k cells/$cm^2$) on dishes pre-coated with polyornithine (PO); 15 μg/ml (ranging in concentration from 1-50 μg/ml)/ Laminin (1 μg/ml) (ranging in concentration from 0.1-10 μg/ml)/Fibronectin (2 μg/ml (ranging in concentration from 0.1-20 μg/ml) in differentiation medium (NB/B27+BDNF, AA, GDNF, dbcAMP (ranging in concentration as described herein), TGFβ3 and DAPT (ranging in concentration as described herein) until the desired maturation stage for a given experiment.

Example 8 iPSC Derivation and Differentiation

Apparently healthy young donor, old donor and HGPS patient and Parkinson's patient fibroblasts purchased from Coriell were reprogrammed as described (Fusaki et al., *Proc Japan Acad Ser B*:348-362 (2009)) using CytoTune Sendai viruses (Life Technologies) at an MOI of 10. iPSC clones were isolated approximately 4 weeks after infection with CytoTune and maintained on MEFs in pluripotent maintenance medium containing 10 ng/ml $FGF_2$ with weekly passaging using Dispase (STEMCELL Technologies). In preparation for differentiation, iPSCs were harvested using Accutase (Innovative Cell Technology). Fibroblast differentiations (Park et al., *Nature* 141-146 (2008)) and mDA neuron differentiations (Kriks et al., *Nature* 480:547-551 (2011)) were performed as previously described.

Example 9

Modified-RNA Synthesis and Viral Vector Construction

Modified-RNA was generated using an in vitro transcription (IVT) protocol described previously (Mandal et al., *Nat Protoc* 8:568-582 (2013)) and Warren et al., *Cell Stem Cell* 7:618-630 (2010)).

Briefly, the protocol for synthesizing modified-RNA coding for progerin entails:

1. Clone progerin open reading frame from cDNA from Hutchinson Gilford progeria syndrome (HGPS) fibroblasts.
2. Gel purify progerin-specific band (~1850 bp).
3. Flank the progerin ORF with a T7 promoter, 5'UTR sequences upstream and a 3'UTR sequence downstream through splint ligation or cloning with a synthetic RNA expression vector (Warren, et al *Cell Stem Cell* 7:618-630 (2010) and Suppl. DOI 10.1016/j.stem.2010.08.012).
4. Perform PCR to amplify T7-5'UTR-ORF-3'UTR sequence and purify product.
5. In vitro transcribe and PCR product and purify resulting modified RNA.

On the other hand, the protocol for synthesizing virus plasmid is the following:

1. Clone progerin open reading frame as above.
2. Gel purify progerin-specific band (~1850 bp).
3. Clone progerin ORF into lentiviral/retroviral/Sendai viral backbone with desired promoter.
4. For example, we pLenti-hSyn-eNpHR 3.0-EYFP (Addgene, plasmid 26775) can be used for expression in iPSC-derived dopamine neurons.
5. Produce virus using standard procedures and store at −80C.
6. Perform pilot experiment to determine the titer of the lentivirus using fluorescent protein expression or other means as a readout.

Transfections of modified RNA were performed in cell type-specific medium. Modified-RNA and Lipofectamine RNAiMAX® (Life Technologies) diluted in Opti-MEM (Gibco) were added.

Example 10

Immunocytochemical Analyses

Cells cultures were fixed in 4% paraformaldehyde for 15 minutes. Blocking was performed in phosphate-buffered saline supplemented with 1% BSA and 0.3% Triton X-100. A list of antibodies and concentrations is provided in Table 5. Secondary antibodies were species-specific Alexa dye conjugates (Molecular Probes). Additional details for mouse tissue as well as detailed quantification methods are described below.

These antibodies can be used for detecting chronological markers by techniques including electronic microscopy (EM); flow cytometry (FC); immunocytochemistry (ICC); IHC, immunohistochemistry (IHC); western blot (WB), among others.

TABLE 5

Chronological Marker-specific Antibodies

| Antigen | Company | Host | Concentration |
|---|---|---|---|
| p-4EBP1 | Cell Signaling | Rabbit | 1:1000 (WB) |
| 4EBP1 (total) | Cell Signaling | Rabbit | 1:1000 (WB) |
| p-AKT | Cell Signaling | Rabbit | 1:250 (WB) |
| AKT (total) | Cell Signaling | Rabbit | 1:1000 (WB) |
| CD13-PE | BD | | 20 µl per 1M cells (FC) |
| Cleaved caspase-3 | Cell Signaling | Rabbit | 1:100 (ICC) |
| FOXA2 | Santa Cruz | Goat | 1:200 (ICC) |
| GFP | Abcam | Chick | 1:2000 (WB, IHC) |
| GFP | Aves | Chick | 1:3000 (EM) |
| γH2AX | Millipore | Mouse | 1:250 (ICC) |
| H3K9me3 | Abcam | Rabbit | 1:4000 (ICC) |
| HLA-ABC-APC | BD | | 20 µl per 1M cells (FC) |
| HP1γ | Millipore | Mouse | 1:200 (ICC) |
| Ki67 | Dako | Mouse | 1:100 (ICC) |
| Lamin A | Abcam | Rabbit | 1:100 (ICC) |
| Lamin A/C (clone JOL2) | Abcam | Mouse | 1:200 (ICC) |
| Lamin A/C (clone N-18) | Santa Cruz | Goat | 1:100 (WB) |
| Lamin B2 | Abcam | Mouse | 1:500 (ICC) |
| Lamin C | Abcam | Rabbit | 1:100 (ICC) |
| LAP2α | Abcam | Rabbit | 1:500 (ICC) |
| LMX1A | Millipore | Rabbit | 1:2000 (ICC) |
| MAP2 | Sigma | Mouse | 1:200 (ICC) |
| NANOG | R&D | Goat | 1:50 (ICC) |
| Nestin | R&D | Mouse | 1:300 (ICC) |
| NURR1 | R&D | Mouse | 1:1000 (ICC) |
| OCT4 | Santa Cruz | Mouse | 1:200 (ICC) |
| Sendai | MBL Int. | Rabbit | 1:500 (ICC) |
| SSEA3-FITC | BD | | 20 µl per 1M cells (FC) |
| SSEA4-PE | BD | | 20 µl per 1M cells (FC) |
| Total AKT | Cell Signaling | Rabbit | 1:500 (WB) |
| TUJ1 | Covance | Mouse/ Rabbit | 1:500 (ICC) |
| Tyrosine hydroxylase (TH) | Pel-Freez | Rabbit | 1:500 (ICC, IHC, WB) |

Example 11

Flow Cytometry and Mitochondrial ROS Analyses

Cells were dissociated with Accutase and stained with directly conjugated antibodies (BD Biosciences) according to manufacturer-recommended concentrations for 1 hour on ice. For Mitochondrial ROS assessment, cells were stained with MitoSOX Red mitochondrial superoxide indicator (Life Technologies) according to manufacturer's instructions at a final concentration of 20 µM in cell culture medium. Cell sorting was performed on a FACSAria (BD Biosciences).

Example 12

Gene Expression Analysis

Cells were lysed with TriZol (Life Technologies). RNA was extracted using the RNeasy kit (Qiagen) and reverse transcribed using the Superscript kit (Life Technologies) according to the manufacturer's instructions. Quantitative RT-PCR was performed using the Mastercycler RealPlex2 (Eppendorf) platform. For RNA-seq, total RNA was isolated from two independent experiments and processed by the MSKCC Genomic core facility.

Example 13

Protein Analysis

Cell pellets were lysed with RIPA buffer with 1% sodium dodecyl sulfate (SDS). 20-40 μg samples were further diluted with 4× Laemmli sample buffer, boiled for 5 minutes at 95° C., and loaded onto a NuPAGE 4-12% Bis-Tris precast gel (Life Technologies) and transferred to PVDF membranes. Blots were incubated in primary antibodies overnight (see Table S4 for a list of antibodies used) followed by appropriate HRP-labeled secondary antibodies (Jackson ImmunoResearch).

Example 14

Xenografts iPSC-derived mDA neurons were transplanted into the striatum of lesioned NOD-SCID IL2Rgc-null mice (Jackson Laboratory) following in vitro infection of either hSyn::GFP-progerin or hSyn::nuclear-GFP lentivirus. Immunohistochemistry of the grafts was quantified using stereological analyses of cell numbers. Electron microscopy was performed 6 months following transplantation as previously described (Milner et al., *Methods Mol Biol* 793:23-59 (2011). A suitable commercially available lentivirus vector that can be used in this method is Deisseroth pLenti vector (Addgene #26775).

Example 15

Statistical Analyses

Distributions were compared by statistical analysis of corresponding cumulative distributions using Kolmogorov-Smirnov tests to analyze the difference between different ages or treatments. Bar graphs are plotted as mean±SEM and represent 3 biological replicates except where noted. Two-group comparisons were analyzed using Student t-tests. Multiple group comparisons against a control were analyzed using an ANOVA with Dunnett's test. Prism (version 6.0a, GraphPad) was used for data presentation and analysis.

Example 16

Generation and Characterization of iPSCs

Fibroblasts were purchased from Coriell (Camden, N.J.) and reprogrammed based on a protocol modified from Fusaki et al., *Proc Japan Acad Ser B:*348-362 (2009)) using CytoTune Sendai viruses expressing OCT4, SOX2, KLF4, and c-MYC (OSKM; Life Technologies, Carlsbad, Calif.). Briefly, fibroblasts were plated onto gelatin at 10,500 cells per cm2 per well of a 12-well plate in Minimal Essential Medium Alpha (Life Technologies) supplemented with 15% fetal bovine serum (Life Technologies). CytoTune viruses were combined at an MOI of 10 and added to the fibroblasts on the following day (notated as day 0) as well as on day 2 in some cases.

Medium was replaced approximately 16 hours after addition. On day 4 fibroblasts were harvested by trypsinization and reseeded at 10,500 cells per cm2 onto mitomycin C-treated mouse embryonic fibroblasts (MEFs; Global Stem, Rockville, Md.) in iPSC maintenance medium containing DMEM-F12, 20% knockout serum replacement (Life Technologies), L-glutamine, non-essential amino acids, β-mercaptoethanol, and 10 ng/ml FGF2 (R&D) supplemented with 10 μM Rhokinase inhibitor (Y-27632; Tocris, Bristol, UK) to support attachment. The medium was replaced every other day thereafter. Valproic acid (Sigma, St Louis, Mo.) was added to the medium at a final concentration of 1 mM from day 6 to day 13 to enhance the reprogramming efficiency as described previously (Huangfu et al., *In Nat Biotechnol* 1269-1275 (2008)).

In addition, the cells were cultured in 5% oxygen from 1 week prior to transduction through 2.5 weeks after transduction to further improve the likelihood of iPSC colony formation (Yoshida et al., *Cell Stem Cell* 237-241 (2009)). HGPS fibroblasts were also treated with rapamycin (Sigma) at 680 nM from 1 week prior to transduction until the first appearance of iPSC colonies in order to reduce HGPS phenotypes (Cao et al., *Science translational medicine* 3:89ra58 (2011)), which can act as a barrier to reprogramming. Approximately 30 days after transduction, colonies resembling human embryonic stem cell colonies were mechanically isolated and replated onto MEFs in 24-well plates. iPSC clones were picked from separately transduced wells in order to ensure independent reprogramming events. At least 3 surviving colonies from each starting fibroblast line were subsequently maintained on MEF feeder layers in iPSC medium and passaged approximately every week using dispase (STEMCELL Technologies, Vancouver, BC).

Karyotype analysis was performed by the MSKCC Molecular Cytogenetics core facility using standard G-banding procedures. Spontaneous differentiation via embryoid body formation was performed as described previously (Park et al., *Nature* 141-146 (2008)). Experiments using iPSCs were performed using 3 independent clones per fibroblast line. Cells (including those listed below) were regularly tested for mycoplasma every 2 to 4 weeks and found to be negative.

Example 17 iPSCs for PD Modeling

PD iPSCs generated by retroviral overexpression of OSKM from patients with mutations in PINK1 (c.1366C>T, p.Q456XStop) or PARK2/Parkin (c.1072Tdel, p.V324fsX110) were generously provided by the D. Krainc lab (Massachusetts General Hospital, Boston, Mass.). Apparently healthy iPSCs (C1, age 36; C2, age 48) also established using pMIG retroviruses (OSK, no c-Myc) were obtained from the K. Eggan lab (Harvard University, Cambridge, Mass.). Additional iPSC clones were derived using Sendai virus from fibroblasts from a patient with a different mutation in PARK2/Parkin (c.924C>T, p.R275W). Young (here called C3) and old (here called C4) iPSCs listed above were used as controls because they were also derived using Sendai virus reprogramming factors.

Example 18

Fibroblast Differentiation

Differentiation of iPSCs to fibroblast-like cells was based on a protocol from Park et al., *Nature* 141-146 (2008)). Briefly, iPSC clones were enzymatically passaged using dispase and plated as multicell clumps onto gelatin in iPSC maintenance medium that had been conditioned on MEFs for 24 hours and then supplemented with 10 ng/ml $FGF_2$ and 10 μM Y-27632. The next day the medium was replaced with Minimal Essential Medium Alpha (Life Technologies)

supplemented with 15% fetal bovine serum (Life Technologies) and continually changed every other day thereafter. The differentiating cells were carefully passaged every 5-6 days using Accutase (Innovative Cell Technology, San Diego, Calif.) for the first two weeks and then trypsinized subsequently. Y-27632 was added to the medium on the day of passaging to help support attachment. After four weeks fibroblast-like cells were sorted based on high expression levels of CD-13 and HLA-ABC prior to phenotype assessment and overexpression studies. Sorted cells were expanded in Minimal Essential Medium Alpha with 15% fetal bovine serum (no Y-27632) thereafter.

Example 19 mDA Neuron Differentiation

This example contains a longer version of the protocol of Example 3. A modified version of the dual-SMAD inhibition protocol was used to direct cells towards floor plate-based mDA neurons as described previously (Kriks et al., *Nature* 480:547-551 (2011)) and schematized in FIG. 8A.

iPSC-derived mDA neurons were replated on day 30 of differentiation at 260,000 cells per cm2 on dishes pre-coated with polyornithine (PO; 15 μg/ml)/Laminin (1 μg/ml)/Fibronectin (2 μg/ml) in Neurobasal/B27/L-glutamine-containing medium (NB/B27; Life Technologies) supplemented with 10 μM Y-27632 (until day 32) and with BDNF (brain-derived neurotrophic factor, 20 ng/ml; R&D), ascorbic acid (AA; 0.2 mM, Sigma), GDNF (glial cell line-derived neurotrophic factor, 20 ng/ml; R&D), TGFβ3 (transforming growth factor type β3, 1 ng/ml; R&D), dibutyryl cAMP (0.5 mM; Sigma), and DAPT (10 nM; Tocris).

One to two days after plating, cells were treated with 1 μg/ml mitomycin C (Tocris) for 1 hour to kill any remaining proliferating contaminants. iPSC-derived mDA neurons were fed every 2 to 3 days and maintained without passaging until the desired timepoint for a given experiment. PO, laminin and fibronectin were added to the medium every 7-10 days to prevent neurons from lifting off.

Example 20

Synthetic mRNA (Modified-RNA) Cloning, Synthesis and Use

This example contains the protocol of example 9. Modified-RNA was generated using an in vitro transcription (IVT) protocol described previously (Mandal et al., *Nat Protoc* 8:568-582 (2013)) and Warren et al., *Cell Stem Cell* 7:618-630 (2010)). The ORF for progerin was obtained by PCR from HGPS fibroblasts. The sequence of progerin ORF is listed as SEQ ID No. 1. N-terminal GFP fusion was achieved by inserting the progerin ORF into pAcGFP1-C using InFusion® cloning technology (Clontech, Mountain View, Calif.). The sequence of fused GFP-progerin ORF is listed as SEQ ID No. 2. Nuclear GFP was templated from pAcGFP1-Nuc (Clontech). Phosphorylated ORFs were cloned into a backbone already containing generic 5' and 3' UTRs. Tail PCR and IVT reactions were carried out as described previously (Mandal et al., *Nat Protoc* 8:568-582 (2013)).

For overexpression experiments, modified-RNA was thawed on ice and adjusted to a working concentration of 100 ng/μl. Per 100,000-cell transfection, 200 ng of modified-RNA was diluted up to 10 μl in Opti-MEM medium (Life Technologies), vortexed, and incubated at room temperature for 10 minutes. In a separate tube, 0.6 μl Lipofectamine RNAiMAX® (Life Technologies) was diluted up to 10 μl in Opti-MEM and incubated for the same timeframe. The Lipofectamine mixture was then transferred to the tube containing the modified-RNA mixture, vortexed and incubated for an additional 10 minutes. The transfection mixture was added dropwise to cells that had been pre-treated with 200 ng/ml of the interferon inhibitor B18R (eBioscience, San Diego, Calif.) for at least 4 hours prior to transfection.

After 4 hours at 37° C., the entire suspension was replaced with fresh medium supplemented with B18R. Transfection of iPSC-derived fibroblasts was performed starting on day 50 of differentiation and repeated on 2 consecutive days thereafter. iPSC-derived mDA neurons were transfected starting on day 65 or day 120 of differentiation and repeated on 4 consecutive days thereafter. The additional 2 days of transfections were done in order to establish a phenotype in iPSC-derived mDA neurons. Cells were analyzed one day after the final transfection.

Example 21

Immunostaining Cells

Cells were fixed in 4% paraformaldehyde for 15 minutes. Blocking was performed in phosphate-buffered saline supplemented with 1% BSA, and 0.3% Triton X-100 for 30 minutes to 1 hour. Cells were stained overnight at 4° C. with primary antibodies diluted in blocking buffer. A list of antibodies and concentrations is provided in Table S4. Following several washes, cells were stained with appropriate Alexa Fluor-labeled secondary antibodies (Molecular Probes, Carlsbad, Calif.) at 1:500 in blocking buffer for 30 minutes to 3 hours at room temperature. Cells were counterstained with 4',6-diamidino-2-phenylindole (DAPI; Thermo Fisher, Rockford, Ill.) to visualize nuclei. Images were acquired with an Olympus IX81 microscope using a Hamamatsu ORCA CCD camera.

Example 22

Mouse Tissue 3 months after transplantation of human iPSC-derived mDA neurons, mice received overdoses of Pentobarbital intraperitoneally (50 mg/kg) to induce deep anesthesia and were perfused in 4% paraformaldehyde (PFA). Brains were extracted, post-fixed in 4% PFA then soaked in 30% sucrose solutions for 2-5 days. The tissue was sectioned (30 μm) on a cryostat after embedding in O.C.T. (Sakura-Finetek, Torrance, Calif.). For treatment of mouse tissue for electron microscopy, see below.

Example 23

Immunostaining Quantification

In Vitro Cells

Images were acquired on an Operetta (PerkinElmer, Waltham, Mass.) using a 20× objective. Image processing was performed using Harmony high content analysis software (version 3.0).

Passage-matched cells were scored from three independent experiments. Where necessary due to bias against progerin-positive cells, images were processed using ImageJ software (version 1.43u, NIH). In these cases, 50 cells per condition were assessed for each independent experiment. Data are presented as mean±standard error of means (SEM).

In Vivo Mouse Brain Tissue

Cell counts were determined using the optical fractionator probe and the Cavalieri estimator using the Stereo Investigator software (MBF bioscience, Vermont) as described previously (Tabar et al., *In Nat Biotechnol* 23(5):601-606 (2005). Cell counts were scored on every fifth section where a graft was identifiable using a randomized grid. Counts were determined from three animals per condition. Data are presented as estimated total cell number±SEM.

Example 24

Assessment of Senescence

Senescence-activated beta-galactosidase was assessed using the staining kit from Cell Signaling according to the manufacturer's instructions. Positive cell staining was manually assessed (2 replicates, 50 cells each).

Telomere Length Measurements by HT-OFISH

Cells were plated on a clear-bottom, black-walled, 96-well plate, including 4 well replicates per sample, and high throughput quantitative fluorescence in situ hydridization (HT-QFISH) was performed as previously described (Canela et al., *Proc Natl Acad Sci USA* 104:5300-5305 (2007)). Images were captured with the Operetta using a 20× objective. Image processing was performed using Harmony high content analysis software. Telomere length values were measured using individual telomere spots corresponding to the specific binding of a Cy3-labeled telomeric probe (>600 spots per sample) in quadruplicate samples, fluorescence intensities were converted into kilobases using control cell lines of known telomere length as described previously (Canela et al., *Proc Natl Acad Sci USA* 104:5300-5305 (2007) and McIlrath et al., *Cancer research* 61: 912-915 (2001)).

Example 25

Flow Cytometry

Cells were dissociated with Accutase and stained with directly conjugated antibodies (BD Biosciences, San Jose, Calif.) according to manufacturer-recommended concentrations for 1 hour on ice. Cell sorting was performed on a FACSAria (BD Biosciences).

Mitochondrial ROS Assessment

Cells were dissociated with Accutase and stained with MitoSOX Red mitochondrial superoxide indicator (Life Technologies) at a final concentration of 20 μM in cell culture medium. Staining was carried out in a 37° C. incubator for 30 minutes. Cells were washed and resuspended in cell culture medium containing DAPI to exclude dead cells from the analysis. In order to prevent positive staining due to cell shock, reagents used were pre-warmed to 37° C. and samples were kept at 37° C. until just prior to analysis on a FACSAria. Samples were always compared to untreated young donor fibroblasts/iPSC-derived fibroblasts/iPSC-derived mDA neurons as well as the young donor cells treated with 20 μM carbonyl cyanide 3-chlorophenylhydrazone (CCCP; Sigma) for 48 hours to induce mitochondrial superoxide production. These controls helped to ensure that the reagent had not become oxidized over time and that the cells were not stressed during the staining protocol. Quantification of the percent of the population that oxidized the MitoSOX reagent was performed using FlowJo software (version 9.5.3; Tree Star) and averaged for at least three independent clones or experiments per condition. Data from an individual experiment were excluded from analysis when the negative control sample gave an entirely positive reading by flow cytometry, suggesting that the conditions or the reagent itself were compromised.

Example 26

DNA Extraction and Mutation Analysis

Genomic DNA was extracted from cell pellets using the DNeasy blood and tissue kit (Qiagen). A small region around the mutation was PCR amplified using HiFi Hotstart (KAPA Biosystems) per the manufacturer's instructions. PCR products were cleaned up using standard phenol/chloroform extraction and ethanol precipitation. DNA sequencing of PCR products was performed by the MSKCC DNA Sequencing core facility or GENEWIZ (South Plainfield, N.J.).

Example 27

RNA Extraction and Gene Expression Analysis

Cells were lysed directly in Trizol (Life Technologies). RNA was extracted using chloroform and ethanol precipitation and further cleaned using the RNeasy kit (Qiagen). Samples were stored at −80° C. until further processing. Total RNA was reverse transcribed (Superscript, Life Technologies) and 50 ng of RNA was used to template each RT-PCR reaction. For analysis of progerin expression levels, total RNA was hydrolyzed by 0.1× volume 5 M NaOH for 30 minutes at room temperature followed by 0.1× volume 5 M HCl (Scaffidi et al., *Science* 312:1059-1063 (2006)). Quantitative RT-PCR was performed using the Mastercycler RealPlex2 (Eppendorf, Hauppauge, N.Y.) platform following the manufacturer's instructions. Expression levels were normalized to cyclophillin A or 18S (housekeeping gene controls) as noted. For RNA-seq, total RNA was isolated from two independent experiments and processed by the MSKCC Genomic core facility.

The sequence of primers used in the RT-PCR experiments and the sequence of primers for sequencing are listed in Table 6.

TABLE 6

Sequences of Primers Used for Sequencing, PCR Analysis and RNA Generation

| Name | Application | Sequence (5' → 3') | Reference |
|---|---|---|---|
| cyclophilin A | qRT-PCR (SYBR) | F: GTCAACCCCACCGTGTTCTT (SEQ ID NO: 3)<br>R: CTGCTGTCTTTGGGACCTTG T (SEQ ID NO: 4) | |

TABLE 6-continued

Sequences of Primers Used for Sequencing, PCR Analysis and RNA Generation

| Name | Application | Sequence (5' → 3') | Reference |
|---|---|---|---|
| GFP-progerin ORF | Modified RNA cloning | F: P-TGGTGAGCAAGGGCGCCG AGCTG (SEQ ID NO: 5)<br>R: P-TTACATGATGCTGCAGTT CTG (SEQ ID NO: 6) | |
| lamin A | qRT-PCR (SYBR) | F: GCTCTTCTGCCTCCAGTGTC (SEQ ID NO: 7)<br>R: ACATGATGCTGCAGTTCTGG (SEQ ID NO: 8) | |
| lamin C | qRT-PCR (SYBR) | F: CTCAGTGACTGTGGTTGAGG A (SEQ ID NO: 9)<br>R: AGTGCAGGCTCGGCCTC (SEQ ID NO: 10) | |
| LMNA | Mutation sequencing | F: CTGAGCCTTGTCTCCCTTCC (SEQ ID NO: 11)<br>R: none | |
| LMNA exons 9-12 | RT-PCR | F: GTGGAAGGCACAGAACACCT (SEQ ID NO: 12)<br>R: GTGAGGAGGACGCAGGAA (SEQ ID NO: 13) | (Scaffidi and Misteli, 2006) |
| nuclear-GFP ORF | Modified RNA cloning | F: P-TGGTGAGCAAGGGCGCCG AGCTG (SEQ ID NO: 5)<br>R: P-TTATCTAGATCCGGTGGA TCCTACC (SEQ ID NO: 14) | |
| Parkin (c.1366C > T) | Mutation sequencing | F: GAAACTGGTTAAGCAAGAAA TCC (SEQ ID NO: 15)<br>R: none | |
| PINK1 (c.1072delT) | Mutation sequencing | F: TGTGCAGGACATGAAAAGGT (SEQ ID NO: 16)<br>R: none | |
| progerin | qRT-PCR (SYBR) | F: GCGTCAGGAGCCCTGAGC (SEQ ID NO: 17)<br>R: GACGCAGGAAGCCTCCAC (SEQ ID NO: 18) | |
| progerin ORF | Cloning into pAcGFP1-C | F: aaggcctctgtcgacAGCAG TCTCTGTCCTTCGACCC (SEQ ID NO: 19)<br>R: agaattcgcaagcttCTTCC ACCTCCCACCTCATTCC (SEQ ID NO: 20) | |
| Tail PCR | Modified RNA cloning | F: TTGGACCCTCGTACAGAAGC TAATACG (SEQ ID NO: 21)<br>R: (Tx120)CTTCCTACTCAGG CTTTATTCAAAGACCA (SEQ ID NO: 22) | (Warren et al., 2010) |

Paired-end 75 base pair RNA-sequencing libraries were sequenced on an Illumina HiSeq2000. Reads were mapped to the human genome (Hg19) using STAR 2.3.0e (Dobin et al., *Bioinformatics* 29:15-21 (2013) with default mapping parameters and read counts were assessed using HTSeq. Principal component analysis was completed in R (v2.15.2) using the base "stats" package. Differentially expressed genes were identified with limma voom (Smyth, *Stat Appl Genet Mol Biol* 3:Article3 (2004)). A conservative approach was taken to account for low coverage in the sequencing library; a low read count filter was used such that samples contained non-zero read counts for a gene to be assessed in limma. Differentially expressed genes were identified using a fold change cut off of +/−2 and a Bonferroni adjusted p value of 0.05. A hypergeometric test was used to assess the similarity in response to progerin overexpression in young donor and old donor iPSC-derived mDA neurons. Gene ontology analysis was completed using iPAGE (Goodarzi et al., *Mol Cell* 36:900-911 (2009)) with the fold change between nuclear-GFP and GFP-progerin expressing iPSC-derived mDA neurons as a continuous variable across 10 bins. Venn-diagrams, barplots, and PCA plots were generated in R (v2.15.2) using the base R 'ggplot2' graphics packages (Wickham, H. (2009). ggplot2: elegant graphics for data analysis (Springer New York)). Raw data are available on Gene expression omnibus ncbi.nlm.nih.gov/geo/ (GSE49112).

Example 28

Protein Isolation and Western Blot Analysis

Cells were collected with a cell lifter (Corning, Tewksbury, Mass.) in ice-cold phosphate-buffered saline without calcium or magnesium (PBS−/−). Cell pellets were rapidly frozen on ethanol and dry ice and stored at −80° C. Cell pellets were thawed on ice and resuspended in 50-200 μl RIPA lysis buffer (50 mM Tris-HCl pH 8.0, 120 mM NaCl, 6 mM EDTA, 0.5% NP-40) with 1% sodium dodecyl sulfate (SDS). Cell suspensions were vortexed at 15-minute intervals during a 45-minute incubation on ice. Lysates were isolated following a 10,000 rpm spin for 10 minutes at 4° C. 20-40 μg samples were further diluted with 4× Laemmli sample buffer, boiled for 5 minutes at 95° C., and loaded onto a NuPAGE 4-12% Bis-Tris precast gel (Life Technologies). Gel electrophoresis was performed at 100 V for 2 hours. Gels were transferred to a methanol activated PVDF membrane using the XCell II Blot Module (Life Technologies) according to the manufacturer's instructions. Blots were blocked in 3% bovine serum albumin (BSA) in Tris buffered saline plus 0.1% Tween-20 (TBS-T) for 45 minutes at room temperature. Blots were incubated in primary antibodies overnight at 4° C. on shaker (see Table S4 for a list of antibodies used).

Following several washes with TBS-T, blots were incubated in appropriate HRP-labeled secondary antibodies (Jackson ImmunoResearch, West Grove, Pa.) for 1 hour at room temperature. Visualization of protein bands was performed using Western Lightning Plus-ECL (PerkinElmer, Melville, N.Y.) according to the manufacturer's instructions and developed on an SRX-101A x-ray film processor (Konica Minolta, Wayne, N.J.). Densitometry quantification was performed using ImageJ on blots from three independent experiments.

Example 29

Neurite Quantification

Following immunostaining with MAP2 to label dendrites, randomly chosen images of GFP+ cells were manually acquired on an Olympus IX81 microscope using a Hamamatsu ORCA CCD camera using a 40× objective. Dendrite lengths were measured using ImageJ to trace each labeled neurite extending from GFP+ nuclei. Cells with perinuclear MAP2 staining were given a zero. GFP+ nuclei without MAP2 staining as well as cells with condensed GFP+ nuclei were not scored. Fifty cells per condition were assessed for each of three independent differentiations.

Example 30

In Vivo Assessment

Transplantation

Animal procedures were performed following NIH guidelines and were approved by the local Institutional Animal Care and Use Committee (IACUC), the Institutional Biosafety Committee (IBC) as well as the Embryonic Stem Cell Research Committee (ESCRO). Six-week-old NODSCID IL2Rgc-null mice (20-35 g; Jackson Laboratory, Bar Harbor, Me.) were anesthetized with Ketamine (90 mg/kg; 0, Decatur, Ill.) and Xylazine (4 mg/kg Fort Dodge, Iowa). 10 μg 6-hydroxydopamine (6-OHDA (Sigma-Aldrich) was injected stereotactically into the striatum of 6-week-old mice at the following coordinates (in millimeters): AP, 0.5 (from bregma); ML, −2.0; DV, −3.0 (from dura).

Two weeks after lesioning, mice were tested twice (1 week apart) for rotational behavior (see below). Animals were divided into six groups so that those demonstrating high/low rotations were evenly distributed among the groups and then randomly assigned to a particular group. An initial sample size of 5 animals per condition was chosen to allow for analysis of at least 3 animals per group at the 3-month timepoint. Control (C1) and PD mutant (PINK1-Q456X, Parkin-V324A) iPSCderived mDA neurons were infected with lentiviral vectors expressing either hSyn::GFP-progerin or hSyn::nuclear-GFP on day 21 of differentiation and transplanted on day 30 (animals approximately 2.5-months-old at time of transplantation). A total of $200\times10^3$ cells were injected in a volume of 2 μl into the striatum at the following coordinates (in mm): AP, 0.5; ML, −1.8; DV, 3.2.

Rotation Testing

Amphetamine-induced rotation testing was performed before transplantation and 12 after transplantation. Rotation behavior in mice was recorded 10 min after i.p. injection of d-amphetamine (10 mg/kg, Sigma) and recorded for 30 minutes. The data were presented as the average number of rotations per minute.

Example 31

Electron Microscopy

Procedures were performed according to (Milner et al., *Methods Mol Biol* 793:23-59 (2011)). Briefly, six months following transplantation of human iPSC-derived mDA neurons, mice were overdosed with 150 mg/kg sodium pentobarbital intraperitoneally. The brains were fixed by aortic arch perfusion sequentially with normal saline (0.9%) containing 1000 units/ml of Heparin, 50 ml of 3.75% acrolein and 2% paraformaldehyde in 0.1 M phosphate buffer (PB, pH 7.4), and 200 ml of 2% PFA in PB. The brains were removed and post-fixed with 1.87% acrolein/2% PFA in PB for 30 minutes at room temperature. Coronal tissue blocks were sectioned (40 μm) on a vibrating microtome (Leica Microsystems, Deerfield, Ill.). Selected sections containing the xenograft were pretreated in 1% sodium borohydride. Non-specific binding was blocked with 0.5% BSA 0.1 M Tris-saline (TS, pH 7.6). Primary antibodies (see Table S4) were diluted in 0.1% BSA in TS and incubated overnight at 4° C. Sections were incubated with a biotinylated secondary antibody (Jackson ImmunoResearch, West Grove, Pa.) for 30 minutes at room temperature. Peroxidase labeling was performed using the Vectastain ABC kit (Vector Laboratories, Burlingame, Calif.) followed by incubation with diaminobenzidine for 7 minutes. Sections were then incubated in gold-conjugated secondary antibody (Electron Microscopy Sciences (EMS), Fort Washington, Pa.) overnight at 4° C. Sections were post-fixed in 2% glutaraldehyde, washed in 0.2 M citrate buffer (pH 7.4), and silver intensified using the Silver IntenSE M kit (GE Healthcare, Piscataway, N.J.). Following several washes, sections were fixed in 2% osmium tetroxide for 1 hr, dehydrated through an ascending ethanol series, and placed in propylene oxide/EMBed 812 (EMS) overnight. Sections were then embedded in EMBed 812 between two sheets of Aclar plastic at 60° C. for 4 days. Selected sections containing the graft were glued on Beem capsules and cut on an ultramicrotome (Ultracut) using a glass knife (Leica). Ultrathin sections were collected on grids and counterstained with uranyl acetate and Reynold's lead citrate. Final preparations were examined and photographed using a Phillips C10 transmission electron microscope. The number of TH-immunogold particles per $\mu m^2$ in 25 dendrites per group and the area ($\mu m^2$) quantification of 25 mitochondria per group were performed using ImageJ.

Example 32

Statistical Analysis

Frequency distribution plots display the fluorescence intensity quantification of 100 cells (fibroblasts) or 50-100 cells from each of 3 independent experiments (all others) binned by 50 or 100 arbitrary unit increments. Distributions were compared by statistical analysis of corresponding cumulative distributions using Kolmogorov-Smirnov tests to analyze the difference between different ages or treatments. Arbitrary units for frequency distributions of different cell types should not be compared because staining was performed at different times.

Bar graphs are plotted as mean±SEM and represent 3 biological replicates except where noted. Technical replicates were averaged prior to being included in statistical analysis (i.e., average of technical replicates for 1 experiment=1 biological replicate). Two-group comparisons were analyzed using Student t-tests. Multiple group comparisons against a control were analyzed using an ANOVA with Dunnett's test. Prism (version 6.0a, GraphPad) was used for data presentation and analysis.

Example 33

Reprogramming Reverts Age Associated Markers to a "Young" State

In order to validate a marker profile that could be followed during reprogramming and redifferentiation, a comparison of 12 fibroblast populations, matched for passage number, from apparently healthy young donors (age 11), middle-aged donors (ages 31-55), old donors (ages 71-96), and prematurely aged HGPS patients (ages 3-14) was performed. A significant correlation was observed between donor fibroblast age with various age-associated markers (FIGS. 2A-2C and FIG. 5A) including markers previously described in HGPS fibroblasts (Scaffidi et al., *Science* 312:1059-1063 (2006)).

Figures 2A, 2B, 2C, 2D, 2E, 2F:
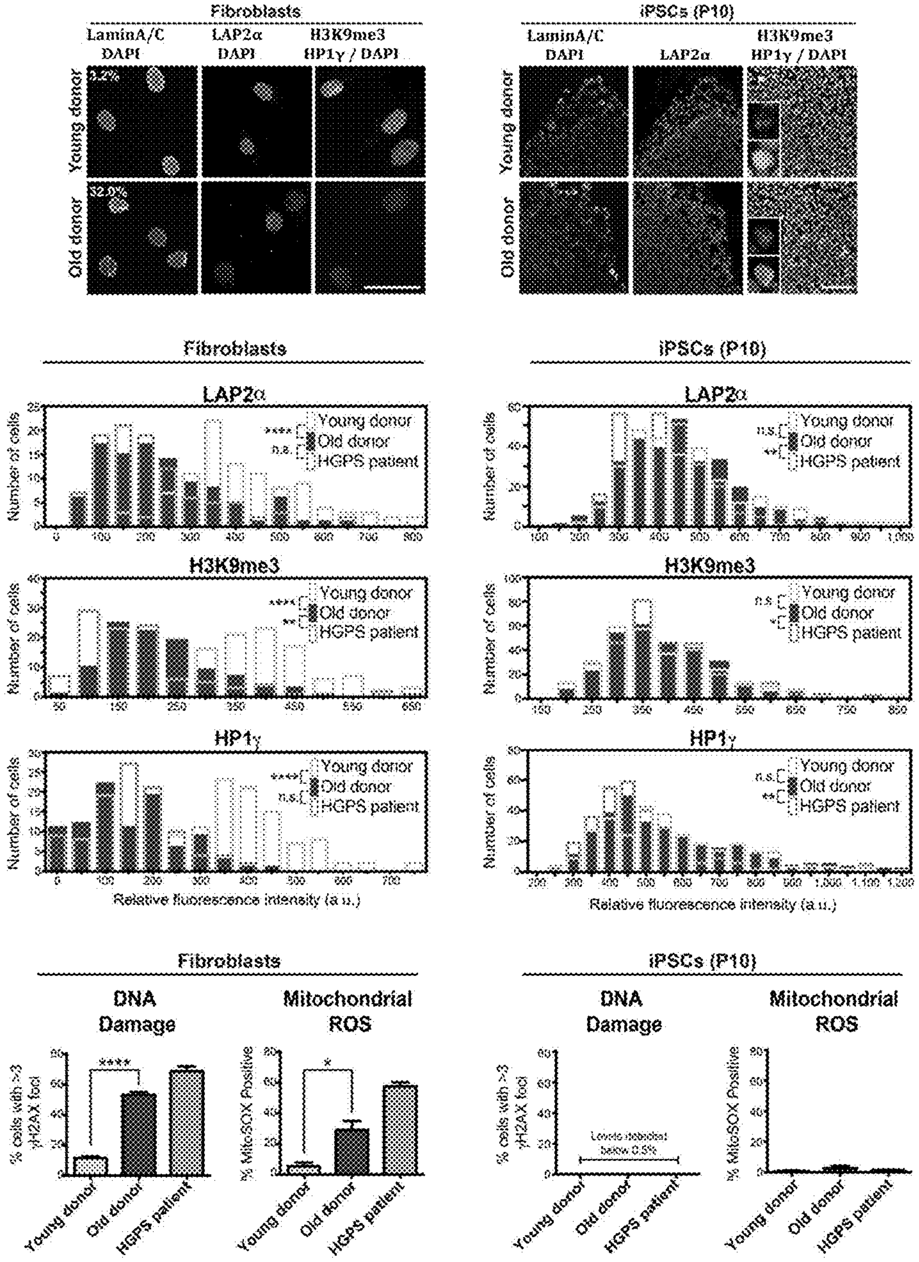
FIG. 2A-2F presents exemplary data showing that old donor fibroblasts lose age-associated markers following reprogramming to the pluripotent state. (A) Immunocytochemistry for markers identifying the nuclear lamina (Lamin A/C), a lamin A-associated protein (LAP2α) and peripheral heterochromatin (H3K9me3, HP1γ) in young fibroblasts from an 11-year-old donor compared to old fibroblasts from an 82-year-old donor. Percentages indicate the proportion of cells with folded and/or blebbed nuclear morphologies. (B) Quantification of the markers depicted in (A) demonstrates the ability of the selected age associated markers to stratify young and old donor fibroblasts and the similarity of old donor fibroblasts to HGPS patient fibroblasts that are prematurely aged. The data are plotted as frequency distributions of relative fluorescence intensity for 100 cells from single fibroblast lines that were passage-matched. a.u., arbitrary units. (C) Similar to HGPS patient fibroblasts, old donor fibroblasts have higher levels of DNA damage (as measured by γH2AX immunocytochemistry) and higher levels of mitochondrial reactive oxygen species (ROS; as measured by flow cytometry using the superoxide indicator MitoSOX) than young donor fibroblasts. n=3 independent experiments. (D) Immunocytochemistry for age-associated markers in passage 10 (P10) iPSCs derived from the young and old donor fibroblasts. (E) Quantification of staining in (D) indicates an inability of old donor-derived iPSCs to retain age-associated markers through reprogramming (similar to HGPS-derived iPSCs). n=300 cells each (100 cells from 3 independent iPSC clones). (F) DNA damage and mitochondrial superoxide levels are reset upon reprogramming. n=3 independent clones. n.s. not significant, *p<0.05, p<0.01, **p<0.0001 according to Kolmogorov-Smirnov tests (B and E) or Student's t tests (C and F). Bar graphs represent mean±SEM. Scale bars: 50 μm (A), 100 μm (C).

Immunocytochemistry was performed for markers identifying the nuclear lamina (Lamin A/C), a lamina-associated protein (LAP2α), and peripheral heterochromatin (H3K9me3, HP1γ) in young fibroblasts from an 11-year-old donor compared to old fibroblasts from an 82-year-old donor. Percentages indicate the proportion of cells with folded and/or blebbed nuclear morphologies. FIG. 2A. Quantification of the markers in FIG. 2A demonstrated the ability of the selected age-associated markers to stratify young and old donor fibroblasts and the similarity of old donor fibroblasts to HGPS patient fibroblasts that are prematurely aged. The data are plotted as frequency distributions of relative fluorescence intensity for 100 cells from single fibroblast lines that were passage-matched. FIG. 2B. Similar to HGPS patient fibroblasts, old donor fibroblasts have higher levels of DNA damage (as measured by γH2AX immunocytochemistry) and higher levels of mitochondrial reactive oxygen species (ROS; as measured by flow cytometry using the superoxide indicator MitoSOX) than young donor fibroblasts. n=3 independent experiments. FIG. 2C. Immunocytochemistry for age-associated markers in passage 10 (P10) iPSCs derived from the young and old donor fibroblasts. FIG. 2D. Quantification of staining in FIG. 2D indicated an inability of old donor-derived iPSCs to retain age-associated markers through reprogramming (similar to HGPS-derived iPSCs). n=300 cells each (100 cells from 3 independent iPSC clones). FIG. 2E. DNA damage and mitochondrial superoxide levels are reset upon reprogramming.

Figure 5A:
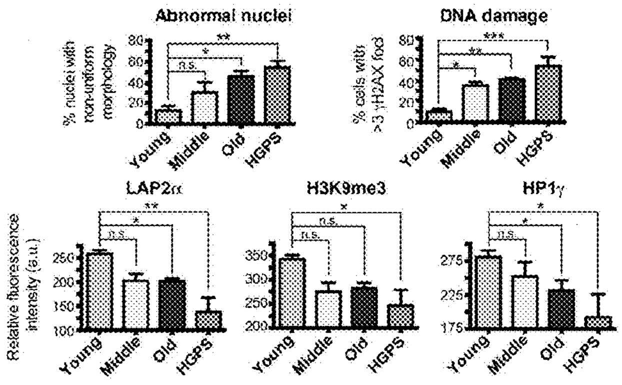
FIG. 5A-5G presents exemplary data showing characterization of fibroblasts and iPSCs. Assessment of age-associated markers across several primary fibroblast lines from donors of various ages is presented. Induction of pluripotency is schematized and characterization of resulting iPSC clones is shown. (A) Quantification of immunocytochemical analysis of markers that demonstrate age-associated changes in fibroblasts from donors of different ages. Young: all age 11, middle: ages 31-55, old: ages 71-82, HGPS (Hutchinson-Gilford progeria syndrome): ages 3-14. n=3 independent donors per age group. See Table S1 for additional fibroblast line information. (B) Quantitative RT-PCR analysis for each LMNA isoform in young donor (age 11), old donor (age 82) and HGPS patient (age 14) fibroblasts. Data are presented as mean±SEM. n=3 consecutive passages. (C) Reprogramming timeline. HGPS patient fibroblasts required rapamycin treatment to increase progerin turnover and thus reduce the negative effects of progerin-induced phenotypes (Cao et al., *Science translational medicine* 3:89ra58 (2011)) on reprogramming efficiency. OSKM, OCT4/SOX2/KLF4/c-MYC; MEF, mouse embryonic fibroblasts; VPA, valproic acid. (D) Two representative iPSC clones demonstrated expression of the pluripotency markers NANOG and OCT4 similar to H9 human embryonic stem cells (hESCs) as well as no signs of residual Sendai expression by passage 10. (E) Flow cytometry analysis of iPSCs for pluripotent (SSEA4, top) and fibroblast (HLA-ABC, bottom) surface markers. Two representative iPSC clones per donor as well as the donor fibroblasts were compared to H9 hESCs. (F) Spontaneous differentiation of iPSC clones into three-dimensional embryoid body (EB) structures demonstrates the potential for iPSC clones to upregulate markers of the three germ layers (endoderm: GATA4, AFP; mesoderm: RUNX1, BRACHYURY; ectoderm: NESTIN, NCAM). Images depict representative EBs derived from a single iPSC clone. (G) Sequencing results show maintenance of the 1824C>T heterozygous mutation through reprogramming in HGPS iPSCs, which was not present in apparently healthy young and old donor-derived fibroblasts or iPSCs. n.s. not significant, $*p<0.05$, $p<0.01$, $*p<0.001$ according to ANOVA with Dunnett's tests for multiple comparisons. Bar graphs represent mean±SEM. Scale bars: 200 μm.
Figure 5B:
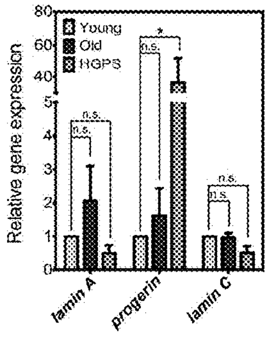

Fibroblasts from old donors closely resembled HGPS fibroblasts supporting previous findings by Misteli and colleagues (Scaffidi et al., *Science* 312:1059-1063 (2006), Scaffidi et al, *In Nat Med* 11(4):440-445 (2005)). More specifically, old donor fibroblasts showed nuclear morphology abnormalities (i.e., folding and blebbing), loss of nuclear lamina-associated proteins such as LAP2α, global loss of the peripheral heterochromatin markers tri-methylated H3K9 (H3K9me3) and heterochromatin protein 1 gamma (HP1γ), as well as an increase in DNA damage and mitochondrial superoxide levels when compared to fibroblasts from younger donors. Marker expression in old donor fibroblasts was comparable to HGPS fibroblasts despite expressing low levels of progerin, the mutant protein involved in HGPS (FIG. 5B). These data suggest that chronological marker signatures can faithfully stratify young versus old donor fibroblasts derived from apparently healthy donors.

Figure 5C:
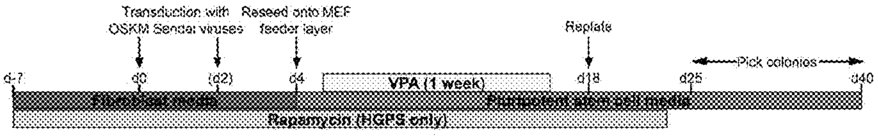
Figure 5D:
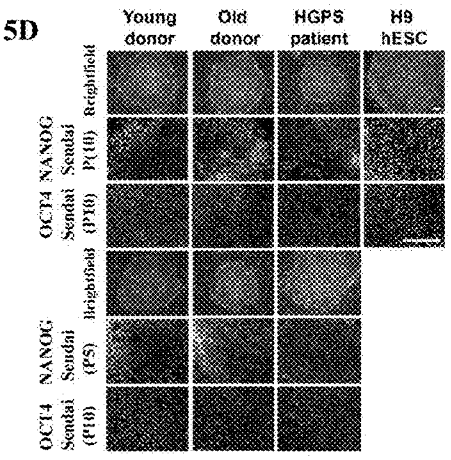
Figure 5E:
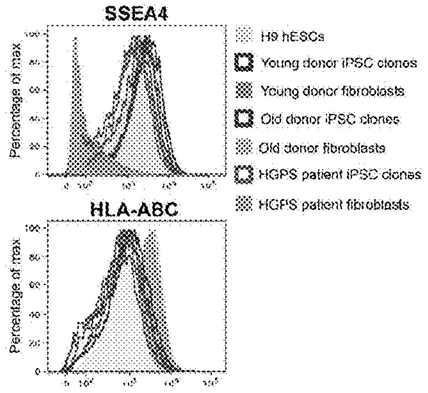
Figure 5F:
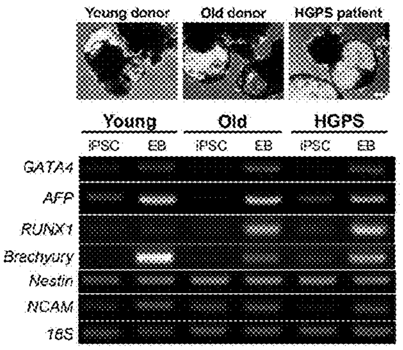
Figure 5G:
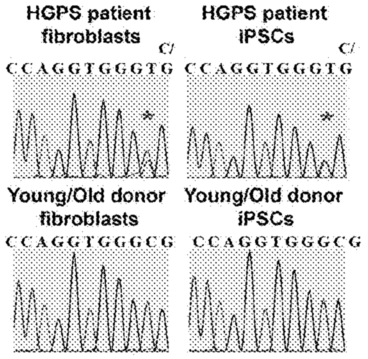

To address the effects of reprogramming on markers of cellular age, fibroblasts were selected from young (age 11), old (age 82), and HGPS (age 14) donors and transduced each of the donor fibroblast lines with Sendai vectors expressing Oct4, Sox2, Klf4 and c-Myc (Fusaki et al., *Proc Japan Acad Ser B:*348-362 (2009)) (FIG. 5C). The use of the cytoplasmic RNA viruses allowed for the derivation of integration-free iPSCs by 25-40 days post transduction. iPSC clones demonstrated properties characteristic of pluripotent cells including expression of nuclear (FIG. 50) and cell surface (FIG. 5E) pluripotency markers and differentiation into the three germ layers following embryoid body differentiation (FIG. 5F).

iPSC clones had a normal karyotype, and iPSCs derived from HGPS patient fibroblasts maintained the disease mutation (FIG. 5G). A subset of age-associated molecular markers shown above was assessed to distinguish between young and old fibroblasts. iPSCs were not assessed prior to passage to ensure loss of the exogenous Sendai virus (FIG. 5D). Following reprogramming, iPSCs which were derived from old donor fibroblasts were indistinguishable from young donor-derived iPSCs with respect to expression of lamin A, LAP2α, H3K9me, and HP1γ(FIGS. 2D and 2E). Furthermore, iPSCs displayed very little if any DNA damage or mitochondrial reactive oxygen species (FIG. 2F), suggesting a reset of phenotypic age at the pluripotent cell stage. However, it has been suggested that the age-associated signature is dependent on progerin expression (Scaffidi et al., *Science* 312:1059-1063 (2006)).

Quantification of immunocytochemical analysis of markers that demonstrate age-associated changes in fibroblasts from donors of different ages. Young donor: age 11, middle age donor: ages 31-55, old age donor: ages 71-82, HGPS (Hutchinson-Gilford progeria syndrome): donor ages 3-14. n=3 independent donors per age group. FIG. 5A. Quantitative RT-PCR analysis for each LMNA isoform in young donor (age 11), old donor (age 82) and HGPS patient (age 14) fibroblasts. Data are presented as mean±SEM. n=3 consecutive passages. FIG. 5B. HGPS patient fibroblasts with rapamycin treatment increased progerin turnover and thus reduced the negative effects of progerin-induced phenotypes (Cao et al., *Science translational medicine* 3:89ra58

(2011)) on reprogramming efficiency. OSKM, OCT4/SOX2/KLF4/c-MYC; MEF, mouse embryonic fibroblasts; VPA, valproic acid. FIG. 5C. Two representative iPSC clones demonstrated expression of the pluripotency markers NANOG and OCT4 similar to H9 human embryonic stem cells (hESCs) as well as no signs of residual Sendai expression by passage 10. FIG. 5D. Flow cytometry analysis of iPSCs for pluripotent (SSEA4, top) and fibroblast (HLA-ABC, bottom) surface markers. Two representative iPSC clones per donor as well as the donor fibroblasts were compared to H9 hESCs. Spontaneous differentiation of iPSC clones into three-dimensional embryoid body (EB) structures demonstrates the potential for iPSC clones to upregulate markers of the three germ layers (endoderm: GATA4, AFP; mesoderm: RUNX1, BRACHYURY; ectoderm: NESTIN, NCAM). Images depict representative EBs derived from a single iPSC clone. FIG. 5F. Sequencing results show maintenance of the 1824C>T heterozygous mutation through reprogramming in HGPS iPSCs, which was not present in apparently healthy young donor and old donor-derived fibroblasts or iPSCs. n.s. not significant, *$p<0.05$, $p<0.01$, *$p<0.001$ according to ANOVA with Dunn. FIG. 5F.

Therefore, the absence of an age-associated phenotype in iPSCs may simply reflect the fact that pluripotent cells do not express significant levels of A-type lamins including progerin (Constantinescu et al., *STEM CELLS* 24: 177-185 (2006)). Immunocytochemical analysis for A-type lamin isoforms showed expression restricted to cells that undergo spontaneous differentiation at the periphery of the iPSC colonies (FIG. 2D, left column). HGPS-iPSCs demonstrated a comparable loss of age-associated markers at the pluripotent stage (FIGS. 2B-C and 2E-F). However, the present data does not rule out the possibility that reprogramming selects for a cell with low levels of age-related marker expression (a "young" cell) among the old donor fibroblast population rather than truly re-setting age. Interestingly, clonal growth of primary donor fibroblasts resulted in cultures that within two weeks reestablished a similar distribution of age-related markers as the original fibroblast population maintained as bulk cultures. Nevertheless, regardless of the mechanism, the present results demonstrate that iPSCs, independent of donor age or HGPS status, lack expression of age-associated markers.

Example 34

Age is not Re-Induced after Differentiating iPSCs Derived from Old Donors

Figure 6A:
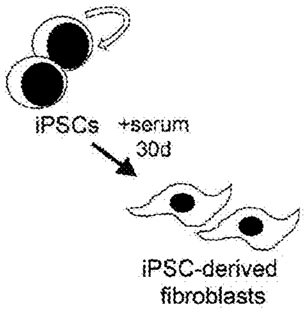
FIG. 6A-6H presents exemplary data showing that differentiation of iPSCs to fibroblast-like cells and overexpression of progerin using modified-RNA causes the appearance of age-related markers. (A and B) iPSCs were differentiated to fibroblast-like cells in serum-containing medium for 30 days (A) and sorted by flow cytometry (B) for high levels of expression of the fibroblast markers CD13 and HLA-ABC (red box) as compared to iPSCs. (C) iPSC-derived fibroblasts after sorting displayed fibroblast-like morphologies and expression of vimentin but no nestin (a neural marker) by immunocytochemistry. (D) RT-PCR for lamin A and progerin transcripts showed upregulation in iPSC-derived fibroblasts (iPSC-fibroblasts) to similar levels observed in the donor fibroblasts. (E) Modified-RNA was designed to express either nuclear-localized green fluorescent protein (nuclear-GFP) as a control or progerin fused to GFP (GFP-progerin). The addition of generic 5' and 3' UTRs as well as a Poly(A) tail and 5' cap structure facilitated the in vitro transcription reaction (Mandal et al., *Nat Protoc* 8:568-582 (2013); Warren et al., *Cell Stem Cell* 7:618-630 (2010). (F) Western blot analysis of transgene expression. n, nuclear-GFP; p, GFP-progerin. Analysis of detection using a lamin A/C antibody (N-18) revealed that progerin overexpression induces levels higher than the endogenous progerin level observed in HGPS iPSC-derived fibroblasts (arrows). (G) Quantification of telomere length and the percentage of telomeres less than 2 kilobases (kb) by Q-FISH. n=4 replicate wells. (H) Assessment of the senescence markers senescence-activated beta-galactosidase (SA-β-Gal) at all stages from the primary fibroblasts to iPSC-derived fibroblasts overexpressing progerin. n=2 replicate wells. n.s. not significant, $*p<0.05$ according to Student's t-tests. Bar graphs represent mean±SEM. Scale bar: 200 μm.
Figure 6B:
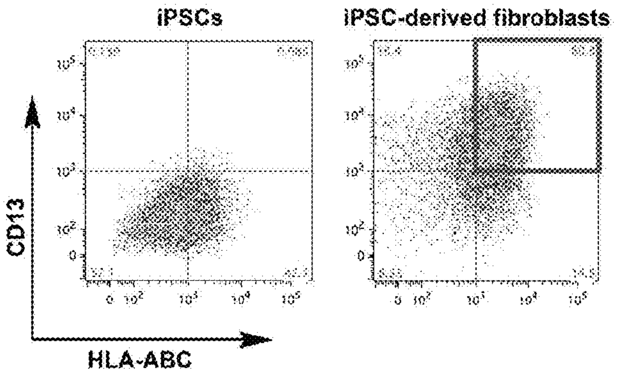
Figure 6C:
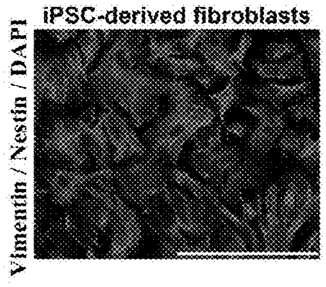
Figure 6D:
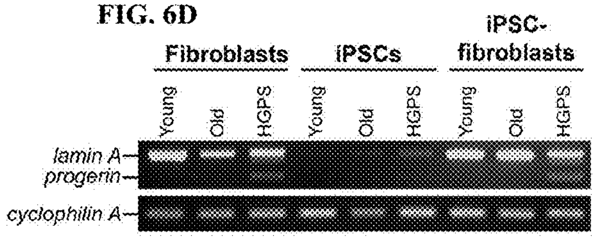
Figure 6E:
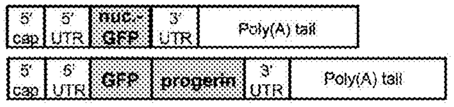
Figure 6F:
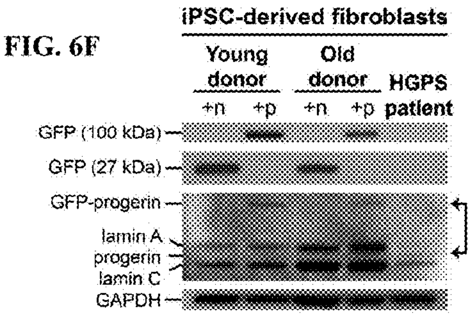
Figure 6G:
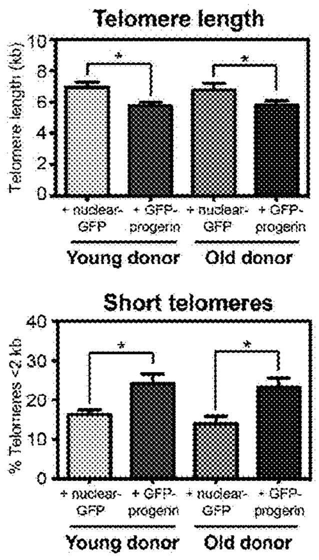
Figure 6H:
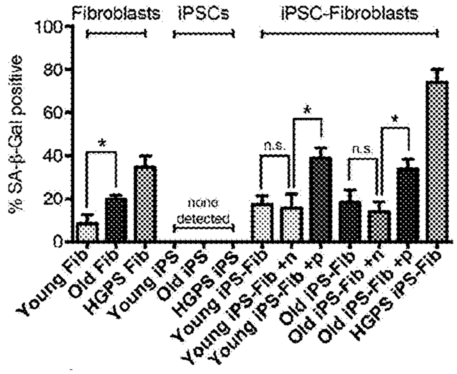

Old donor-derived iPSCs were tested to determine memory retention of their donor age that is transiently suppressed at the pluripotent stage through loss of lamin A/progerin.

iPSCs derived from fibroblasts were differentiated into fibroblast-like cells using serum-containing medium (FIG. 6A) for 30 days followed by fluorescence-activated cell sorting (FACS) for CD13+/HLA-ABC$^{hi}$ (Papapetrou et al., *Proc Natl Acad Sci U.S.A* 106:12759-12764 (2009); Verlinden, J., M. *FEBS letters* 123:287-290 (1981) (FIG. 6B). The purified cells were further expanded for an additional 30 days prior to characterization which demonstrated expression of the fibroblast markers vimentin and the absence of the neural precursor marker nestin (FIG. 6C).

iPSC-derived fibroblasts (at day 60 of differentiation) showed expression of lamin A and progerin at levels similar to those observed in the primary donor fibroblasts (FIG. 6D). iPSCs were differentiated to fibroblast-like cells in serum-containing medium for 30 days (FIG. 6A) and sorted by flow cytometry (FIG. 6B) for high levels of expression of the fibroblast markers CD13 and HLA-ABC (red box) as compared to iPSCs. iPSC-derived fibroblasts after sorting displayed fibroblast-like morphologies and expression of vimentin but no nestin (a neural marker) by immunocytochemistry. FIG. 6C. RT-PCR for lamin A and progerin transcripts showed upregulation in iPSC-derived fibroblasts (iPSC-fibroblasts) to similar levels observed in the donor fibroblasts. FIG. 6D. Modified-RNA was designed to express either nuclear-localized green fluorescent protein (nuclear-GFP) as a control or progerin fused to GFP (GFP-progerin). The addition of generic 5' and 3' UTRs as well as a Poly(A) tail and 5' cap structure facilitated the in vitro transcription reaction (Mandal et al., *Nat Protoc* 8:568-582 (2013); Warren et al., *Cell Stem Cell* 7:618-630 (2010)). FIG. 6E. Western blot analysis of transgene expression. n, nuclear-GFP; p, GFP-progerin. Analysis of detection using a lamin A/C antibody (N-18) revealed that progerin overexpression induces levels higher than the endogenous progerin level observed in HGPS iPSC-derived fibroblasts (arrows). FIG. 6F. Quantification of telomere length and the percentage of telomeres less than 2 kilobases (kb) by Q-FISH. n=4 replicate wells. FIG. 6G. Assessment of the senescence markers senescence-activated beta-galactosidase (SA-β-Gal) at all stages from the primary fibroblasts to iPSC-derived fibroblasts overexpressing progerin. n=2 replicate wells. FIG. 6H.

However, differentiation did not reestablish the age-associated marker profile in old donor iPSC-derived fibroblasts (FIG. 3A-C) as they now closely matched the profile of passage-matched young donor iPSC-derived fibroblasts. These data demonstrate that age-associated markers in primary fibroblasts from aged, apparently healthy donors are reset following reprogramming and are not reestablished upon differentiation into iPSC-derived fibroblasts.

Thus, age is lost after reprogramming, giving rise to exclusively young-like iPSC-derived fibroblasts that would potentially require years of in vitro culture to reestablish their age. In contrast, HGPS iPSC-derived fibroblasts did spontaneously reestablish the age-associated marker expression signature upon differentiation (FIGS. 3B and 3C) as reported in other iPSC-based models of HGPS (Liu et al., *Nature* 472:221-225 (2011); Zhang et al., *Cell Stem Cell* 8:31-45 (2011)), suggesting that with the right cues (i.e., progerin expression at high levels) can return an iPSC-derived fibroblast to an aged-like state.

Figure 3A:
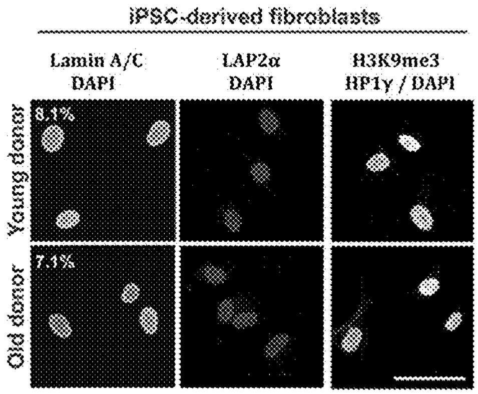
FIG. 3A-3C presents exemplary data showing that iPSC-derived fibroblasts from old donors do not regain age-associated markers following differentiation. (A) Immunocytochemistry for age-associated markers. Percentages indicate the proportion of cells with folded and/or blebbed nuclear morphologies. (B) Quantification of the markers shown in (A) indicates the high degree of overlap between iPSC-derived fibroblasts from young and old donors compared to HGPS iPSC-derived fibroblasts, which reestablish an age-like phenotype. (C) Analysis of DNA damage (left) and mitochondrial superoxide (right) further show that iPSC-derived fibroblasts from old donors have been reset to a “young”-like state. n.s. not significant, p<0.01, **p<0.0001 according to Kolmogorov-Smirnov tests (B) or Student's t tests (C). n=3 differentiations of independent iPSC clones performed at different times. Bar graphs represent mean±SEM. Scale bar: 50 μm.
Figure 3B:
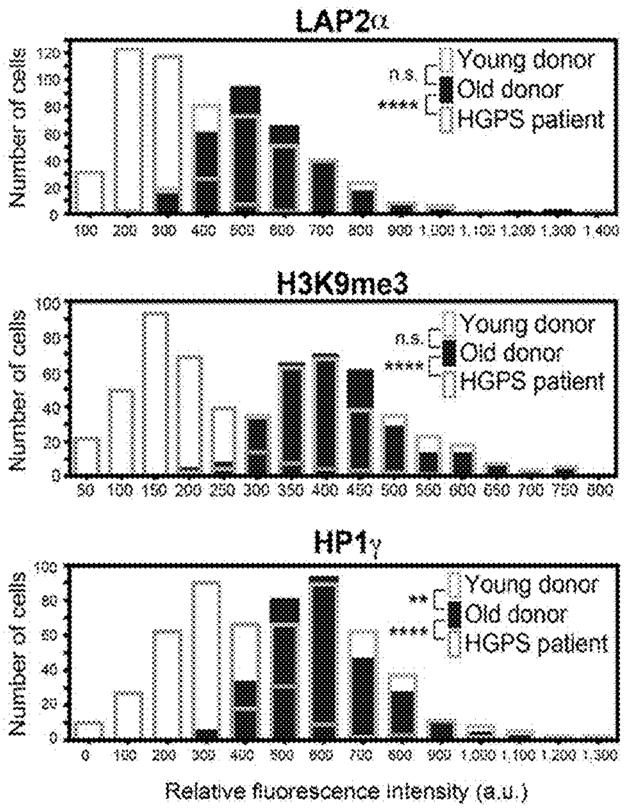
Figure 3C:
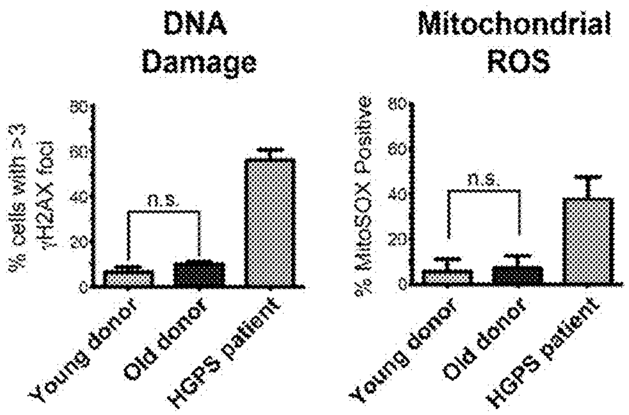

Immunocytochemistry for age-associated markers. Percentages indicate the proportion of cells with folded and/or blebbed nuclear morphologies. FIG. 3A. Quantification of the markers shown in (A) indicates the high degree of overlap between iPSC-derived fibroblasts from young and old donors compared to HGPS iPSC-derived fibroblasts, which reestablish an age-like phenotype. FIG. 3B. Analysis of DNA damage (left) and mitochondrial superoxide (right) further show that iPSC-derived fibroblasts from old donors have been reset to a "young"-like state. FIG. 3C.

Example 35

Acute Progerin Overexpression Reestablishes Age-Related Markers in iPSC-Derived Fibroblasts Further testing was performed to determine whether progerin overexpression is sufficient to induce age-associated markers in apparently healthy young and old donor iPSCderived fibroblasts which displayed an indistinguishable young-like phenotype after redifferentiation.

Figure 4A:
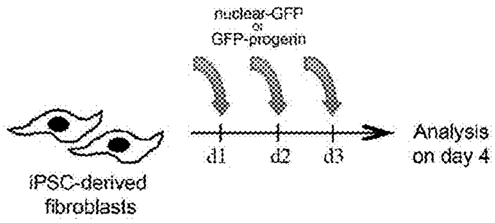
FIG. 4A-4D presents exemplary data showing that progerin overexpression induces age-associated changes in iPSC-derived fibroblasts from healthy donors regardless of donor age. (A) Modified-RNA was transfected into iPSC-derived fibroblasts on three consecutive days prior to analysis on day 4. (B) Overexpression of progerin (GFP-progerin) in iPSC-derived fibroblasts causes changes in nuclear morphology (as seen by GFP), expression of the lamina-associated protein (LAP2α), levels of DNA damage (γH2AX), and chromatin organization (H3K9me3; HP1γ), which were not observed with overexpression of a nuclear-localized GFP control (nuclear-GFP). Percentages indicate the proportion of cells with folded and/or blebbed nuclear morphologies. (C) Quantification of data shown in (B). Frequency distribution plots represent the fluorescence intensity of 100 cells from 3 independent RNA transfections of iPSC-derived fibroblasts derived from independent iPSC clones. (D) Flow cytometry analysis of the mitochondrial superoxide indicator MitoSOX suggests a dramatic increase in mitochondrial dysfunction with progerin overexpression. n=3 independent RNA transfections of iPSC-derived fibroblasts derived from independent iPSC clones. *p<0.05, p<0.01, **p<0.0001 according to Kolmogorov-Smirnov tests (LAP2α, H3K9me3, HP1γ) or Student's t-tests (γH2AX, MitoSOX). Bar graphs represent mean±SEM. Scale bar: 25 μm.
Figure 4C:
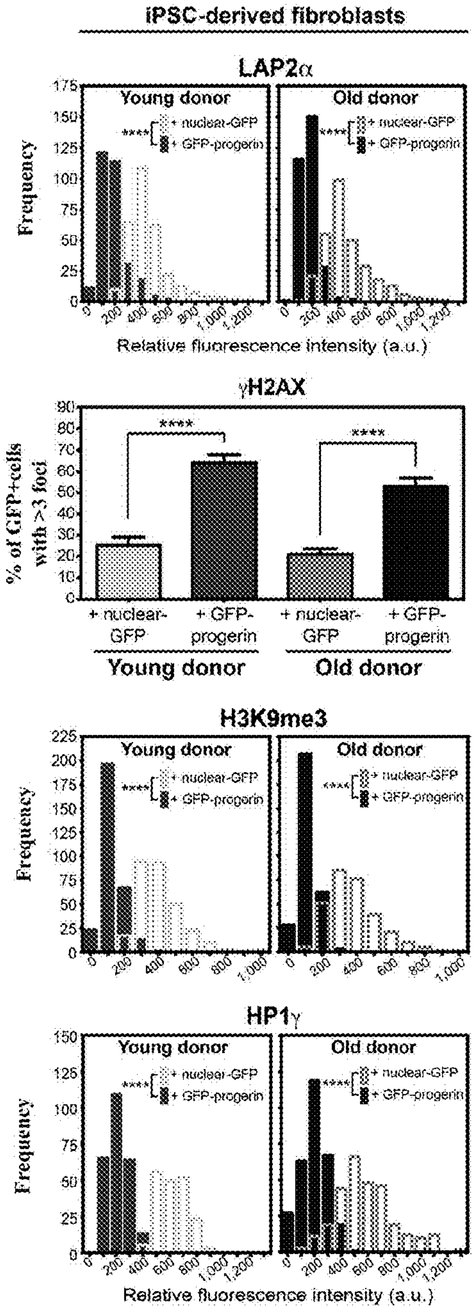
Figure 4B:
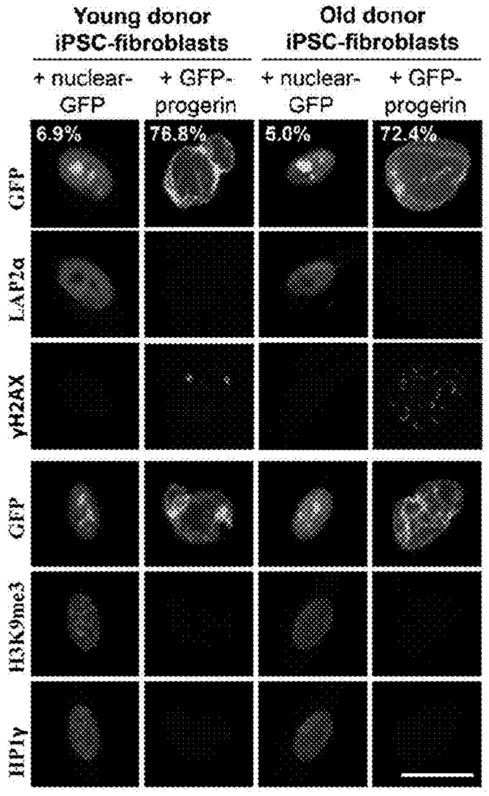
Figure 4D:
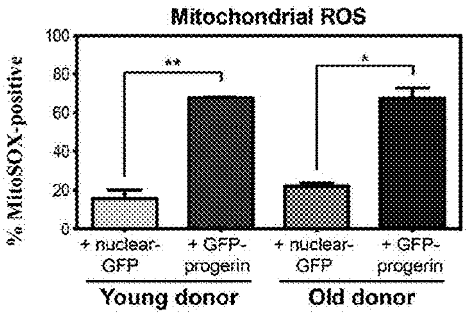

Synthetic mRNA (termed modified-RNA) (Kariko et al., 2005; Warren et al., *Cell Stem Cell* 7:618-630 (2010)) was used to overexpress either GFP fused to progerin (GFP-progerin) or a nuclear-localized GFP control (nuclear-GFP; FIG. 6E), allowing for easy manipulation of the amount and duration of expression. Daily transfection of modified-RNA for three days (FIG. 4A) induced progerin expression to levels similar or higher than what we observed in HGPS iPSC-derived fibroblasts (FIG. 6F, arrows). Strikingly, overexpression of GFP-progerin but not nuclear-GFP in apparently healthy young and old donor iPSC-derived fibroblasts induced nuclear morphology abnormalities, loss of LAP2α expression, formation of DNA double strand breaks (γH2AX), loss of heterochromatin markers (H3K9me3 and HP1γ) and increased mitochondrial dysfunction (FIG. 4B-4D). These progerin-induced features were indistinguishable from those observed in the primary fibroblasts from normally aged donors (FIG. 2A-2C and FIG. 5A).

Modified-RNA was transfected into iPSC-derived fibroblasts on three consecutive days prior to analysis on day 4. FIG. 4A. Overexpression of progerin (GFP-progerin) in iPSC-derived fibroblasts causes changes in nuclear morphology (as seen by GFP), expression of the lamina-associated protein (LAP2α), levels of DNA damage (γH2AX), and chromatin organization (H3K9me3; HP1γ), which were not observed with overexpression of a nuclear-localized GFP control (nuclear-GFP). Percentages indicate the proportion of cells with folded and/or blebbed nuclear morphologies. FIG. 4B. Quantification of data shown in (FIG. 4B). Frequency distribution plots represent the fluorescence intensity of 100 cells from 3 independent RNA transfections of iPSC-derived fibroblasts derived from independent iPSC clones. FIG. 4C. Flow cytometry analysis of the mitochondrial superoxide indicator MitoSOX suggests a dramatic increase in mitochondrial dysfunction with progerin overexpression.

Normal aging of mitotic cells is typically associated with the shortening of telomeres to a critical point when the cell undergoes senescence, reaching Hayflick's limit (Hayflick, *Exp Cell Res* 37:614-636 (1965). Telomere lengths were measured using quantitative fluorescence in situ hybridization (Canela et al., *Proc Natl Acad Sci USA* 104:5300-5305 (2007)) in transfected iPSC-derived fibroblasts to determine whether progerin can induce telomere shortening. Following progerin overexpression, iPSC-derived fibroblasts demonstrated a decrease in overall length and an increase in the percentage of short telomeres with progerin overexpression (FIG. 6G). This result was further corroborated by an increase in senescence-activated β galactosidase (SA-β-Gal) staining (FIG. 6H). Progerin-induced changes in iPSC-derived fibroblasts were independent of donor age, demonstrating no difference in phenotype whether the cells were derived from a young or an old donor.

These data indicate that progerin overexpression is sufficient to rapidly induce phenotypes in iPSC-derived fibroblasts that phenocopy some aspects of normal aging.

Example 36

Progerin Induces Neuronal Aging Phenotypes in iPSC-Derived mDA Neurons

Figure 8A:
FIG. 8A-8F presents exemplary data showing differentiation of iPSCs to mDA neurons. The protocol for the derivation of mDA neurons from iPSCs is presented with immunocytochemical characterization of the resulting cells at various stages of the differentiation process. (A) Schematic illustration of the differentiation protocol for the derivation of mDA neurons from iPSCs. Mit. C, mitomycin C. (B) Immunocytochemistry at day 13 of differentiation for FOXA2 (red), LMX1A (green) and OCT4 (pink). (C) Mitomycin C treatment 1 day following the final day 30 replating helped to eliminate the remaining proliferating cells (post-mitotic neurons unaffected). (D and E) Immunocytochemistry (D) and quantification (E) demonstrate that almost 100% of the remaining cells at day 70 of differentiation were post-mitotic neurons (TUJ1+/Ki67−) and that greater than 80% of those neurons expressed mDA-specific markers (FOXA2+/TH+). As previously reported (Kriks et al., *Nature* 480:547-551 (2011)) approximately 40% of the TH+ neurons also express the more mature mDA marker NURR1. n=at least 3 independent differentiations of independent iPSC clones. (F) Immunocytochemistry for lamin A and lamin B2 during the mDA neuron differentiation shows endogenous upregulation of the lamin A isoform with similar timing to the onset of nuclear folding. Bar graph represents mean±SEM. Scale bars: 50 μm.
Figure 8B:
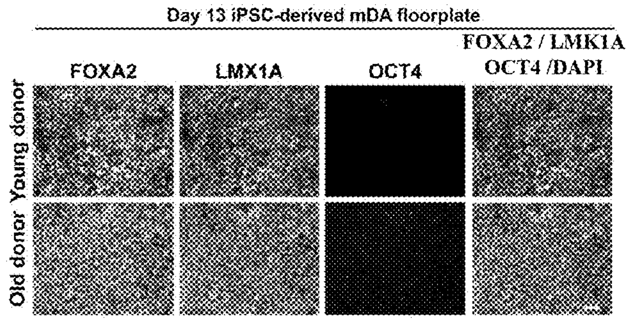

In order to further validate an induced aging strategy, other cell types were tested. For example, progerin overexpression was tested to induce age-like phenotypes in a post-mitotic cell. Young and old donor iPSCs were differentiated into midbrain dopamine (mDA) neurons, a cell type primarily affected in PD, using a previously established protocol (Kriks et al., *Nature* 480:547-551 (2011)) (FIG. 8A). Within 13 days, differentiated iPSCs had converted into LMX1A/FOXA2-double positive midbrain floorplate precursors, an early stage of mDA neuron development (FIG. 8B).

Figure 8C:
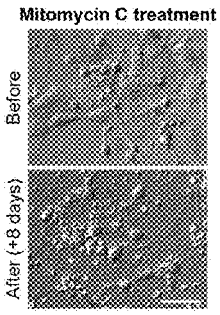
Figure 8D:
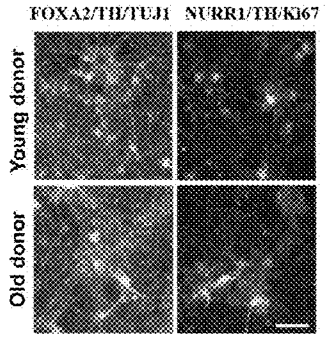
Figure 8E:
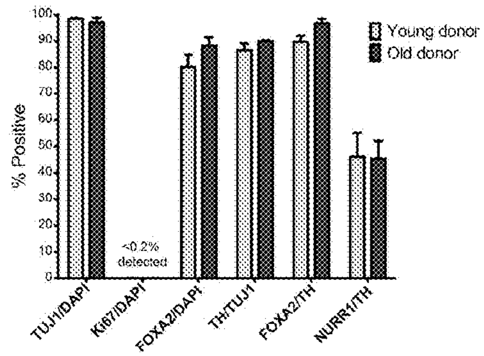

Immature mDA neurons at day 32 of differentiation were transiently treated with mitomycin C to eliminate any contaminating proliferating cells (FIG. 8C). iPSC-derived mDA neurons that were further matured for an additional six weeks continued to express mDA markers such as FOXA2 and tyrosine-hydroxylase (TH) at day 70 in iPSC clones independent of donor age (FIGS. 8D and 8E). Interestingly, iPSC-derived mDA neurons had a mildly folded nuclear morphology that occurred concomitant with the onset of endogenous lamin A expression (FIG. 8F), though it is unclear whether this reflects an age-like phenotype or simply a tissue- and cell-type specific behavior.

Figure 8F:
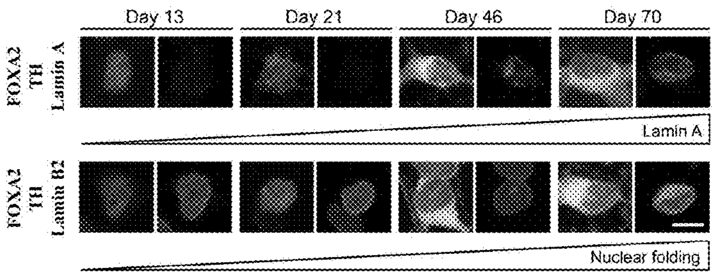

Schematic illustration of the differentiation protocol for the derivation of mDA neurons from iPSCs. Mit. C, mitomycin C. FIG. 8A. Immunocytochemistry at day 13 of differentiation for FOXA2 (red), LMX1A (green) and OCT4 (pink). FIG. 8B. Mitomycin C treatment 1 day following the final day 30 replating helped to eliminate the remaining proliferating cells (post-mitotic neurons unaffected). FIG. 8C. Immunocytochemistry (FIG. 80) and quantification (FIG. 8E) demonstrate that almost 100% of the remaining cells at day 70 of differentiation were post-mitotic neurons (TUJ1+/Ki67−) and that greater than 80% of those neurons expressed mDA-specific markers (FOXA2+/TH+). As previously reported (Kriks et al., *Nature* 480:547-551 (2011)) approximately 40% of the TH+ neurons also express the more mature mDA marker NURR1. n=at least 3 independent differentiations of independent iPSC clones. Immunocytochemistry for lamin A and lamin B2 during the mDA neuron differentiation shows endogenous upregulation of the lamin A isoform with similar timing to the onset of nuclear folding. FIG. 8F.

This modeling paradigm was also applied to age-related marker signatures of late-onset neurodegenerative disorders by using iPSC-derived neurons (FIGS. 7 and 8). Interestingly, HGPS patients do not show obvious signs of neurodegeneration during their relatively short life span (median age at death is 11-13 years of age) (Hennekam *Am J Med Genet A* 140:2603-2624 (2006)). Although it is not necessary to understand the mechanism of an disclosure it is believed that there may not be sufficient time for progerin to accumulate in these patients due to a negative regulation of lamin A and progerin by a central nervous system-specific expression of miR-9 (Nissan et al., *Cell Rep* 2:1-9 (2012); Jung et al., *Proc Natl Acad Sci USA* 109:E423-431 (2012)). In fact, the present data show that upregulation of lamin A and progerin in the human brain occurs late in life (>70 years of age). (FIG. 11).

An acute 3-day overexpression of progerin modified-RNA in iPSC-derived mDA neurons resulted in a reduced accumulation of progerin protein compared to iPSC-derived fibroblasts and no obvious phenotype. In contrast, extending progerin exposure to 5 days in mDA neurons (FIG. 7A), induced protein levels that exceeded the levels of endogenous A-type lamin expression (FIG. 7B, arrows). Of note, higher basal levels of DNA damage and mitochondrial ROS were already observed without progerin expression in iPSC-derived mDA neurons by day 70 of differentiation regardless of donor age (FIGS. 7C and 7D). Following progerin overexpression GFP-positive cells showed evidence of enhanced nuclear folding and blebbing, increased accumulation of DNA damage (FIG. 7C) and signs of mitochondrial dysfunction (FIG. 7D) as measured by the accumulation of γH2AX foci and mitochondrial superoxide, respectively.

However, in contrast to iPSC-derived fibroblasts (FIG. 4), significant changes in LAP2α, H3K9me3 or HP1γ were not observed in the neurons (FIG. 7E). Positive SA-β-Gal staining, a marker of senescence, was not detected in iPSC-derived mDA neurons under any of the treatment condition. These data demonstrate both shared and cell type-specific responses of iPSC-derived fibroblasts and mDA neurons to our in vitro aging paradigm.

Modified-RNA was transfected into iPSC-derived mDA neurons on five consecutive days prior to analysis on day 6. FIG. 7A. Western blot analysis of transgene expression. A GFP band at 100 kDA denotes the GFP-progerin fusion protein while a GFP band at 27 kDA represents the nuclear-GFP transgene. Lamin A isoforms including the transgene were recognized by a single antibody. Note that progerin overexpression levels exceed endogenous lamin A levels (arrows). iPSC-derived mDA neurons do not appear to express detectable levels of progerin protein endogenously. n, nuclear-GFP; p, GFP-progerin. FIG. 7B. Progerin overexpression enhances nuclear folding and blebbing (as seen by lamin B2, pink) and increases DNA damage accumulation (γH2AX) in both young and old donor-derived iPSC-mDA neurons.

Percentages indicate the proportion of cells with enhanced nuclear folding and/or blebbing or the proportion of cells with >3 enlarged γH2AX foci. FIG. 7C. Flow cytometry analysis of mitochondrial superoxide levels (MitoSOX) demonstrates increased mitochondrial dysfunction with progerin overexpression. n=3 independent RNA transfections of iPSC-derived mDA neurons derived from independent iPSC clones. FIG. 7D. Quantification of immunocytochemistry for LAP2α, H3K9me3 and HP1γ shows no difference between iPSC-mDA neurons transfected with GFP-progerin or nuclear-GFP, unlike the phenotype observed in iPSC-derived fibroblasts. Fluorescence intensities were normalized to the intensities observed in nuclear-GFP-treated cells. FIG. 7E.

The data presented herein shows that the efficiency of neural and neuronal differentiation towards FOXA2+/TH+ midbrain dopamine neuron cultures is unaffected by donor fibroblast age or HGPS status. Nonetheless, forced expression of progerin in iPSC-derived midbrain dopamine neuron cultures using a synthetic mRNA technology triggers changes in nuclear lamina comparable to those observed in iPSC-derived fibroblast. The data also show a progerin-mediated induction of DNA damage and mitochondrial stress without affecting Nurr1+ midbrain dopamine neuron identity (FIGS. 7 and 8).

To further examine cell-type specific responses to progerin exposure, parameters associated with in vivo neuronal aging such as degenerative changes in dendrite branching (Hof et al., *Trends Neurosci* 27: 607-613 (2004) were investigated. Remarkably, 5 days of progerin exposure in differentiated (day 65) mDA neurons was sufficient to induce a degenerative phenotype resulting in the breakdown of established neurites which was visualized by TUJ1 staining (FIG. 12A). No degeneration was observed in cells transfected with control nuclear GFP mRNA.

Expression of MAP2, which specifically labels dendrites, was also assessed (Bernhardt et al., *J. Comp. Neurol* 226: 203-221 (1984)). Quantitative analysis showed a marked reduction in average dendrite length following progerin exposure in mDA neurons from both young and old donor iPSCs (FIG. 12B). The percentages of iPSC-derived neurons expressing the mDA neuron markers NURR1 and TH remained unchanged, suggesting that the addition of progerin was not simply inducing mDA neuron toxicity (FIGS. 13A and 13B), in contrast to the treatment of mDA neurons with mitochondrial toxins such as CCCP that rapidly induces mDA neuron marker loss.

To further characterize the age-like phenotype in iPSC-derived mDA neurons following overexpression of progerin, a gene expression analysis by RNA-seq was performed (raw data: GEO (ncbi.nlm.nih.gov/geo/); Accession No.: GSE52431). Principle component analysis confirmed a reset in gene expression following reprogramming and illustrated the similarity between iPSC-derived mDA neurons from donors of different ages (FIG. 12C). Furthermore, progerin overexpression induced highly similar (p<2.93x10-321) changes in young and old donor iPSC-derived mDA neurons (FIG. 12C and FIG. 13C). Many of the overlapping progerin-induced changes in gene expression (FIG. 13C) have been previously reported to play a role in processes associated with neuronal aging, such as axon degeneration/regeneration (TMSB10, TMSB4X, CCDC126, TSNAX, NOSTRIN, LAMC3), protein misfolding and aggregation (NEDD8, PSMB3, PPIB, UBC), oxidative stress (ENHO, NDUFB6, ATP5L, PRDX4, FTL, ATOX1, TNIP3), DNA damage (NOP10, TCEAL7), cell cycle induction (PCNA, MIR663A) and chromatin modification (PRDM1) (FIG. 12D).

Figure 13D:
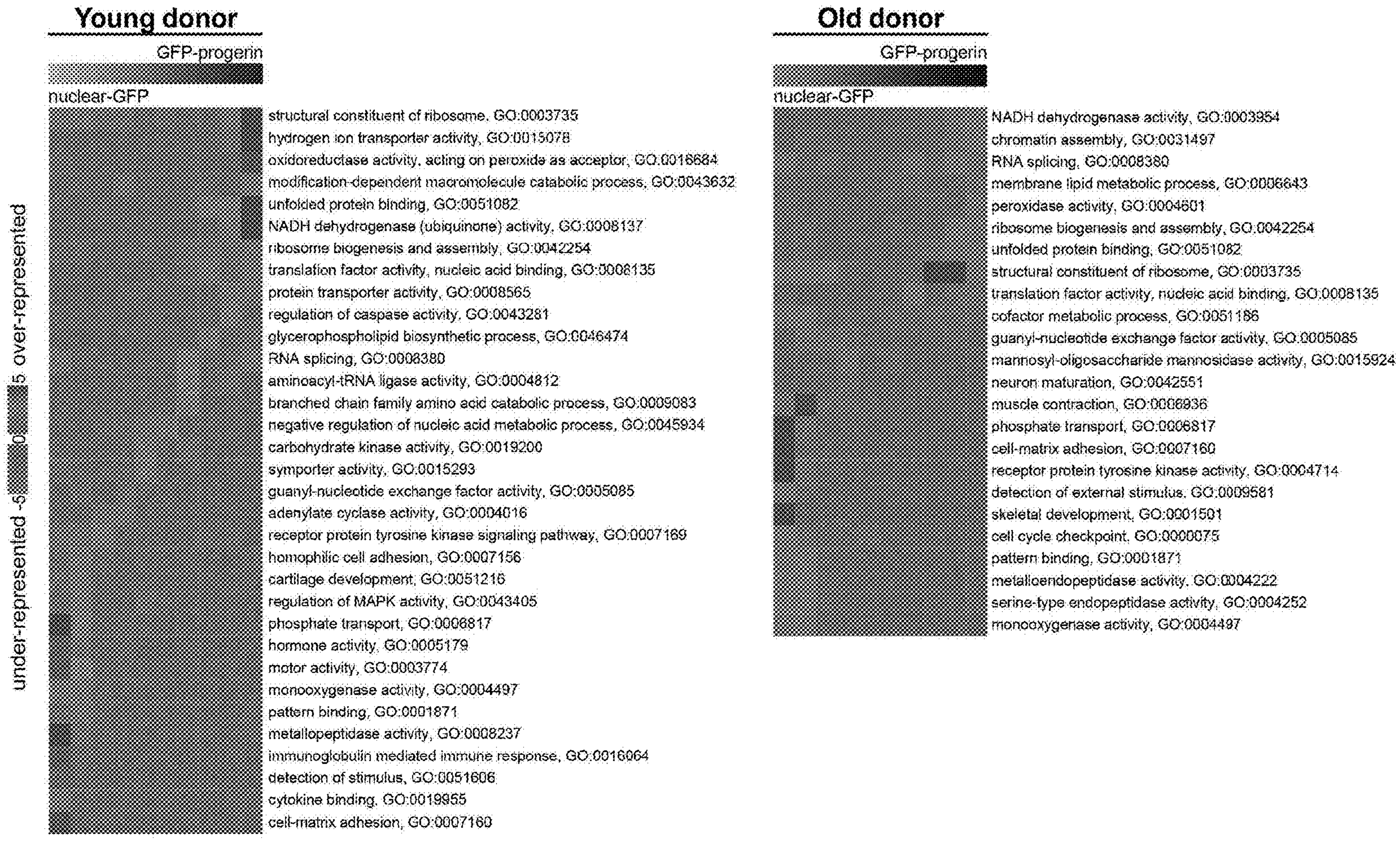

Induction of transcripts associated with age-like processes was confirmed by analysis of gene ontology (FIG. 13D). Among differentially expressed transcripts, several uncharacterized genes and non-coding RNAs (FIG. 12E) were found that were reminiscent of recent observations made in the aging rat brain (Wood et al., *Age* (*Dordr*) 35: 763-776 (2013)).

Immunocytochemistry for the pan-neuronal marker TUJ1 shows a loss of the established neuronal network in day 70 iPSC-derived mDA neurons overexpressing progerin but not iPSCderived neurons overexpressing nuclear-GFP. FIG. 12A. MAP2 immunocytochemistry reveals reduced intact dendrite lengths following overexpression of progerin in most, but not all (inset), iPSC-mDA neurons derived from both young and old donors. Frequency distributions display total dendrite length measurements from 3 independent RNA transfections (50 cells each, non-apoptotic nuclei). FIG. 12B. Principal component analysis of RNA-seq gene expression data further corroborates the reprogramming-induced reset of age that results in the high similarity of iPSC-derived mDA neurons from both young and old donors. Progerin overexpression induces similar changes in mDA neurons independent of donor age. The top 20 upregulated (left) and downregulated (right) genes in progerin-treated compared to control nuclear-GFP-treated young donor (green) and old donor (blue) iPSC-mDA neurons. Genes are ranked according to iPSC-mDA neurons derived from the old donor. Red denotes uncharacterized genes and orange denotes non-coding RNAs. Dotted line indicates the threshold for significance. FIG. 12D. Pie charts representing the proportion of the significantly differentially expressed transcripts that are coding, non-coding, or uncharacterized. FIG. 12E.

The percentage of NURR1+ iPSC-derived mDA neurons (FIG. 13A) and the protein expression levels of TH (FIG. 13B) remained unchanged with transfection, indicating that progerin overexpression does not downregulate mDA neuron proteins (a typical sign of acute toxicity). Venn diagram where each colored circle indicates the number of differentially expressed genes (Fold change +/−2, p<0.05) between two groups. The black circle indicates the overlapping "aging signature" that was further analyzed. FIG. 13C. The significant gene ontology terms that are enriched in nuclear-GFP-treated or GFP progerin-treated iPSC-derived mDA neurons (left to right). FIG. 13D. Of note, progerin induced the upregulation of ZNHT3, a coactivator of a recently described PD biomarker (Potashkin et al., *PloS one* 7, e43595 (2012)), and downregulation of BCAS1, a gene found to be lowly expressed in postmortem tissue from PD patients (Kim et al., *DNA Research* 13:275-286 (2007)). Finally, progerin overexpression caused the downregulation of SIRT4, a mitochondrial sirtuin with reported roles in regulating metabolism and promoting longevity (Shih et al., *Genes Cancer* 4:91-96, (2013)).

Example 37

Progerin-Induced Aging Enables the Modeling of Late-Onset PD Features In Vitro and In Vivo This Example discloses a model of late-onset neurodegenerative disorders such as Parkinson's disease (PD) using age-appropriate cells.

Recently, several studies have reported iPSC-based disease models of PD; however, these studies have described phenotypes that arise in cell types of uncertain relevance to the disease such as neural stem cells (Liu et al., *Nature* 491:603-607 (2012)) or represent early biochemical phenotypes prior to any signs of the severe neurodegeneration observed in the human disease (Cooper et al., *Sci Transl Med* 4:141ra190 (2012); Nguyen et al., *Cell Stem Cell* 8:267-280 (2011); Seibler et al., *J Neurosci* 31:5970-5976 (2011)). The present data suggest otherwise in that the absence of a neurodegenerative phenotype in various in vitro disease models of late-onset disease may be a result of the age-reset during reprogramming.

Similar to PD patients who do not exhibit disease symptoms until later in life, PD iPSC-derived mDA neurons may be too "young" to mimic the degenerative phase of the disease. Although it is not necessary to understand the mechanism of an disclosure, it is believed that progerin overexpression could reveal disease-associated phenotypes that cannot currently be modeled due to the "young" status of PD iPSC-derived mDA neurons.

Consequently, mDA neurons were generated by differentiating PD-iPSCs with homozygous mutations (FIG. 15A) in PINK1 (Q456X) or Parkin (V324fsX434). PINK1 and Parkin. These PD mutations are thought to act in a common pathway to promote the selective autophagic degradation of damaged mitochondria (reviewed in (Dodson et al., *Curr Opin Neurobiol* 17:331-337 (2007)) in addition to the unique functions of Parkin in the ubiquitin proteasome pathway (Shimura et al., *Nat Genet* 25:302-305 (2000). While some disease-associated phenotypes were previously reported in PINK1 mutant iPSC-derived neurons (Seibler et al., *J Neurosci* 31:5970-5976 (2011), they required treatment with a mitochondrial toxin and did not trigger neuronal degeneration.

The PINK1 and LRRK2 PD-iPSC lines were selected for several reasons: i) availability of integration-free iPSCs and independent efforts that may yield the matched iso-genic pairs of clones following TALEN based gene editing; ii) the choice of two mutations each of which is thought to have a distinct disease phenotype for triggering PD (mitochondrial versus aggregation hypothesis), iii) the relevance of LRRK2 (most common human mutation in PD) for understanding sporadic PD and iv) preliminary evidence for a disease related ultrastructural phenotype in PINK1 line (abnormal mitochondria) in agreement with the literature on the role of Parkin and PINK1 in PD pathogenesis (10). LRRK2 mutant cells may supplement the data by demonstrating shared PD pathogenesis phenotypes in the context of different mutations. Although it is not necessary to understand the mechanism of an disclosure, it is believed that PD iPSC-derived mDA neurons exposed to in vitro aging exhibits a set of shared and distinct phenotypes with mDA neurons derived from control iPSCs.

Figure 14A:
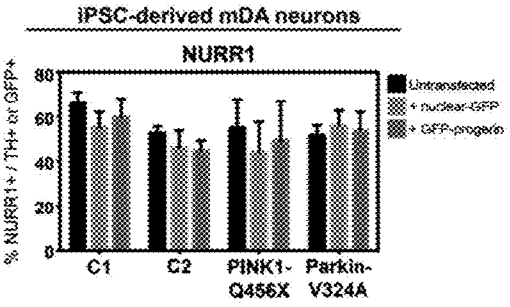
Figure 14B:
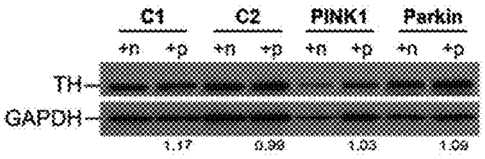
Figure 15A:
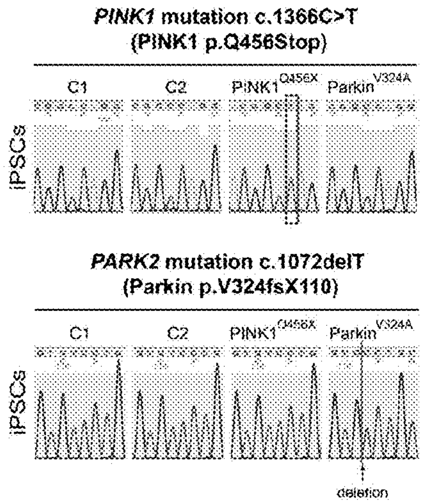
Figure 15B:
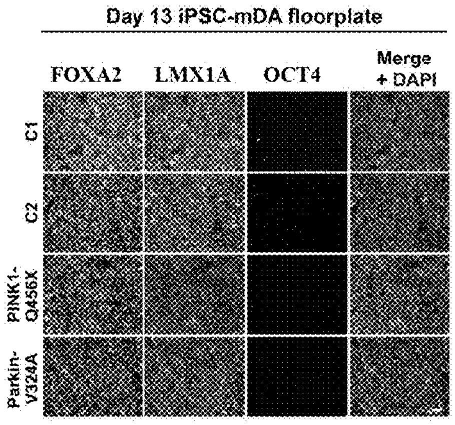
Figure 15C:
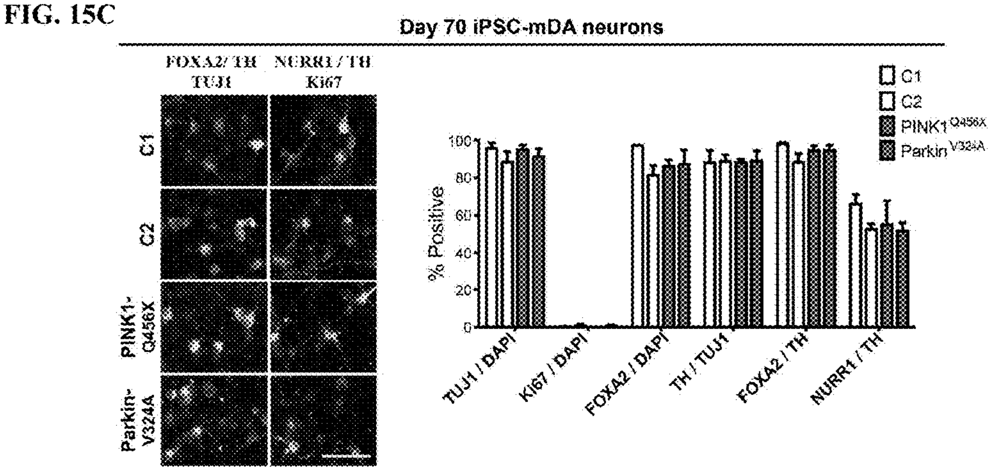

The data show that PD-iPSCs differentiated towards mDA neurons with similar efficiencies to iPSCs derived from apparently healthy donors (C1 and C2; FIGS. 15B and 15C). At day 65 of differentiation PD− and control-iPSC-derived mDA neurons were each transfected with GFP-progerin or nuclear-GFP for 5 days. mDA neuron markers such as NURR1 (FIG. 14A) and TH (FIG. 14B), which were comparable between PD− and control-iPSC-derived mDA neurons, were unchanged following short-term GFP-progerin exposure.

Figure 14C:
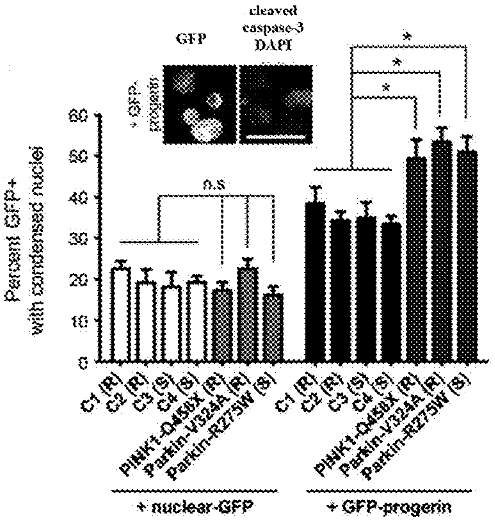
Figure 14D:
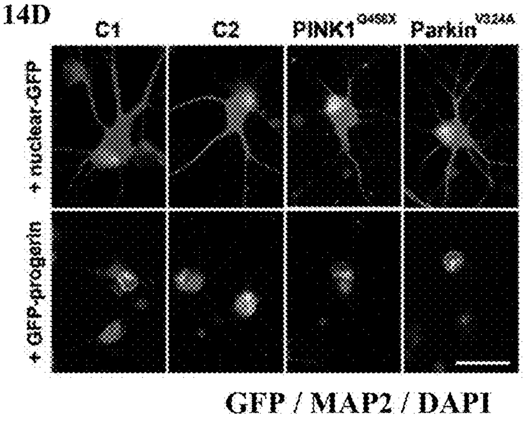
Figure 14E:
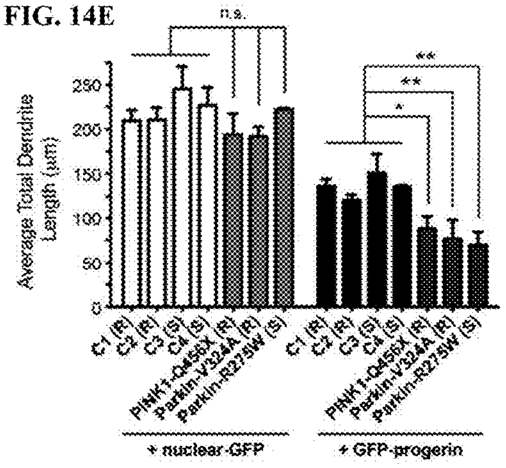
Figure 15D:
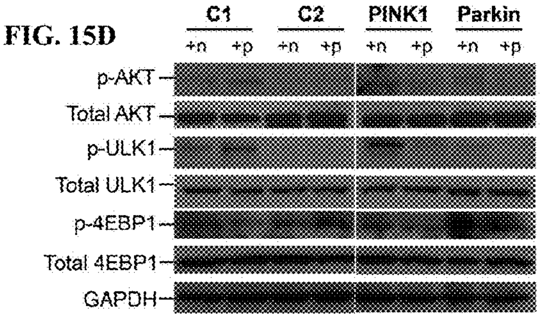
Figure 15E:
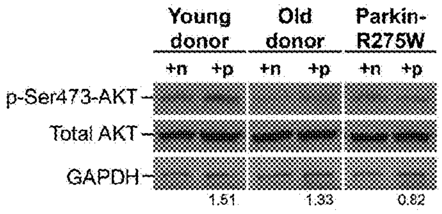

Sequencing for the homozygous PINK1 c.1366C>T and PARK2 c.1072delT mutations found in the PD mutant iPSCs but not in apparently healthy control iPSCs. FIG. 15A. Immunocytochemistry at day 13 of differentiation demonstrated no differences between healthy donors and PD patients in the conversion of OCT4+ iPSCs to FOXA2+/LMX1A+ mDA floorplate precursors. FIG. 15B. Further differentiation of precursors to post-mitotic mDA neurons was unaffected in PD mutant cells. n=at least 3 independent differentiations. FIG. 15C. Western blot analysis of AKT pathway signaling in an additional PD patient with a heterozygous mutation in Parkin (p.R275W). Numbers below the blots indicate the ratio of p-AKT (GFP-progerin) to p-AKT (nuclear-GFP). n, nuclear-GFP; p, GFP-progerin. FIG. 15D Of particular interest is in defining PD-related phenotypes that depend on induced in vitro aging and thereby mimic the late-onset nature of the disease. For instance, an initiation of cell death was observed with a significant increase in the appearance of condensed nuclei that expressed cleaved caspase-3 in PD− versus control-iPSC-derived mDA neurons (FIG. 14C), indicating that PD mutant mDA neurons are more prone to activating a cell death program upon induced aging. GFP-progerin-positive condensed nuclei were not detected until day 4 or day 5 of progerin transfection, suggesting a progressive decline rather than an acute toxicity. Furthermore, while dendrite lengths in surviving TH/MAP2-positive mDA neurons were not significantly different in PD− versus control-iPSC-derived mDA neurons, progerin overexpression accelerated dendrite degeneration in PINK1 and Parkin mutant mDA neurons as compared to mDA neurons derived from healthy donors (FIGS. 14D and 14E).

Figure 14F:
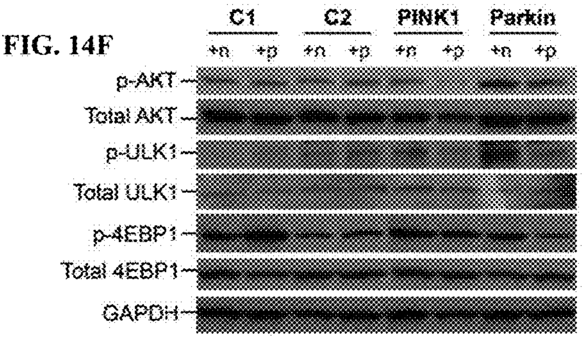
Figure 14G:
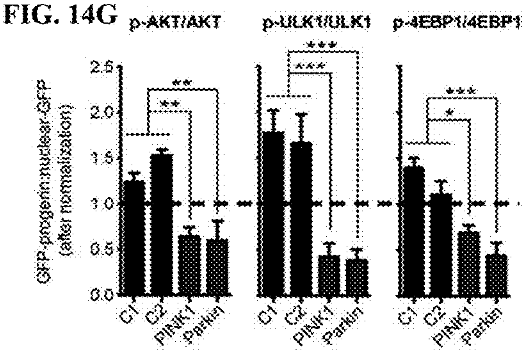

It has been suggested that decreased neuronal survival in PD is at least in part caused by diminished levels of phosphorylated S473 AKT (p-AKT), which have been observed in PD models (Malagelada et al., *In Journal of Neuroscience,* 14363-14371 (2008); Ries et al., *In Proc Natl Acad Sci USA,* 18757-18762 (2006); Tain et al., *In Nat Neurosci,* 1129-1135 (2009) as well as in brain tissue from sporadic PD patients (Timmons et al., *In Neurosci Lett,* 30-35 (2009). Interestingly, PINK1-Q456X and Parkin-V324A mutant iPSC-derived mDA neurons showed a significant reduction in p-AKT in response to progerin while C1 and C2 iPSC-derived mDA neurons showed a slight increase in p-AKT following progerin exposure (FIGS. 14F and 14G). The deregulation of AKT signaling also resulted in the corresponding changes in the phosphorylation of the downstream signaling targets ULK1 and 4EBP1 (FIGS. 14F and 14G). There was considerable variability in the basal levels of AKT, ULK1 and 4EBP1 across replicate differentiations independent of genotype and treatment (FIG. 14F, FIG. 15D). However, the progerin-induced reduction in the activation status of each of the AKT signaling components in PD− versus control-iPSC derived mDA neurons was consistent (independent of basal levels) and mimicked the reported signaling changes in the brain of PD patients and in animal models of PD.

To further confirm the progerin-induced differences between PD− and control-iPSC derived mDA neurons, additional fibroblasts were reprogrammed from a PD patient with a heterozygous R275W Parkin mutation using Sendai virus based reprogramming. Similar to the progerin-induced phenotype in PINK1-Q456X and Parkin-V324A, progerin overexpression drove increased apoptosis (FIG. 14C), enhanced dendrite shortening (FIG. 14E) and reduced AKT activation (FIG. 15E) in Parkin-R275W iPSC-derived mDA neurons compared to cells derived from apparently healthy young and old donors (C3 and C4).

Quantification of NURR1+ cells (A) and western blot analysis of TH protein levels (B) do not reveal significant differences with transfection of GFP-progerin modified-RNA. n, nuclear-GFP; p, GFP-progerin. Numbers below the western blot indicate the ratio of GFPprogerin:nuclear-GFP expression of TH normalized to GAPDH. FIGS. 14A and 14B. Analysis of GFP+ cells undergoing cell death following RNA transfection which were identified by their condensed nuclear morphologies. Images display a representative example of cleaved caspase-3 immunocytochemistry in cells treated with progerin. FIG. 14C. Immunocytochemistry for the dendrite marker MAP2. FIG. 15 D. Quantification of total dendrite lengths per GFP+ neuron shows accelerated dendrite shortening in PD mutant iPSC-derived mDA neurons compared to apparently healthy controls (C1-C4) in response to progerin overexpression. FIG. 15D. Western blot analysis of AKT pathway signaling (FIG. 15F) demonstrates genotype-specific responses to progerin overexpression. Quantification of phospho-specific bands (FIG. 15G) was normalized to total protein before taking the ratio of the levels expressed with progerin treatment to nuclear-GFP treatment. Dotted line indicates an equal amount of phospho protein in both treatment conditions.

Figure 16A:
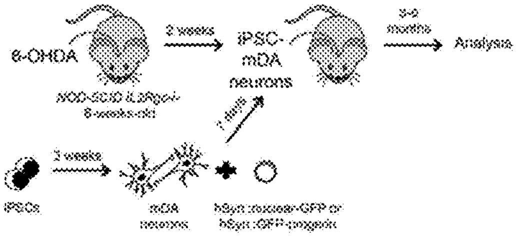

In order to assess the long-term effects of progerin exposure, mDA neurons derived from PD− and control-iPSCs were transduced with lentiviral vectors expressing GFP-progerin or nuclear-GFP under the control of the neuron-specific human synapsin (hSyn) promoter and grafted into the striatum of 6-hydroxydopamine lesioned NOD-SCID IL2Rgc-null mice (FIG. 16A).

Figure 16B:
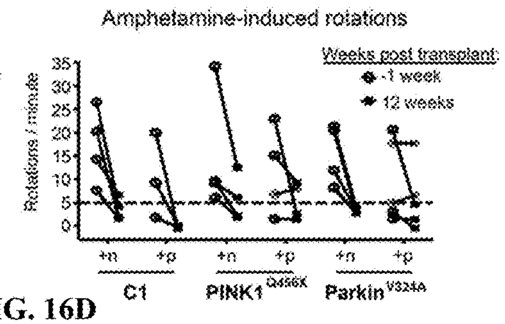
Figure 17A:
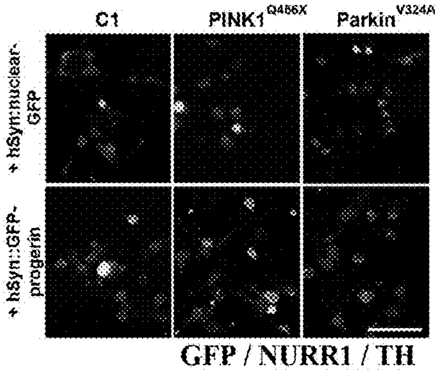

In vitro analysis of matched aliquots of cells 24-hours after transplantation confirmed expression of NURR1 and TH in GFP-positive cells (FIG. 17A). Onset of hSyn-driven transgene expression was at one day prior to grafting and expression was maintained in cultured cells for at least 90 days (latest time point tested). In vivo analysis three months after grafting resulted in a reduction of amphetamine-induced rotation scores in most animals (FIG. 16B), indicating mDA neuron survival above the threshold required for behavioral improvement.

Figure 16C:
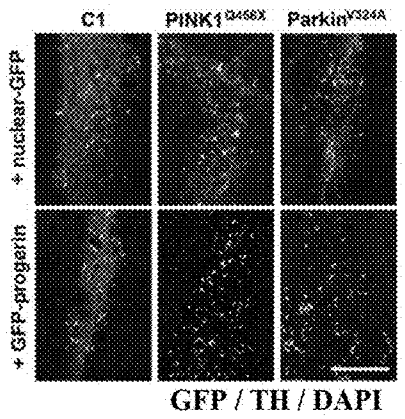
Figure 16D:
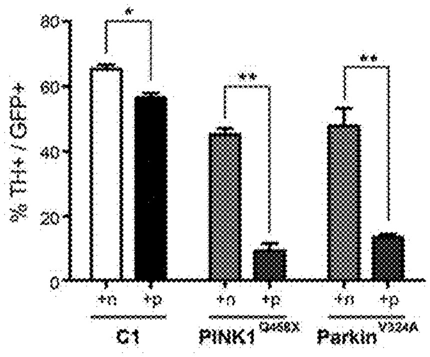

Interestingly, however, a subset of animals did not recover (FIG. 16B, pink symbols) that had received either PINK1− or Parkin-derived neurons expressing progerin, which was surprising considering that survival of few mDA neurons is required to rescue behavior under those conditions. To address whether incomplete behavioral recovery in the animals was due to a smaller number of surviving mDA neurons, we performed stereological quantification of the grafts. While graft volume was not significantly affected in progerin-treated versus control groups, progerin-expressing mDA neuron grafts showed a dramatic reduction in TH+ cell numbers (FIGS. 16C and 16D). Strikingly, the deficiency of TH+ cells was particularly pronounced in progerin-expressing mDA neuron grafts from PINK1-Q456X and Parkin-V324A iPSCs and minimal in control-iPSC-mDA neuron grafts. Those results mimic the accelerated loss of TH observed in PD patients, though the mechanism of TH+ cell loss remains to be determined.

Figure 17B:
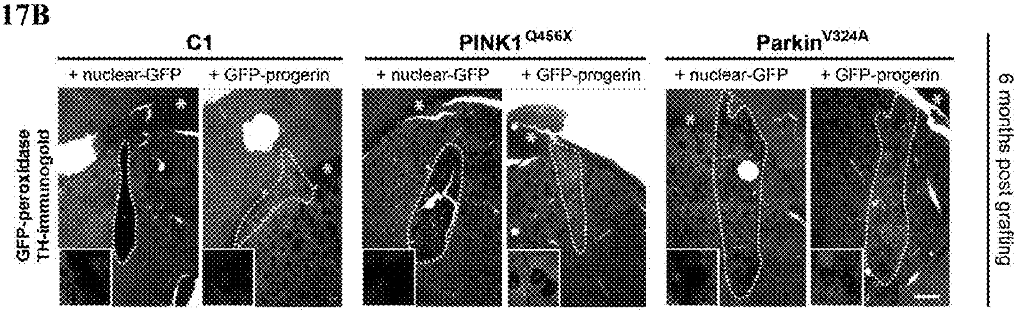
Figure 17C:
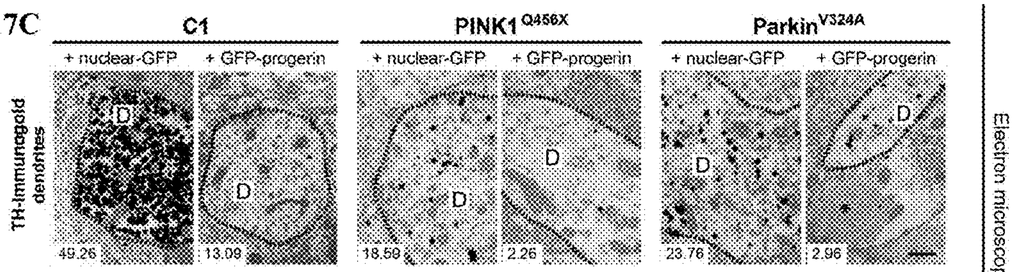
Figure 17D:
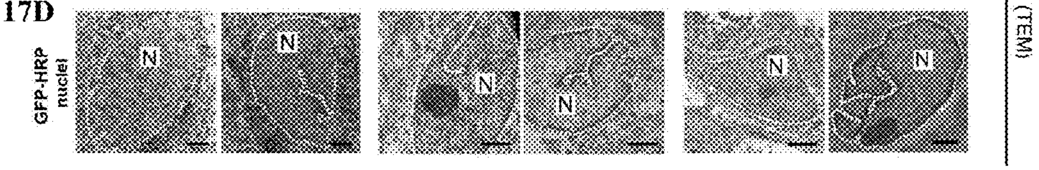

In order to further assess biomarkers of age and disease status of the iPSC-derived mDA neurons, an ultrastructural analysis of the human grafts six months after transplantation was performed by transmission electron microscopy (TEM). Initial observations of the embedded mouse brains by light microscopy demonstrated the continued, progressive loss of TH immunoreactivity in grafts overexpressing progerin (FIG. 17B). Analysis by TEM confirmed the progerin-induced reduction of TH expression in iPSC-derived mDA neuron dendrites and folded nuclear morphologies (FIGS. 17C and 17D).

To determine the age status of the grafted neurons we focused on the intracellular accumulation of neuromelanin. Neuromelanin is dark colored pigment present in adult mDA neurons but absent in fetal or neonatal stages including iPSC-derived mDA neurons (Mann et al., *Brain* 97: 489-498 (1974); Sulzer et al., *J Neurochem* 106: 24-36 (2008). In human fetal tissue transplantation studies neuromelanin was detected in grafts 4-14 years after intrastriatal injection, a time course similar to normal development (Chu et al., *STEM CELLS* 24:177-185 (2010)). In just six months, a robust accumulation of neuromelanin was observed with lipofuscin deposits selectively in grafts overexpressing progerin (an average of eight deposits per 55 $\mu m^2$ versus 0.5 in control nuclear-GFP expressing grafts, FIG. 16E), indicating that progerin dramatically accelerates mDA neuron aging regardless of genetic background.

Figure 16E:
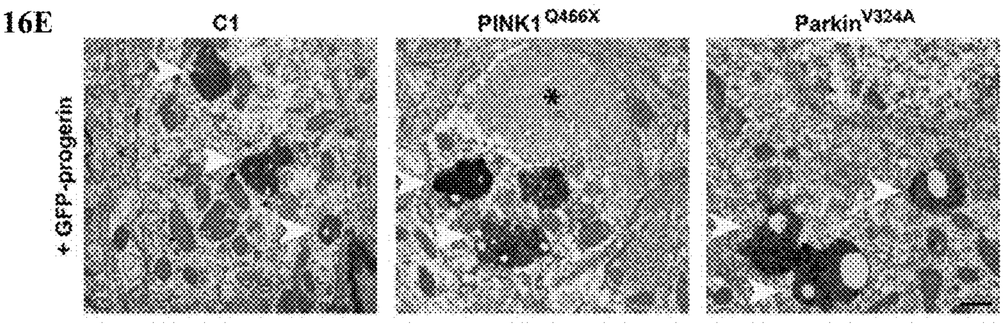
Figure 16F:
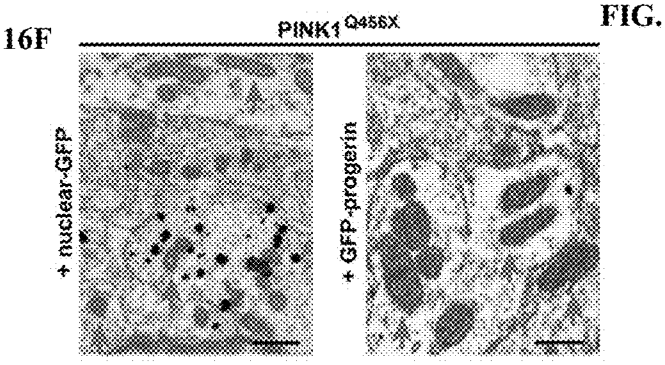

In addition, progerin overexpression revealed genotype-specific effects in PD-iPSC derived grafts, phenotypes not observed in PD grafts overexpressing nuclear-GFP or in any non-PD control grafts. For instance, signs of neurite degeneration such as the appearance of fibrillar bodies were prominent in PD-derived grafts overexpressing progerin (asterisks in FIGS. 16E and 16G and FIG. 17C), indicating a breakdown of microtubules (Jaworski et al., *Am J Pathol* 179:2001-2015 (2011)). Furthermore, we observed progerin-induced phenotypes that were exclusive to either PINK1-Q456X or Parkin-V324A iPSC-derived grafts. PINK1 grafts contained cells with enlarged mitochondria, a phenotype much more pronounced in progerin overexpressing cells (area=0.167 $\mu m^2$ compared to 0.0387 $\mu m^2$ for PINK1+ nuclear-GFP, p=0.0005; FIG. 16F and FIG. 17F).

Immunocytochemistry for NURR1 and TH in iPSC-mDA neurons replated in vitro and fixed one-day post transplant. At least 50% of cells already expressed the synapsin-driven transgene at this timepoint. FIG. 17A. Immunohistochemistry for TH and GFP at six months post transplant demonstrates a dramatic loss of TH+PD iPSC-derived mDA neurons when progerin is overexpressed. This pattern of TH loss in controls and PD mutants is similar to what was observed at three months post transplant (see FIG. 16). Dotted line defines the graft. Asterisks denote the corpus callosum.

Figure 17E:
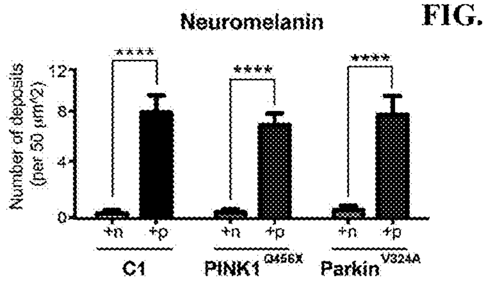

Insets show a representative GFP+ nucleus. FIG. 17B. Ultrastructural analysis by transmission electron microscopy (EM). Representative (FIG. 17C) TH+ dendrites and (FIG. 17D) GFP+ nuclei are outlined and each labeled with a D or N, respectively. Number at bottom left represents the average number of TH-immunogold particles per μm2. Asterisk identifies a fibrillar body. Quantification of neuromelanin deposits from EM analysis. Ten 50 μm2 regions were analyzed per animal. FIG. 17E. Quantification of the area of 25 mitochondria in PINK1-Q456X animals from EM analysis. *p<0.001 p<0.0001 according to Student's t tests. FIG. 17**F.

Figure 16G:
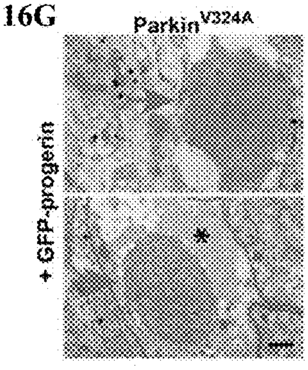
Figure 17F:
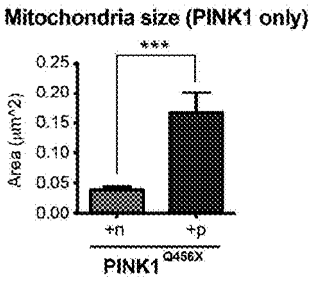

In contrast, Parkin mutant grafts showed less dramatic mitochondrial defects (such as abnormal mitochondrial fusion; but more strikingly, exhibited large multilamellar inclusions (FIG. 16G). Multilamellar inclusions have been observed in various neurodegenerative models (Cheng et al. *J Neurosci* 31:2125-2135, (2011); Hoopfer et al., *Neuron* 50:883-895 (2006); Phillips et al., *J Neurosci* 28:6569-6582 (2008) and are considered to be a precursor to the characteristic Lewy bodies found in surviving mDA neurons in brains from Parkinson's patients (Fornai et al., *J Neurochem* 88:114-123 (2004). The presence of these neuronal inclusions indicates decreased function of the ubiquitin-proteasome pathway caused by the loss of the normal Parkin function. However, the dependence of the phenotype on progerin expression suggests that age-related factors contribute to this dysfunction.

Schematic illustration of the transplantation studies into 6-OHDA lesioned Parkinsonian mice. FIG. 16A. Rotational behavior analysis of lesioned mice transplanted with control or PD mutant iPSCderived mDA neurons expressing hSyn::nuclear-GFP or hSyn::GFP-progerin. Mice were lesioned and tested for amphetamine-induced rotation behavior twice prior to grafting. Dotted line indicates threshold for successful lesioning. Pink symbols identify successfully lesioned animals that did not show recovery. n=3-5 animals per treatment group. FIG. 16B. Assessment at 3 months post transplant revealed a dramatic loss of TH+mDA neurons in PD mutants overexpressing progerin that was observed to a much lesser degree with the control transfection or in apparently healthy cells. FIG. 16C. Quantification of the percentage of GFP+ cells that are TH+. Data are presented as mean±SEM. n=3 mice per condition. FIG. 16D. Ultrastructural analysis 6 months after transplantation revealed an accumulation of neuromelanin with lipofuscin deposits (E, yellow arrowheads) in grafts with progerin overexpression. Strikingly, the PINK1 mutant graft with progerin displayed enlarged mitochondria. FIG. 16E-G. Representative mitochondria were compared (indicated by orange arrows in +nuclear27 GFP and +GFP-progerin groups) while the Parkin mutant graft with progerin had large multilamellar bodies (G, pink arrows). These phenotypes were not observed in any other treatment groups. Asterisks in (E) and (G) indicate a fibrillar bodies. FIG. 16F.

The presently disclosed in vivo results corroborate the in vitro data that the age of iPSC-derived mDA neurons is reset to a "young" state not conducive to modeling late-onset features of human disease. In contrast, progerin-induced neuronal aging reveals phenotypes consistent with normal aging as well as disease-associated phenotypes that reflect the synergistic interaction of PD genotype and age in modeling late-onset neurodegenerative aspects of PD.

An apoptotic phenotype demonstrated that progerin increases the percentage of apoptotic cells in the culture based on nuclear condensation data. Those data can be further evaluated using quantitative TUNEL assays to compare PD-iPSC and control-iPSC derived mDA neuron in the presence or absence of progerin.

An α-synuclein accumulation phenotype can be monitored using α-synuclein levels and cellular localization using Western blot analysis and immunocytochemistry. These data address whether induced aging affects the production of processing of α-synuclein in mDA neurons.

Example 38 (Prophetic)

Method for Screening Drugs Using Age-modified Cells iPSC can be obtained, for example, from human fibroblasts by methodology that is disclosed herein and as otherwise known in the art. Age-modified somatic cells can be obtained from iPSC by differentiation and contact with a progerin-like protein. Specialized age-modified somatic cells can thus be obtained having the characteristics of somatic cells isolated from brain, heart, liver, kidney, spleen, muscle, skin, lung, blood, artery, eye, bone marrow, and the lymphatic system. Differentiation protocols yielding such somatic cells are known, including cardiomyocytes (See, e.g., Van Oorschot A A et al., Panminerva Med. 2010 June; 52(2):97-110), hepatocytes (See, e.g., Alaimo G. et al., *J Cell Physiol.* 2013 June; 228(6):1249-54), kidney cells (See, e.g., De Chiara L. et al., J Am Soc Nephrol. 2014 February; 25(2):316-28), pancreatic beta cells (See, e.g., Roche E. et al., J Stem Cells. 2012; 7(4):211-28), white blood cells (See, e.g., de Pooter R F et al., Methods Mol Biol. 2007; 380:73-81).

Such age-modified somatic cells can be generated by contacting them with progerin or a progerin-like protein. Contact can be affected through transient or constitutive expression of progerin or other progerin-like protein, as described herein. In some embodiments, the resulting age-modified somatic cells will also express a disease marker signature; in other embodiments they will simply be aged by contact with a progerin-like protein. The aged somatic cells (both expressing and not expressing disease marker signature) will be purified and used for screening candidate drugs, using known screening methods, such as high throughput screening.

Once cells are ready for screening, they can be plated to test various plating densities and cell culture vessels. For example, these cells can be plated on 6-well, 24-well, 96-well, 384-well plates or any other platforms that facilitate drug screening. Times for initiation and duration of trophic factor withdrawal will also be optimized once a suitable HTS format is selected.

Drug screens based on stem-cell derived somatic cells have been described. See, e.g., Yang et al., *Cell Stem Cell* 12:713-726 (2013). Briefly, a small molecule survival screen was carried out using iPSC-derived motor neurons (MNs) from both wild-type and mutant SOD1 mouse embryonic stem cells to search for drugs to counteract MN death in amyotrophic lateral sclerosis (ALS). Mouse ESCs were differentiated into MNs and plated in 96-well or 384-well plates. Additionally, human MNs derived from human ESCs and iPSCs after 30 days of differentiation, were also used. For the small molecule screen, freshly dissociated cells were plated at a density of 8,000 GFP+ cells (384-well plate) or 30,000 GFP+ cells (96-well plate) per well. Four days later, trophic factors were removed, and individual compounds were added to the wells. For the primary screen each compound was tested at three concentrations (0.1 mM, 1 mM, and 10 mM) in duplicate. After an additional 72 hr (day 7), cells were fixed and stained, and the number of MNs surviving was analyzed by counting the remaining GFP+ cells in the whole well. Survival is measured as fold increase compared to cultures maintained without trophic factors. Using this method, Yang and colleagues discovered that the compound kenpaullone had an impressive ability to prolong the healthy survival of MNs.

By combining age-modification methods described in the present disclosure and an HTS platform, drug screening can be performed on cells that represent late-onset human diseases. According to methods of the present disclosure, age-modified cells with appropriate age and/or maturation markers can be generated from a somatic cell or from a stem cell. For example, an age-appropriate iPSC-derived mDA neuron can be generated by contacting a iPSC derived neuron with a progerin-like protein. Cells to be tested in a drug screen can be plated to test various plating densities and cell culture vessels. For example, cells can be plated on 6-well, 24-well, 96-well, 384-well plates or any other platforms that facilitate the drug screening. Times for initiation and duration of trophic factor withdrawal will also be optimized once a suitable HTS format is selected.

Molecules for use in a drug screen can come from a variety of sources, including small molecule compound libraries that can be designed in-house or obtained commercially. In the case of age-appropriate iPSC-derived mDA neurons, known drug molecules for neurodegenerative diseases, such as Parkinson's disease, which include biological and small molecules, can be tested. Such molecules can be screened at different concentrations, in combination with different cell densities, to optimize drug screen efficacy. For example, Yang et al. screened a collected of approximately 5000 small molecules to search for an ALS drug. For the primary screen, each compound was tested at three concentrations (0.1 mM, 1 mM, and 10 mM) in duplicate. After an additional 72 hr (day 7), MN cells were fixed, stained and accessed for survival. Yang et al., Id.

The phenotypic changes of the age-modified cells after exposure to candidate compounds (whether small molecules or biologics) can be selected according to the disease intended to be treated as well as according to the intended effects of these compounds/molecules on these cells. These phenotypic changes include, but not limited to, cell survival, morphological changes of the cells, secretion of certain factors by the cells, expression of certain cell surface molecules, interaction of cells with other cells and/or with a solid support, changes in optical, electrical, and chemical properties of the cell, fluorescence signals of the cell (e.g., when the cells are transfected with a fluorescent protein, such as GFP-progerin, etc.) and attenuation or elimination of disease markers, among others. One application of the methods described by the present disclosure is to screen for drugs that can prolong the healthy survival of neuronal cells that are key to neurodegenerative diseases such as Parkinson's and Alzheimer's diseases. Thus, a drug screen can be designed to select compounds that will promote survival of neurons. In the case of PD, age-modified mDA neurons derived from iPSC can be cultured, plated and exposed to compounds and their survival rate accessed. Furthermore, additional markers can be utilized as a basis for the drug screen in addition to cell survival. For example, aging/maturation-related markers, such as those listed in Table 2 or Table 3, can be used as criteria for drug screens. Compounds that can slow, halt or reverse the expression of one or more aging or disease markers could be candidates for drugs that may help treat these neurodegenerative diseases.

Hits can be defined as compounds/molecules that will effectively reverse one or more age-related or disease-related marker signatures described above. For example, if cell survival is used and an endpoint, molecules can be selected that substantially increase the number of surviving cells (e.g., age-appropriate iPSC-derived mDA neurons) while preserving cell-appropriate morphological characteristics.

Candidate compounds that are selected from a primary screen can, optionally, be retested and subjected to additional testing including, but not limited to, dose-response and toxicity assays. Lead compounds can be selected and can be structurally modified to improve desired characteristics and/or to reduce side effects. Other improvements to the lead compounds can include increased absorption, longer half-life, higher affinity to cells, and enhancement of local and/or systemic delivery. Lead compounds and modified variants thereof can be further studied in preclinical studies including in suitable cell culture and animal model systems and, those exhibiting favorable therapeutic and toxicity profiles can be subjected to further in vivo testing in human clinical trials.

All references cited herein are incorporated by reference in their entirety.

```
SEQ ID NO. 1:
ATGGAGACCCCGTCCCAGCGGCGCGCCACCCGCAGCGGGG

CGCAGGCCAGCTCCACTCCGCTGTCGCCCACCCGCATCAC

CCGGCTGCAGGAGAAGGAGGACCTGCAGGAGCTCAATGAT

CGCTTGGCGGTCTACATCGACCGTGTGCGCTCGCTGGAAA

CGGAGAACGCAGGGCTGCGCCTTCGCATCACCGAGTCTGA

AGAGGTGGTCAGCCGCGAGGTGTCCGGCATCAAGGCCGCC

TACGAGGCCGAGCTCGGGGATGCCCGCAAGACCCTTGACT

CAGTAGCCAAGGAGCGCGCCCGCCTGCAGCTGGAGCTGAG

CAAAGTGCGTGAGGAGTTTAAGGAGCTGAAAGCGCGCAAT

ACCAAGAAGGAGGGTGACCTGATAGCTGCTCAGGCTCGGC

TGAAGGACCTGGAGGCTCTGCTGAACTCCAAGGAGGCCGC

ACTGAGCACTGCTCTCAGTGAGAAGCGCACGCTGGAGGGC

GAGCTGCATGATCTGCGGGGCCAGGTGGCCAAGCTTGAGG

CAGCCCTAGGTGAGGCCAAGAAGCAACTTCAGGATGAGAT

GCTGCGGCGGGTGGATGCTGAGAACAGGCTGCAGACCATG

AAGGAGGAACTGGACTTCCAGAAGAACATCTACAGTGAGG

AGCTGCGTGAGACCAAGCGCCGTCATGAGACCCGACTGGT

GGAGATTGACAATGGGAAGCAGCGTGAGTTTGAGAGCCGG

CTGGCGGATGCGCTGCAGGAACTGCGGGCCCAGCATGAGG

ACCAGGTGGAGCAGTATAAGAAGGAGCTGGAGAAGACTTA

TTCTGCCAAGCTGGACAATGCCAGGCAGTCTGCTGAGAGG

AACAGCAACCTGGTGGGGGCTGCCCACGAGGAGCTGCAGC

AGTCGCGCATCCGCATCGACAGCCTCTCTGCCCAGCTCAG

CCAGCTCCAGAAGCAGCTGGCAGCCAAGGAGGCGAAGCTT

CGAGACCTGGAGGACTCACTGGCCCGTGAGCGGGACACCA
```

-continued

GCCGGCGGCTGCTGGCGGAAAAGGAGCGGGAGATGGCCGA

GATGCGGGCAAGGATGCAGCAGCAGCTGGACGAGTACCAG

GAGCTTCTGGACATCAAGCTGGCCCTGGACATGGAGATCC

ACGCCTACCGCAAGCTCTTGGAGGGCGAGGAGGAGAGGCT

ACGCCTGTCCCCCAGCCCTACCTCGCAGCGCAGCCGTGGC

CGTGCTTCCTCTCACTCATCCCAGACACAGGGTGGGGGCA

GCGTCACCAAAAAGCGCAAACTGGAGTCCACTGAGAGCCG

CAGCAGCTTCTCACAGCACGCACGCACTAGCGGGCGCGTG

GCCGTGGAGGAGGTGGATGAGGAGGGCAAGTTTGTCCGGC

TGCGCAACAAGTCCAATGAGGACCAGTCCATGGGCAATTG

GCAGATCAAGCGCCAGAATGGAGATGATCCCTTGCTGACT

TACCGGTTCCCACCAAAGTTCACCCTGAAGGCTGGGCAGG

TGGTGACGATCTGGGCTGCAGGAGCTGGGGCCACCCACAG

CCCCCCTACCGACCTGGTGTGGAAGGCACAGAACACCTGG

GGCTGCGGGAACAGCCTGCGTACGGCTCTCATCAACTCCA

CTGGGGAAGAAGTGGCCATGCGCAAGCTGGTGCGCTCAGT

GACTGTGGTTGAGGACGACGAGGATGAGGATGGAGATGAC

CTGCTCCATCACCACCATGGCTCCCACTGCAGCAGCTCGG

GGGACCCCGCTGAGTACAACCTGCGCTCGCGCACCGTGCT

GTGCGGGACCTGCGGGCAGCCTGCCGACAAGGCATCTGCC

AGCGGCTCAGGAGCCCAGAGCCCCCAGAACTGCAGCATCA

TGTAA

SEQ ID NO. 2:
ATGGTGAGCAAGGGCGCCGAGCTGTTCACCGGCATCGTGC

CCATCCTGATCGAGCTGAATGGCGATGTGAATGGCCACAA

GTTCAGCGTGAGCGGCGAGGGCGAGGGCGATGCCACCTAC

GGCAAGCTGACCCTGAAGTTCATCTGCACCACCGGCAAGC

TGCCTGTGCCCTGGCCCACCCTGGTGACCACCCTGAGCTA

CGGCGTGCAGTGCTTCTCACGCTACCCCGATCACATGAAG

CAGCACGACTTCTTCAAGAGCGCCATGCCTGAGGGCTACA

TCCAGGAGCGCACCATCTTCTTCGAGGATGACGGCAACTA

CAAGTCGCGCGCCGAGGTGAAGTTCGAGGGCGATACCCTG

GTGAATCGCATCGAGCTGACCGGCACCGATTTCAAGGAGG

ATGGCAACATCCTGGGCAATAAGATGGAGTACAACTACAA

CGCCCACAATGTGTACATCATGACCGACAAGGCCAAGAAT

GGCATCAAGGTGAACTTCAAGATCCGCCACAACATCGAGG

ATGGCAGCGTGCAGCTGGCCGACCACTACCAGCAGAATAC

CCCCATCGGCGATGGCCCTGTGCTGCTGCCCGATAACCAC

TACCTGTCCACCCAGAGCGCCCTGTCCAAGGACCCCAACG

AGAAGCGCGATCACATGATCTACTTCGGCTTCGTGACCGC

CGCCGCCATCACCCACGGCATGGATGAGCTGTACAAGTCC

-continued

GGACTTAAGGCCTCTGTCGACagcagtctctgtccttcga cccgagccccgcgccctttccgggacccctgccccgcggg cagcgctgccaacctgccggccATGGAGACCCCGTCCCAG

CGGCGCGCCACCCGCAGCGGGGCGCAGGCCAGCTCCACTC

CGCTGTCGCCCACCCGCATCACCCGGCTGCAGGAGAAGGA

GGACCTGCAGGAGCTCAATGATCGCTTGGCGGTCTACATC

GACCGTGTGCGCTCGCTGGAAACGGAGAACGCAGGGCTGC

GCCTTCGCATCACCGAGTCTGAAGAGGTGGTCAGCCGCGA

GGTGTCCGGCATCAAGGCCGCCTACGAGGCCGAGCTCGGG

GATGCCCGCAAGACCCTTGACTCAGTAGCCAAGGAGCGCG

CCCGCCTGCAGCTGGAGCTGAGCAAAGTGCGTGAGGAGTT

TAAGGAGCTGAAAGCGCGCAATACCAAGAAGGAGGGTGAC

CTGATAGCTGCTCAGGCTCGGCTGAAGGACCTGGAGGCTC

TGCTGAACTCCAAGGAGGCCGCACTGAGCACTGCTCTCAG

TGAGAAGCGCACGCTGGAGGGCGAGCTGCATGATCTGCGG

GGCCAGGTGGCCAAGCTTGAGGCAGCCCTAGGTGAGGCCA

AGAAGCAACTTCAGGATGAGATGCTGCGGCGGGTGGATGC

TGAGAACAGGCTGCAGACCATGAAGGAGGAACTGGACTTC

CAGAAGAACATCTACAGTGAGGAGCTGCGTGAGACCAAGC

GCCGTCATGAGACCCGACTGGTGGAGATTGACAATGGGAA

GCAGCGTGAGTTTGAGAGCCGGCTGGCGGATGCGCTGCAG

GAACTGCGGGCCCAGCATGAGGACCAGGTGGAGCAGTATA

AGAAGGAGCTGGAGAAGACTTATTCTGCCAAGCTGGACAA

TGCCAGGCAGTCTGCTGAGAGGAACAGCAACCTGGTGGGG

GCTGCCCACGAGGAGCTGCAGCAGTCGCGCATCCGCATCG

ACAGCCTCTCTGCCCAGCTCAGCCAGCTCCAGAAGCAGCT

GGCAGCCAAGGAGGCGAAGCTTCGAGACCTGGAGGACTCA

CTGGCCCGTGAGCGGGACACCAGCCGGCGGCTGCTGGCGG

AAAAGGAGCGGGAGATGGCCGAGATGCGGGCAAGGATGCA

GCAGCAGCTGGACGAGTACCAGGAGCTTCTGGACATCAAG

CTGGCCCTGGACATGGAGATCCACGCCTACCGCAAGCTCT

TGGAGGGCGAGGAGGAGAGGCTACGCCTGTCCCCCAGCCC

TACCTCGCAGCGCAGCCGTGGCCGTGCTTCCTCTCACTCA

TCCCAGACACAGGGTGGGGGCAGCGTCACCAAAAAGCGCA

AACTGGAGTCCACTGAGAGCCGCAGCAGCTTCTCACAGCA

CGCACGCACTAGCGGGCGCGTGGCCGTGGAGGAGGTGGAT

GAGGAGGGCAAGTTTGTCCGGCTGCGCAACAAGTCCAATG

AGGACCAGTCCATGGGCAATTGGCAGATCAAGCGCCAGAA

TGGAGATGATCCCTTGCTGACTTACCGGTTCCCACCAAAG

TTCACCCTGAAGGCTGGGCAGGTGGTGACGATCTGGGCTG

-continued

CAGGAGCTGGGGCCACCCACAGCCCCCCTACCGACCTGGT

GTGGAAGGCACAGAACACCTGGGGCTGCGGGAACAGCCTG

CGTACGGCTCTCATCAACTCCACTGGGGAAGAAGTGGCCA

TGCGCAAGCTGGTGCGCTCAGTGACTGTGGTTGAGGACGA

CGAGGATGAGGATGGAGATGACCTGCTCCATCACCACCAT

GGCTCCCACTGCAGCAGCTCGGGGGACCCCGCTGAGTACA

ACCTGCGCTCGCGCACCGTGCTGTGCGGGACCTGCGGGCA

GCCTGCCGACAAGGCATCTGCCAGCGGCTCAGGAGCCCAG

AGCCCCCAGAACTGCAGCATCATGTAA

REFERENCES

Akalin et al., *Genome Biol* 13:R87 (2012)
Akalin et al., *PLoS Genet* 8:e1002781 (2012)
Anders & Huber, *Genome Biol* 11:R106 (2010)
Cerami et al., *PLoS One* 5:e8918 (2010)
Hetman & Pietrzak, *Trends Neurosci* 35:305-314 (2012)
Johnson et al., *Curr Opin Cell Biol* 10:332-338 (1998)
McCord et al., *Genome Res* 23:260-269 (2013)
Nuytemans et al., *Hum Mutat* 31:763-780 (2010)
Rieker et al., *J Neurosci* 31:453-460 (2011)
Ross-Innes et al., *Nature* 481:389-393 (2012)
Sinclair et al., *Science* 277:1313-1316 (1997)
Stroud et al., *Genome Biol* 12:R54 (2011)
Studer, et al., *Proc Natl Acad Sci* 106:12759-12764 (2009)
Tarca et al., *Bioinformatics* 25:75-82 (2009)
Vera et al., *Cell Rep* 2:732-737 (2012)

The invention claimed is:

1. A method for drug screening, said method comprising expressing an exogenous progerin protein in a cell selected from the group consisting of an embryonic stem cell (ESC), an ESC-derived somatic cell, an induced pluripotent stem cell (iPSC), and an iPSC-derived somatic cell, that is deficient in one or more chronological markers, wherein the exogenous progerin protein is expressed in an amount and for a period of time sufficient to induce the production of said one or more chronological markers, thereby producing an age-modified cell, contacting the age-modified cell with a candidate drug, and detecting an alteration in at least one of the survival, biological activity, morphology or structure of the age-modified cell.

2. The method of claim 1, wherein said cell that is deficient in said one or more chronological markers is an ESC or iPSC.

3. The method of claim 1, wherein said cell that is deficient in said one or more chronological markers is an ESC-derived somatic cell or an iPSC-derived somatic cell.

4. The method of claim 3, wherein said ESC-derived somatic cell or iPSC-derived somatic cell is produced by a method comprising exposing an ESC or iPSC with one or more differentiation factors, wherein said differentiation factors promote the differentiation of said ESC or iPSC into said ESC-derived somatic cell or iPSC-derived somatic cell.

5. The method of claim 4, wherein said somatic cell is selected from the group consisting of a fibroblast cell, a liver cell, a heart cell, a central nervous system (CNS) cell, a peripheral nervous system (PNS) cell, a kidney cell, a lung cell, a hematopoietic cell, a pancreatic beta cell, a bone marrow cell, an osteoblast cell, an osteoclast cell, and an endothelial cell.

6. The method of claim 5, wherein said CNS cell is selected from the group consisting of a neural progenitor, a neuron, and a glial cell.

7. The method of claim 5, wherein said CNS cell is a midbrain dopamine (mDA) neuronal cell.

8. The method of claim 1, wherein said progerin is human progerin.

9. The method of claim 1, wherein said one or more chronological markers is selected from the group consisting of an age-associated marker, a maturation-associated marker, and a disease-associated marker.

10. The method of claim 9, wherein said one or more chronological markers is an age-associated marker selected from the group consisting of nuclear folding and blebbing; reduction of nuclear organization proteins; reduction of heterochromatin; accumulation of DNA damage; increased mitochondrial ROS generation; telomere shortening; upregulation of senescence markers; dendrite shortening; neurodegeneration gene expression; hyperactivation of p-AKT; decrease of TH+neurons; accumulation of neuromelanin; reduced contractile and luistropic function; increased cell diameter or hypertrophy; fibrosis and apoptosis; reduced proliferation; altered organizational patterns of sarcomeric proteins, calcium processing, and electrophysiology properties; decreased graft-host integration; arrhythmias; decreased insulin secretion; loss of proliferation capacity; amylin aggregation; altered glucose responsiveness; tubular atrophy, fibrosis, or glomerulosclerosis; terminal differentiation; mineralization; increase in nuclei size and polyploidy; increase in mitochondrial volume; lipofuscin deposition; and apoptosis.

11. The method of claim 10, wherein said one or more age-associated markers is measured by detecting a marker selected from the group consisting of Lamin A/C, LAP2α, H3K9me3, HP1γ, γH2AX, MitoSOX, Telomeric repeats, SA-β-Gal, MAP2ab, RNA-seq, p-AKT, p-4EBP1, p-ULK1, TH, cleaved caspase-3, MHC, SERCA2, NCX1, mitochondrial proteins and heteroplasmy, Cx43, ANP, BNP, ERK1/2, NFAT, calcineurin, S6 kinase, TERT, IGF-1, PI3K, ET-1, SIRT1, SIRT7, caspase, AIF, survivin, cyclin D1, cyclin D2, cyclin D3, pRb, p130, CDK2, ATP production, glucose oxidation, KATP-channel, Foxm1, Pdx1, MTS, D cyclins, p16Ink4a, Cdk4/6, IAPP/amylin, MMP20, IGF1R, FAM83F, MMP25, ADCY1, Col1A1, osteocalcin, osteonectin, osteopontin, ALP, calcium deposit, cathepsin K, MMP9, RANKL, Lipofuscin, decline in intracellular proteinolysis, DAT, pacemaker activity, neuromelanin, and Notch signaling.

12. The method of claim 1, wherein said cell that is deficient in one or more chronological markers is derived from an individual not afflicted with Hutchinson-Gilford progeria syndrome (HGPS).

13. The method of claim 1, wherein the amount of exogenous progerin protein is within the range from about 10 times to about 5000 times of the level of expression of endogenous progerin.

14. The method of claim 1, wherein the amount of exogenous progerin protein is within the range from about 40 times to about 500 times of the level of expression of endogenous progerin.

* * * * *

SEQUENCE LISTING

<160> NUMBER OF SEQ ID NOS: 24

<210> SEQ ID NO 1
<211> LENGTH: 1845
<212> TYPE: DNA
<213> ORGANISM: Homo sapiens

<400> SEQUENCE: 1

```
atggagaccc cgtcccagcg gcgcgccacc cgcagcgggg cgcaggccag ctccactccg      60

ctgtcgccca cccgcatcac ccggctgcag gagaaggagg acctgcagga gctcaatgat     120

cgcttggcgg tctacatcga ccgtgtgcgc tcgctggaaa cggagaacgc agggctgcgc     180

cttcgcatca ccgagtctga agaggtggtc agccgcgagg tgtccggcat caaggccgcc     240

tacgaggccg agctcgggga tgcccgcaag acccttgact cagtagccaa ggagcgcgcc     300

cgcctgcagc tggagctgag caaagtgcgt gaggagttta aggagctgaa agcgcgcaat     360

accaagaagg agggtgacct gatagctgct caggctcggc tgaaggacct ggaggctctg     420

ctgaactcca aggaggccgc actgagcact gctctcagtg agaagcgcac gctggagggc     480

gagctgcatg atctgcgggg ccaggtggcc aagcttgagg cagccctagg tgaggccaag     540

aagcaacttc aggatgagat gctgcggcgg gtggatgctg agaacaggct gcagaccatg     600

aaggaggaac tggacttcca gaagaacatc tacagtgagg agctgcgtga gaccaagcgc     660

cgtcatgaga cccgactggt ggagattgac aatgggaagc agcgtgagtt tgagagccgg     720

ctggcggatg cgctgcagga actgcgggcc cagcatgagg accaggtgga gcagtataag     780

aaggagctgg agaagactta ttctgccaag ctggacaatg ccaggcagtc tgctgagagg     840

aacagcaacc tggtgggggc tgcccacgag gagctgcagc agtcgcgcat ccgcatcgac     900

agcctctctg cccagctcag ccagctccag aagcagctgg cagccaagga ggcgaagctt     960

cgagacctgg aggactcact ggcccgtgag cgggacacca gccggcggct gctggcggaa    1020

aaggagcggg agatggccga gatgcgggca aggatgcagc agcagctgga cgagtaccag    1080

gagcttctgg acatcaagct ggccctggac atggagatcc acgcctaccg caagctcttg    1140

gagggcgagg aggagaggct acgcctgtcc cccagcccta cctcgcagcg cagccgtggc    1200

cgtgcttcct ctcactcatc ccagacacag ggtgggggca gcgtcaccaa aaagcgcaaa    1260

ctggagtcca ctgagagccg cagcagcttc tcacagcacg cacgcactag cgggcgcgtg    1320

gccgtggagg aggtggatga ggagggcaag tttgtccggc tgcgcaacaa gtccaatgag    1380
```

```
gaccagtcca tgggcaattg gcagatcaag cgccagaatg gagatgatcc cttgctgact   1440

taccggttcc caccaaagtt caccctgaag gctgggcagg tggtgacgat ctgggctgca   1500

ggagctgggg ccacccacag ccccccctacc gacctggtgt ggaaggcaca gaacacctgg   1560

ggctgcggga acagcctgcg tacggctctc atcaactcca ctggggaaga agtggccatg   1620

cgcaagctgg tgcgctcagt gactgtggtt gaggacgacg aggatgagga tggagatgac   1680

ctgctccatc accaccatgg ctcccactgc agcagctcgg gggaccccgc tgagtacaac   1740

ctgcgctcgc gcaccgtgct gtgcgggacc tgcgggcagc ctgccgacaa ggcatctgcc   1800

agcggctcag gagcccagag cccccagaac tgcagcatca tgtaa                   1845
```

```
<210> SEQ ID NO 2
<211> LENGTH: 2667
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

atggtgagca agggcgccga gctgttcacc ggcatcgtgc ccatcctgat cgagctgaat     60

ggcgatgtga atggccacaa gttcagcgtg agcggcgagg gcgagggcga tgccacctac    120

ggcaagctga ccctgaagtt catctgcacc accggcaagc tgcctgtgcc ctggcccacc    180

ctggtgacca ccctgagcta cggcgtgcag tgcttctcac gctaccccga tcacatgaag    240

cagcacgact tcttcaagag cgccatgcct gagggctaca tccaggagcg caccatcttc    300

ttcgaggatg acggcaacta caagtcgcgc gccgaggtga agttcgaggg cgataccctg    360

gtgaatcgca tcgagctgac cggcaccgat ttcaaggagg atggcaacat cctgggcaat    420

aagatggagt acaactacaa cgcccacaat gtgtacatca tgaccgacaa ggccaagaat    480

ggcatcaagg tgaacttcaa gatccgccac aacatcgagg atggcagcgt gcagctggcc    540

gaccactacc agcagaatac ccccatcggc gatggccctg tgctgctgcc cgataaccac    600

tacctgtcca cccagagcgc cctgtccaag gaccccaacg agaagcgcga tcacatgatc    660

tacttcggct tcgtgaccgc cgccgccatc acccacggca tggatgagct gtacaagtcc    720

ggacttaagg cctctgtcga cagcagtctc tgtccttcga cccgagcccc gcgccctttc    780

cgggacccct gccccgcggg cagcgctgcc aacctgccgg ccatggagac cccgtcccag    840

cggcgcgcca cccgcagcgg ggcgcaggcc agctccactc cgctgtcgcc cacccgcatc    900

acccggctgc aggagaagga ggacctgcag gagctcaatg atcgcttggc ggtctacatc    960

gaccgtgtgc gctcgctgga aacggagaac gcagggctgc gccttcgcat caccgagtct   1020

gaagaggtgg tcagccgcga ggtgtccggc atcaaggccg cctacgaggc cgagctcggg   1080

gatgcccgca agacccttga ctcagtagcc aaggagcgcg cccgcctgca gctggagctg   1140

agcaaagtgc gtgaggagtt taaggagctg aaagcgcgca ataccaagaa ggagggtgac   1200

ctgatagctg ctcaggctcg gctgaaggac ctggaggctc tgctgaactc caaggaggcc   1260

gcactgagca ctgctctcag tgagaagcgc acgctggagg gcgagctgca tgatctgcgg   1320

ggccaggtgg ccaagcttga ggcagcccta ggtgaggcca agaagcaact tcaggatgag   1380

atgctgcggc gggtggatgc tgagaacagg ctgcagacca tgaaggagga actggacttc   1440

cagaagaaca tctacagtga ggagctgcgt gagaccaagc gccgtcatga gacccgactg   1500

gtggagattg acaatgggaa gcagcgtgag tttgagagcc ggctggcgga tgcgctgcag   1560
```

gaactgcggg cccagcatga ggaccaggtg gagcagtata agaaggagct ggagaagact 1620
tattctgcca agctggacaa tgccaggcag tctgctgaga ggaacagcaa cctggtgggg 1680
gctgcccacg aggagctgca gcagtcgcgc atccgcatcg acagcctctc tgcccagctc 1740
agccagctcc agaagcagct ggcagccaag gaggcgaagc ttcgagacct ggaggactca 1800
ctggcccgtg agcgggacac cagccggcgg ctgctggcgg aaaaggagcg ggagatggcc 1860
gagatgcggg caaggatgca gcagcagctg gacgagtacc aggagcttct ggacatcaag 1920
ctggccctgg acatggagat ccacgcctac cgcaagctct tggagggcga ggaggagagg 1980
ctacgcctgt cccccagccc tacctcgcag cgcagccgtg gccgtgcttc ctctcactca 2040
tcccagacac agggtggggg cagcgtcacc aaaaagcgca aactggagtc cactgagagc 2100
cgcagcagct tctcacagca cgcacgcact agcgggcgcg tggccgtgga ggaggtggat 2160
gaggagggca agtttgtccg gctgcgcaac aagtccaatg aggaccagtc catgggcaat 2220
tggcagatca agcgccagaa tggagatgat cccttgctga cttaccggtt cccaccaaag 2280
ttcaccctga aggctgggca ggtggtgacg atctgggctg caggagctgg ggccacccac 2340
agccccccta ccgacctggt gtggaaggca cagaacacct ggggctgcgg gaacagcctg 2400
cgtacggctc tcatcaactc cactggggaa gaagtggcca tgcgcaagct ggtgcgctca 2460
gtgactgtgg ttgaggacga cgaggatgag gatggagatg acctgctcca tcaccaccat 2520
ggctcccact gcagcagctc gggggacccc gctgagtaca acctgcgctc gcgcaccgtg 2580
ctgtgcggga cctgcgggca gcctgccgac aaggcatctg ccagcggctc aggagcccag 2640
agcccccaga actgcagcat catgtaa 2667

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 3
gtcaacccca ccgtgttctt 20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 4
ctgctgtctt tgggaccttg t 21

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5
tggtgagcaa gggcgccgag ctg 23

<210> SEQ ID NO 6

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

ttacatgatg ctgcagttct g                                                21


<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

gctcttctgc ctccagtgtc                                                  20


<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

acatgatgct gcagttctgg                                                  20


<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

ctcagtgact gtggttgagg a                                                21


<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

agtgcaggct cggcctc                                                     17


<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

ctgagccttg tctcccttcc                                                  20


<210> SEQ ID NO 12
<211> LENGTH: 20
```

<212> TYPE: DNA
<213> ORGANISM: Artificial Sequence
<220> FEATURE:
<223> OTHER INFORMATION: Description of Artificial Sequence: Synthetic
primer

<400> SEQUENCE: 12
gtggaaggca cagaacacct 20

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13
gtgaggagga cgcaggaa 18

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
ttatctagat ccggtggatc ctacc 25

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
gaaactggtt aagcaagaaa tcc 23

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
tgtgcaggac atgaaaaggt 20

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 17
gcgtcaggag ccctgagc 18

<210> SEQ ID NO 18
<211> LENGTH: 18
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 18

gacgcaggaa gcctccac                                                  18


<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

aaggcctctg tcgacagcag tctctgtcct tcgaccc                             37


<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

agaattcgca agcttcttcc acctcccacc tcattcc                             37


<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

ttggaccctc gtacagaagc taatacg                                        27


<210> SEQ ID NO 22
<211> LENGTH: 149
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

tttttttttt tttttttttt tttttttttt tttttttttt tttttttttt tttttttttt     60

tttttttttt tttttttttt tttttttttt tttttttttt tttttttttt tttttttttt    120

cttcctactc aggctttatt caaagacca                                     149


<210> SEQ ID NO 23
<211> LENGTH: 11
<212> TYPE: DNA
<213> ORGANISM: Homo sapiens

<400> SEQUENCE: 23

ccaggtgggy g                                                         11


<210> SEQ ID NO 24
<211> LENGTH: 11
<212> TYPE: DNA
```

-continued

<213> ORGANISM: Homo sapiens

<400> SEQUENCE: 24
ccaggtgggc g 11